(12) United States Patent
Manos et al.

(10) Patent No.: US 9,743,919 B2
(45) Date of Patent: Aug. 29, 2017

(54) STITCH LOCK FOR ATTACHING TWO OR MORE STRUCTURES

(75) Inventors: Jamie Manos, West Chester, PA (US); Kevin Henrichsen, Philadelphia, PA (US); William Miller, West Chester, PA (US); Daniel Vennard, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1414 days.

(21) Appl. No.: 13/283,002

(22) Filed: Oct. 27, 2011

(65) Prior Publication Data
US 2012/0150223 A1 Jun. 14, 2012

Related U.S. Application Data

(63) Continuation-in-part of application No. 13/172,619, filed on Jun. 29, 2011, now Pat. No. 9,451,938, and
(Continued)

(51) Int. Cl.
*A61B 17/04* (2006.01)
*A61B 17/00* (2006.01)
(Continued)

(52) U.S. Cl.
CPC ...... *A61B 17/0057* (2013.01); *A61B 17/0401* (2013.01); *A61B 17/0467* (2013.01); *A61B 17/0469* (2013.01); *A61B 17/0482* (2013.01); *A61B 17/0483* (2013.01); *A61B 17/0487* (2013.01); *A61B 17/842* (2013.01); *A61B 2017/00477* (2013.01);
(Continued)

(58) Field of Classification Search
CPC ........ A61B 2017/0459; A61B 17/0401; A61B 2017/0496
See application file for complete search history.

(56) References Cited

U.S. PATENT DOCUMENTS 233,475 A 10/1880 Cook et al.
261,501 A 7/1882 Vanermark
(Continued)

FOREIGN PATENT DOCUMENTS

CN 101056587 10/2007
DE 4207854 9/1993
(Continued)

OTHER PUBLICATIONS

U.S. Appl. No. 60/160,170, filed Oct. 20, 1999, Cauthen.
(Continued)

*Primary Examiner* — Gregory Anderson
*Assistant Examiner* — Christina Lauer
(74) *Attorney, Agent, or Firm* — Baker & Hostetler LLP

(57) ABSTRACT

An anchor assembly can include at least one anchor member, such as a pair of anchor members that are configured to be implanted in a target anatomical location in a first configuration, and can subsequently be actuated to an expanded configuration that secures the anchor members in the target anatomy. The anchor assembly can further include a connector member configured as a stitch lock that attaches the pair of anchor members together across a gap so as to approximate the anatomical defect.

33 Claims, 38 Drawing Sheets

Related U.S. Application Data a continuation-in-part of application No. 13/095,192, filed on Apr. 27, 2011, now Pat. No. 9,173,645.

(60) Provisional application No. 61/398,699, filed on Jun. 29, 2010, provisional application No. 61/432,755, filed on Jan. 14, 2011, provisional application No. 61/461,490, filed on Jan. 18, 2011, provisional application No. 61/443,142, filed on Feb. 15, 2011, provisional application No. 61/328,251, filed on Apr. 27, 2010.

(51) Int. Cl.
*A61B 17/84* (2006.01)
*A61B 17/06* (2006.01)
*A61B 17/29* (2006.01)

(52) U.S. Cl.
CPC ........... *A61B 2017/00623* (2013.01); *A61B 2017/00663* (2013.01); *A61B 2017/0406* (2013.01); *A61B 2017/0409* (2013.01); *A61B 2017/0414* (2013.01); *A61B 2017/0417* (2013.01); *A61B 2017/0419* (2013.01); *A61B 2017/0464* (2013.01); *A61B 2017/0475* (2013.01); *A61B 2017/0477* (2013.01); *A61B 2017/0496* (2013.01); *A61B 2017/0619* (2013.01); *A61B 2017/06042* (2013.01); *A61B 2017/06052* (2013.01); *A61B 2017/06176* (2013.01); *A61B 2017/292* (2013.01); *A61B 2017/2917* (2013.01)

(56) References Cited

U.S. PATENT DOCUMENTS

| | | |
|---|---|---|
| 330,087 A | 11/1885 | Binns |
| 400,743 A | 4/1889 | Brown |
| 2,490,364 A | 12/1949 | Livingston |
| 3,580,256 A | 5/1971 | Wilkinson |
| 3,867,728 A | 2/1975 | Stubstad et al. |
| 3,908,677 A | 9/1975 | Beach |
| 3,987,806 A | 10/1976 | Gilbert |
| 4,006,747 A | 2/1977 | Kronenthal et al. |
| 4,235,238 A | 11/1980 | Ogiv et al. |
| 4,669,473 A | 6/1987 | Richards et al. |
| 4,741,330 A | 5/1988 | Hayhurst |
| 4,778,990 A | 10/1988 | Laughlin |
| 4,994,028 A | 2/1991 | Leonard et al. |
| 4,994,069 A | 2/1991 | Ritchart et al. |
| 5,021,059 A | 6/1991 | Kensey et al. |
| 5,041,129 A | 8/1991 | Hayhurst et al. |
| 5,053,046 A | 10/1991 | Janese |
| 5,062,344 A | 11/1991 | Gerker |
| 5,120,596 A | 6/1992 | Yamada |
| 5,156,616 A | 10/1992 | Meadows et al. |
| 5,269,809 A | 12/1993 | Hayhurst et al. |
| 5,281,238 A | 1/1994 | Chin et al. |
| 5,403,348 A | 4/1995 | Bonutti |
| 5,417,691 A | 5/1995 | Hayhurst |
| 5,464,426 A | 11/1995 | Bonutti |
| 5,478,353 A | 12/1995 | Yoon |
| 5,507,754 A | 4/1996 | Green et al. |
| 5,522,846 A | 6/1996 | Bonutti |
| 5,527,343 A | 6/1996 | Bonutti |
| 5,540,703 A | 7/1996 | Barker et al. |
| 5,549,630 A | 8/1996 | Bonutti |
| 5,562,684 A | 10/1996 | Kammerer |
| 5,562,736 A | 10/1996 | Ray et al. |
| 5,571,189 A | 11/1996 | Kuslich |
| 5,584,862 A | 12/1996 | Bonutti |
| 5,601,557 A | 2/1997 | Hayhurst |
| 5,626,614 A | 5/1997 | Hart |
| 5,628,756 A | 5/1997 | Barker, Jr. et al. |
| 5,643,319 A | 7/1997 | Green et al. |
| 5,649,945 A | 7/1997 | Ray et al. |
| 5,699,657 A | 12/1997 | Paulson |
| 5,702,462 A | 12/1997 | Oberlander |
| 5,728,109 A | 3/1998 | Schulze et al. |
| 5,733,306 A | 3/1998 | Bonutti |
| 5,824,093 A | 10/1998 | Ray et al. |
| 5,906,626 A | 5/1999 | Carrillo |
| 5,941,900 A | 8/1999 | Bonutti |
| 5,944,739 A | 8/1999 | Zlock et al. |
| 5,948,002 A | 9/1999 | Bonutti |
| 5,951,590 A | 9/1999 | Goldfarb |
| 5,957,953 A | 9/1999 | DiPoto et al. |
| 5,970,697 A | 10/1999 | Jacobs et al. |
| 5,989,252 A | 11/1999 | Fumex |
| 6,056,773 A | 5/2000 | Bonutti |
| 6,068,648 A | 5/2000 | Cole |
| 6,077,292 A | 6/2000 | Bonutti |
| 6,110,183 A | 8/2000 | Cope |
| 6,113,611 A | 9/2000 | Allen et al. |
| 6,146,422 A | 11/2000 | Lawson |
| 6,179,860 B1 | 1/2001 | Fulton et al. |
| 6,187,048 B1 | 2/2001 | Milner et al. |
| 6,209,550 B1 | 4/2001 | Powell |
| 6,224,630 B1 | 5/2001 | Bao et al. |
| 6,245,107 B1 | 6/2001 | Ferree |
| 6,287,325 B1 | 9/2001 | Bonutti |
| 6,296,659 B1 | 10/2001 | Foerster |
| 6,306,159 B1 | 10/2001 | Schwartz et al. |
| 6,325,816 B1 | 12/2001 | Fulton et al. |
| 6,409,742 B1 | 6/2002 | Fulton et al. |
| 6,432,123 B2 | 8/2002 | Schwartz et al. |
| 6,482,235 B1 | 11/2002 | Lambrecht et al. |
| 6,508,839 B1 | 1/2003 | Lambrecht et al. |
| 6,511,498 B1 | 1/2003 | Fumex |
| 6,530,933 B1 | 3/2003 | Yeung et al. |
| 6,579,291 B1 | 6/2003 | Keith et al. |
| 6,592,625 B2 | 7/2003 | Cauthen |
| 6,638,291 B1 | 10/2003 | Ferrera et al. |
| 6,656,182 B1 | 12/2003 | Hayhurst |
| 6,689,125 B1 | 2/2004 | Keith et al. |
| 6,719,797 B1 | 4/2004 | Ferree |
| 6,758,855 B2 | 7/2004 | Fulton et al. |
| 6,964,674 B1 | 11/2005 | Matsuura et al. |
| 6,972,027 B2 | 12/2005 | Fallin et al. |
| 6,984,247 B2 | 1/2006 | Cauthen |
| 6,986,775 B2 | 1/2006 | Morales et al. |
| 6,991,643 B2 | 1/2006 | Saadat |
| 6,997,956 B2 | 2/2006 | Cauthen |
| 7,004,970 B2 | 2/2006 | Cauthen III et al. |
| 7,033,393 B2 | 4/2006 | Gainor et al. |
| 7,033,395 B2 | 4/2006 | Cauthen |
| 7,041,052 B2 | 5/2006 | Saadat et al. |
| 7,048,754 B2 | 5/2006 | Martin et al. |
| 7,052,516 B2 | 5/2006 | Cauthen et al. |
| 7,128,708 B2 | 10/2006 | Saadat et al. |
| 7,153,312 B1 | 12/2006 | Torrie et al. |
| 7,189,235 B2 | 3/2007 | Cauthen |
| 7,285,124 B2 | 10/2007 | Foerster |
| 7,303,575 B2 | 12/2007 | Ogle |
| 7,326,221 B2 | 2/2008 | Sakamoto et al. |
| 7,329,279 B2 | 2/2008 | Haug et al. |
| 7,335,221 B2 | 2/2008 | Collier et al. |
| 7,347,863 B2 | 3/2008 | Rothe et al. |
| 7,390,332 B2 | 6/2008 | Selvitelli et al. |
| 7,468,074 B2 | 12/2008 | Caborn et al. |
| 7,491,212 B2 | 2/2009 | Sikora et al. |
| 7,494,496 B2 | 2/2009 | Swain et al. |
| 7,601,165 B2 | 10/2009 | Stone |
| 7,615,076 B2 | 11/2009 | Cauthen, III et al. |
| 7,621,925 B2 | 11/2009 | Saadat et al. |
| 7,651,509 B2 | 1/2010 | Bojarski et al. |
| 7,658,750 B2 | 2/2010 | Li |
| 7,666,193 B2 | 2/2010 | Starksen et al. |
| 7,670,379 B2 | 3/2010 | Cauthen |
| 7,670,380 B2 | 3/2010 | Cauthen, III |
| 7,678,135 B2 | 3/2010 | Maahs et al. |
| 7,731,732 B2 | 6/2010 | Ken |
| 7,736,379 B2 | 6/2010 | Ewers et al. |
| 7,749,250 B2 | 7/2010 | Stone et al. |

(56) References Cited

U.S. PATENT DOCUMENTS

| | | | |
|---|---|---|---|
| 7,749,273 B2 | 7/2010 | Cauthen, III et al. |
| 7,753,941 B2 | 7/2010 | Keith et al. |
| 7,776,096 B2 | 8/2010 | Cauthen |
| 7,828,850 B2 | 11/2010 | Cauthen, III et al. |
| 7,846,208 B2 | 12/2010 | Cauthen, III et al. |
| 7,857,830 B2 | 12/2010 | Stone et al. |
| 7,905,904 B2 | 3/2011 | Stone et al. |
| 7,905,923 B2 | 3/2011 | Keith et al. |
| 7,909,851 B2 | 3/2011 | Stone et al. |
| 7,909,879 B2 | 3/2011 | Cauthen |
| 7,922,768 B2 | 4/2011 | Cauthen, III et al. |
| 7,935,147 B2 | 5/2011 | Wales |
| 7,951,201 B2 | 5/2011 | Cauthen et al. |
| 7,959,650 B2 | 6/2011 | Kaiser et al. |
| 7,963,992 B2 | 6/2011 | Cauthen et al. |
| 7,985,257 B2 | 7/2011 | Cauthen et al. |
| 7,993,405 B2 | 8/2011 | Cauthen et al. |
| 7,998,108 B2 | 8/2011 | Nazzaro et al. |
| 8,034,112 B2 | 10/2011 | Cauthen et al. |
| 8,048,160 B2 | 11/2011 | Cauthen |
| 8,083,768 B2 | 12/2011 | Ginn et al. |
| 8,088,130 B2 | 1/2012 | Kaiser et al. |
| 8,088,165 B2 | 1/2012 | Cauthen et al. |
| 8,100,914 B2 | 1/2012 | Cauthen et al. |
| 8,118,836 B2 | 2/2012 | Denham et al. |
| 8,128,640 B2 | 3/2012 | Harris et al. |
| 8,128,658 B2 | 3/2012 | Kaiser et al. |
| 8,128,698 B2 | 3/2012 | Bentley et al. |
| 8,137,382 B2 | 3/2012 | Denham et al. |
| 8,216,253 B2 | 7/2012 | Saadat et al. |
| 8,216,260 B2 | 7/2012 | Lam et al. |
| 8,298,291 B2 | 10/2012 | Ewers et al. |
| 8,814,903 B2 | 8/2014 | Sengun et al. |
| 8,828,053 B2 | 9/2014 | DeMatteo et al. |
| 8,920,436 B2 | 12/2014 | Lam et al. |
| 8,926,634 B2 | 1/2015 | Rothe et al. |
| 9,023,081 B2 | 5/2015 | Maiorino et al. |
| 9,149,266 B2 | 10/2015 | Lamson |
| 2002/0029782 A1 | 3/2002 | Linderoth |
| 2002/0065536 A1 | 5/2002 | Hart et al. |
| 2002/0115999 A1 | 8/2002 | McDevitt et al. |
| 2002/0143359 A1 | 10/2002 | Fulton et al. |
| 2002/0188301 A1 | 12/2002 | Dallara et al. |
| 2003/0060835 A1 | 3/2003 | Wenstrom |
| 2003/0167071 A1 | 9/2003 | Martin et al. |
| 2004/0097980 A1 | 5/2004 | Ferree |
| 2004/0122473 A1 | 6/2004 | Ewers et al. |
| 2004/0153074 A1 | 8/2004 | Bojarski et al. |
| 2004/0162618 A1 | 8/2004 | Mujwid et al. |
| 2004/0225183 A1 | 11/2004 | Michlitsch et al. |
| 2004/0225359 A1 | 11/2004 | Bojarski |
| 2004/0243171 A1 | 12/2004 | Fulton et al. |
| 2005/0080422 A1 | 4/2005 | Otte et al. |
| 2005/0228448 A1 | 10/2005 | Li |
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251202 A1 | 11/2005 | Ewers et al. |
| 2005/0251205 A1* | 11/2005 | Ewers ............... A61B 17/0401 606/232 |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0277966 A1 | 12/2005 | Ewers et al. |
| 2005/0277981 A1 | 12/2005 | Maahs et al. |
| 2005/0283192 A1 | 12/2005 | Torrie et al. |
| 2005/0283246 A1 | 12/2005 | Cauthen, III et al. |
| 2006/0064126 A1 | 3/2006 | Fallin et al. |
| 2006/0178680 A1 | 8/2006 | Nelson et al. |
| 2006/0190042 A1 | 8/2006 | Stone et al. |
| 2006/0259076 A1 | 11/2006 | Burkhart et al. |
| 2006/0265008 A1 | 11/2006 | Maruyama et al. |
| 2006/0271073 A1 | 11/2006 | Lam et al. |
| 2006/0271074 A1 | 11/2006 | Ewers et al. |
| 2007/0010857 A1 | 1/2007 | Sugimoto et al. |
| 2007/0027476 A1 | 2/2007 | Harris et al. |
| 2007/0073320 A1 | 3/2007 | Mikkaichi et al. |
| 2007/0083236 A1 | 4/2007 | Sikora et al. |
| 2007/0100348 A1 | 5/2007 | Cauthen, III et al. |
| 2007/0129804 A1 | 6/2007 | Bentley et al. |
| 2007/0142846 A1 | 6/2007 | Catanese |
| 2007/0156245 A1 | 7/2007 | Cauthen, III et al. |
| 2007/0162054 A1 | 7/2007 | Horaguchi |
| 2007/0162120 A1 | 7/2007 | Bouffier |
| 2007/0185532 A1 | 8/2007 | Stone et al. |
| 2007/0255285 A1 | 11/2007 | Trieu |
| 2007/0276433 A1 | 11/2007 | Huss |
| 2008/0009888 A1 | 1/2008 | Ewers et al. |
| 2008/0015635 A1 | 1/2008 | Olsen et al. |
| 2008/0015636 A1 | 1/2008 | Olsen et al. |
| 2008/0033487 A1 | 2/2008 | Schwartz et al. |
| 2008/0086155 A1 | 4/2008 | Rothe et al. |
| 2008/0097484 A1 | 4/2008 | Lim et al. |
| 2008/0097522 A1 | 4/2008 | Chopra |
| 2008/0140092 A1 | 6/2008 | Stone et al. |
| 2008/0140093 A1 | 6/2008 | Stone et al. |
| 2008/0147086 A1 | 6/2008 | Pfister et al. |
| 2008/0147102 A1 | 6/2008 | Rotella et al. |
| 2008/0167658 A1 | 7/2008 | Kerr et al. |
| 2008/0177302 A1 | 7/2008 | Shumas |
| 2008/0177304 A1 | 7/2008 | Westra et al. |
| 2008/0188893 A1 | 8/2008 | Selvitelli et al. |
| 2008/0195145 A1 | 8/2008 | Bonutti et al. |
| 2008/0200930 A1 | 8/2008 | Saadat et al. |
| 2008/0208225 A1 | 8/2008 | Seibold et al. |
| 2008/0208226 A1 | 8/2008 | Seibold et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0243151 A1 | 10/2008 | Binmoeller |
| 2008/0269781 A1 | 10/2008 | Funamura et al. |
| 2008/0281355 A1 | 11/2008 | Mayer et al. |
| 2008/0294193 A1 | 11/2008 | Schwartz |
| 2008/0312689 A1 | 12/2008 | Denham et al. |
| 2008/0319524 A1 | 12/2008 | Yachia et al. |
| 2009/0018561 A1 | 1/2009 | Schwartz et al. |
| 2009/0030522 A1 | 1/2009 | Cauthen, III et al. |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0062846 A1 | 3/2009 | Ken |
| 2009/0062847 A1 | 3/2009 | Ken |
| 2009/0062848 A1 | 3/2009 | Ken |
| 2009/0062850 A1 | 3/2009 | Ken |
| 2009/0062854 A1* | 3/2009 | Kaiser ............... A61B 17/0401 606/232 |
| 2009/0069823 A1 | 3/2009 | Foerster et al. |
| 2009/0076547 A1 | 3/2009 | Sugimoto et al. |
| 2009/0082805 A1 | 3/2009 | Kaiser et al. |
| 2009/0157184 A1 | 6/2009 | Cauthen, III et al. |
| 2009/0228042 A1 | 9/2009 | Koogle et al. |
| 2009/0259260 A1 | 10/2009 | Bentley et al. |
| 2009/0306711 A1 | 12/2009 | Stone et al. |
| 2010/0049212 A1 | 2/2010 | Caborn et al. |
| 2010/0069923 A1 | 3/2010 | Nguyen et al. |
| 2010/0094337 A1 | 4/2010 | Maiorino |
| 2010/0094425 A1 | 4/2010 | Bentley et al. |
| 2010/0121376 A1 | 5/2010 | Li |
| 2010/0292731 A1 | 11/2010 | Gittings et al. |
| 2011/0022083 A1* | 1/2011 | DiMatteo ........... A61B 17/0401 606/228 |
| 2011/0022084 A1 | 1/2011 | Sengun et al. |
| 2011/0077667 A1 | 3/2011 | Singhatal et al. |
| 2011/0082472 A1 | 4/2011 | Harris et al. |
| 2011/0106151 A1 | 5/2011 | McDevitt et al. |
| 2011/0172701 A1 | 7/2011 | Wales et al. |
| 2011/0270278 A1 | 11/2011 | Overes et al. |
| 2012/0004669 A1 | 1/2012 | Overes et al. |
| 2012/0035654 A1 | 2/2012 | Belson |
| 2012/0046693 A1 | 2/2012 | Denham et al. |
| 2012/0053630 A1 | 3/2012 | Denham et al. |

(56) References Cited

U.S. PATENT DOCUMENTS

| | | | |
|---|---|---|---|
| 2012/0109156 A1 | 5/2012 | Overes et al. |
| 2012/0130422 A1 | 5/2012 | Hootstein |
| 2012/0143215 A1 | 6/2012 | Corrao et al. |
| 2012/0150223 A1 | 6/2012 | Manos et al. |
| 2012/0197271 A1 | 8/2012 | Astorino et al. |
| 2012/0215257 A1 | 8/2012 | Novak |
| 2013/0110165 A1 | 5/2013 | Burkhart et al. |
| 2014/0074157 A1 | 3/2014 | Hendricksen |
| 2014/0243859 A1 | 8/2014 | Robinson |
| 2014/0336703 A1 | 11/2014 | Sengun et al. |
| 2015/0038992 A1 | 2/2015 | DiMatteo et al. |

FOREIGN PATENT DOCUMENTS

| | | |
|---|---|---|
| EP | 0834281 | 4/1998 |
| EP | 0838197 | 4/1998 |
| EP | 1938760 | 7/2008 |
| EP | 1964520 | 9/2008 |
| EP | 2238944 | 10/2010 |
| EP | 2663240 | 11/2013 |
| EP | 2663242 | 11/2013 |
| WO | WO 92/11810 | 7/1992 |
| WO | WO 99/22648 | 5/1999 |
| WO | WO 03/096910 | 11/2003 |
| WO | WO 2004/071307 | 8/2004 |
| WO | WO 2005/011463 | 2/2005 |
| WO | WO 2005/065553 | 7/2005 |
| WO | WO 2006/039296 | 4/2006 |
| WO | WO 2006/117398 | 11/2006 |
| WO | WO 2007/005394 | 1/2007 |
| WO | WO 2008/010738 | 1/2008 |
| WO | WO 2008/048667 | 4/2008 |
| WO | WO 2009/126781 | 10/2009 |
| WO | WO 2009/146402 | 12/2009 |
| WO | WO 2010/088561 | 8/2010 |
| WO | WO 2011/137159 | 11/2011 |
| WO | WO 2012/006161 | 1/2012 |
| WO | WO 2012/096706 | 7/2012 |
| WO | WO 2012/096707 | 7/2012 |

OTHER PUBLICATIONS

U.S. Appl. No. 09/484,706, filed Jan. 18, 2000, Cauthen.
European Search Report for Application No. 10251328.0 dated Oct. 29, 2010.
Brinckmann et al., "A laboratory model of lumbar disc protrusion", Fissure and Fragment Institut fur Experimentelle Biomechanik, Universitat, Munster, German, Spine (Phila., PA 1976) Jan. 15, 1994, 19(2): 228-235.
Maroon et al., "Microdiscectomy versus Chemonucleolysis", Neurosurgery, vol. 16(5), 644-649, May 1985.
Mitek Brochure, Rapid Loc, "Surgical Technique Guide for Repair of Meniscal Tears", 2001, 6 pages.
Biomet Maxfire Technique Guide, Meniscal Repair, 1994, 16 pages.
Cayenne Medical, Crossfix Meniscal Repair System, Surgical Technique Guide, Jul. 2009, 4 pages.
Hoffmann et al., "Arthroscopic shoulder stablilization using Mitek anchors", Knee Surg., Sports Traumatol., Arthroscopy, Mar. 1995, vol. 3, Issue 1, 50-54.
Klinger, "Proceedings of the 1976 Meeting of the Deutsche Gesellschaft fur Neurochirurgica in Berlin", Acta Neurochirurgica, Sep. 1977, vol. 36, Issue 3-4, 265-294.
Mayer et al., "Percutaneous Endoscopic Lumbar Discectomy (PELD)", Neurosurg., Rev., Jun. 1993, 115-120.
Mayer et al., "Endoscopic Discectomy in Pediatric and Juvenile Lumbar Disc Herniation's", Journal of the Pediatric Orthopaedics, Part B, Jan. 1996, 39-43.
Abstracts of the 7th Annual Meeting of the Japanese Society of Micosurgery, Oct. 1980, Niigata, Japan, 8 pages.
Vuono-Hawkins et al., "Mechanical Evaluation of a Canine Intervertebral Disc Spacer: In Situ and In Vivo Studies", Journal of Orthopaedic Research, Jan. 1994, 119-127.

European Patent Application No. 05802651.9: European Search Report, dated Aug. 31, 2009, 7 pages.
International Patent Application No. PCT/US2005/34495: International Search Report, dated Apr. 4, 2007, 2 pages.
Snyder, "Shoulder Arthroscopy: Arthroscopic Treatment of the Acromioclavicular Joint", Chapter 13, 2nd Edition, 2003, 167-183.
U.S. Appl. No. 12/509,112: Non-Final Office Action, dated Jul. 12, 2012, 8 pages.
U.S. Appl. No. 12/509,112: Restriction Requirement, dated Nov. 17, 2011, 8 pages.
U.S. Appl. No. 12/509,112: Restriction Requirement, dated Apr. 10, 2012, 6 pages.
U.S. Appl. No. 13/095,192: Restriction Requirement, dated Sep. 6, 2012, 10 pages.
U.S. Appl. No. 60/113,548, filed Dec. 23, 1998, Schwartz.
U.S. Appl. No. 60/148,913, filed Aug. 13, 1999, Ferree.
U.S. Appl. No. 60/149,490, filed Aug. 18, 1999, Lambrecht.
U.S. Appl. No. 60/154,969, filed Sep. 20, 1999, Matsuura.
U.S. Appl. No. 60/161,085, filed Oct. 25, 1999, Lambrecht.
U.S. Appl. No. 09/453,120, filed Dec. 2, 1999, Torrie.
U.S. Appl. No. 60/263,343, filed Jan. 22, 2001, Keith.
Ahlgren et al., "Anular incision technique on the strength and multidirectional flexibility of the healing intervertebral disc," Spine, Apr. 15, 1994, 19(8), 948-954.
Ahlgren et al., "Effect of anular repair on the healing strength of the intervertebral disc: a sheep model," Spine, Sep. 1, 2000, 25(17), 2165-2170.
Arthrex, Inc., "Arthroscopic Meniscal Repair using the Meniscal Cinch: Surgical Technique," www.arthrex.com, © 2008, 6 pages.
Barrett et al., "T-Fix endoscopic meniscal repair: technique and approach to different types of tears," Arthroscopy: The Journal of Arthroscopic and Related Surgery, Apr. 1995, 11(2), 245-251.
Burg et al., "Modulation of Surface and Bulk Properties of Biomedical Polymers," Annals of the New York Academy of Sciences, Dec. 1997, 831, 217-222.
Caborn, D., "Meniscal Repair with the Fast T-Fix Suture System," Smith & Nephew Technique Plus Illustrated Guide, Mar. 2002, 10 pages.
Cauthen, J., "Annulotomy Study Table", Feb. 8, 1999, 1 page.
Cauthen, J., "Microsurgical Annular Reconstruction (Annuloplasty) Following Lumbar Microdiscectomy: A New Technique," Draft Abstract, Sep. 4, 1998, 4 pages.
Cauthen, J., "Microsurgical Annular Reconstruction (Annuloplasty) Following Lumbar Microdiscectomy: A New Technique," Abstract, AANS CNS Section on Disorders of the Spine and Peripheral Nerves Annual Meeting, 1999, 2 pages.
Cauthen,"Microsurgical Annular Reconstruction (Annuloplasty) Following Lumbar Microdiscectomy: Preliminary Report of a New Technique", CNS Boston Massachusetts, Spine & Peripheral Nerves Section (abstract only), http://abstracts.neurosurgeon.org/view.php?id=2790, accessed Oct. 6, 2010, 1999, 1 page.
Cobey, M., "Arthroplasties using compressed ivalon sponge ("intramedic sponge") long-term follow-up studies in 109 cases," Clinical Orthopaedics and Related Research, Sep.-Oct. 1967, 54, 139-144.
Coen et al., "An anatomic evaluation of T-Fix suture device placement for arthroscopic all-inside meniscal repair," Arthroscopy: The Journal of Arthroscopic and Related Surgery, Apr. 1999, 15(3), 275-280.
Dodge, Jr. et al., "Use of Polyvinyl Sponge in Neurosurgery," Journal of Neurosurgery, May 1954, 11(3), 258-261.
Edgerton et al., "Augmentation Mammaplasty: Psychiatric Implications and Surgical Indications," Plastic & Reconstructive Surgery, Apr. 1958, 21(4), 279-305.
Hampton et al., "Healing Potential of the Anulus Fibrosus," Spine, Apr. 1989, 14(4), 398-401.
International Patent Application No. PCT/US2011/034084: International Search Report and Written Opinion dated Jul. 1, 2011, 5 pages.
International Patent Application No. PCT/US2011/042384: International Search Report and Written Opinion dated Feb. 6, 2012, 26 pages.

(56) References Cited

OTHER PUBLICATIONS

International Patent Application No. PCT/US2011/058065: International Search Report and Written Opinion dated Apr. 5, 2012, 23 pages.

International Patent Application No. PCT/US2011/058071: International Search Report and Written Opinion dated Feb. 6, 2012, 14 pages.

Kambin et al., "Development of degenerative spondylosis of the lumbar spine after partial discectomy. Comparison of laminotomy, discectomy, and posterolateral discectomy," Spine, Mar. 1, 1995, 20(5), 599-607.

Kotilainen et al., "Microsurgical treatment of lumbar disc herniation: Follow-up of 237 patients," Acta Neurochirurgica, 1993, 120(3-4) 143-149.

Kroschwitz, J. I., "Concise Encyclopedia of Polymer Science and Engineering: Vinyl Alcohol Polymers," Wiley & Sons, 1990, 1233-1236.

Kusaka et al., "The Effect of Annulus Fibrosus Perforation on the Intradiscal Matrix Strain of the Axially Loaded Intervertebral Disc," Transactions of the 44th Annual Meeting, Orthopaedic Research Society, Mar. 16-19, 1998, New Orleans, Louisiana, 23(1), p. 190-32 (Abstract).

Lehmann et al., "Refinements in technique for open lumbar discectomy," International Society for the Study of the Lumbar Spine, 1997, 2 pages.

Liu et al., "Morphologic Characterization of Polyvinyl Sponge (Ivalon) Breast Prosthesis," Archives of Pathol. & Lab. Medicine, Sep. 1996, 120(9), 876-878.

Malemud, C. J., "The Role of Growth Factors in Cartilage Metabolism," Rheum. Dis. Clin. North Am., Aug. 1993, 19(3), 569-580.

Ordway et al., "Failure Properties of a Hydrogel Nucleus in the Intervertebral Disc," North American Spine Society, Oct. 22-25, 1997, 168-169.

Osti et al., "1990 Volvo Award in Experimental Studies: Anulus Tears and Intervertebral Disc Degeneration: An Experimental Study Using an Animal Model," Spine, Aug. 1990, 15(8), 762-767.

Osti et al., "Annular Tears and Disc Degeneration in the Lumbar Spine. A post-mortem study of 135 discs," The Journal of Bone and Joint Surgery, Sep. 1992, 74(5), 678-682.

Panjabi et al., "Intrinsic Disc Pressure as a Measure of Integrity of the Lumbar Spine," Spine, Aug. 1988, 13(8), 913-917.

Peters et al., "Ivalon Breast Prostheses: Evaluation 19 Years after Implantation," Plastic and Reconstructive Surgery, Apr. 1981, 67(4), 514-518.

PR Newswire, "Smith & Nephew Launches Fast-Fix™ AB Meniscal Repair System," http://www.prnewswire.com/news-releases/smith—nephew-launches-fast-fixtm-ab-menis . . . , Accessed Aug. 23, 2010, 1 page.

Ray, C. D., "Prosthetic Disc Nucleus Implants: Update," North American Spine Society 13th Annual Meeting, 1999, 252-253.

Sgaglione et al., "All-Inside Meniscal Repair with the ULTRA FAST-FIX™ Meniscal Repair System," Smith & Nephew Knee Series Technique Guide, Feb. 2008, 12 pages.

Silver et al., "Cartilage Wound Healing: An Overview," Otolaryngol. Clin. North Am., Oct. 1995, 28(5), 847-863.

Smith & Nephew Endoscopy, "Endoscopic Meniscal Repair Using the T-Fix™," Smith & Nephew, May 1996, 16 pages.

Smith & Nephew Endoscopy, "Fast-Fix Meniscal Repair System: Technique Information," http://endo.smith-nephew.com/no/node.asp?NodeId=3045, Accessed Apr. 26, 2011, 3 pages.

Southwick et al., "Prosthetic Replacement of Chest-Wall Defects: An Experimental and Clinical Study", A. M. A. Archives of Surgery, 1956, 72, 901-907.

Unipoint Industries, Inc., "Polyvinyl Alcohol Foam for Surgical and Industrial Use: Data Sheets," Jul. 15, 1989, 6 pages.

Urbaniak et al., "Replacement of intervertebral discs in chimpanzees by silicone-dacron implants: a preliminary report," J. Biomed. Mater. Res. Symposium, May 1973, 7(4), 165-186.

Wageck et al., "Arthroscopic meniscal suture with the "double-loop technique"," Arthroscopy: The Journal of Arthroscopic and Related Surgery, Feb. 1997, 13(1), 120-123.

Yasargil, M. G., "Microsurgical Operation of Herniated Lumbar Disc," Advances in Neurosurgery, Lumbar Disc Adult Hydrocephalus, Springer-Verlag, 1977, 4(81), p. 81.

U.S. Appl. No. 61/328,251, filed Apr. 27, 2010, Overes.
U.S. Appl. No. 61/398,699, filed Jun. 29, 2010, Overes et al.
U.S. Appl. No. 61/432,755, filed Jan. 14, 2010, Henrichsen et al.
U.S. Appl. No. 61/443,142, filed Feb. 15, 2011, Henrichsen et al.
U.S. Appl. No. 61/461,490, filed Jan. 18, 2011, Henrichsen et al.
The Free Dictionary, definition of "knot", http://medical-dictionary.thefreedisctionary.com/knot as accessed on Jun. 21, 2016, 5 pages.
Clifford Ashley "The Ashley Book of Knots" 1944.

* cited by examiner

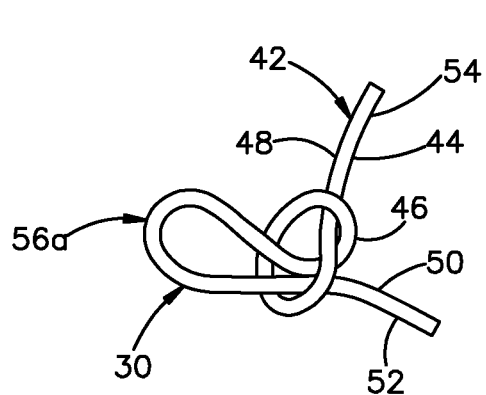
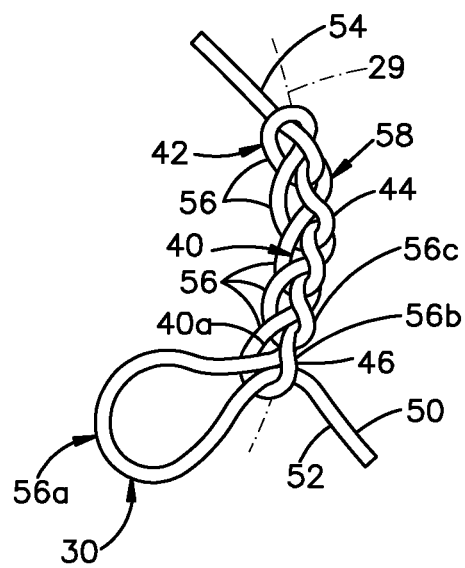
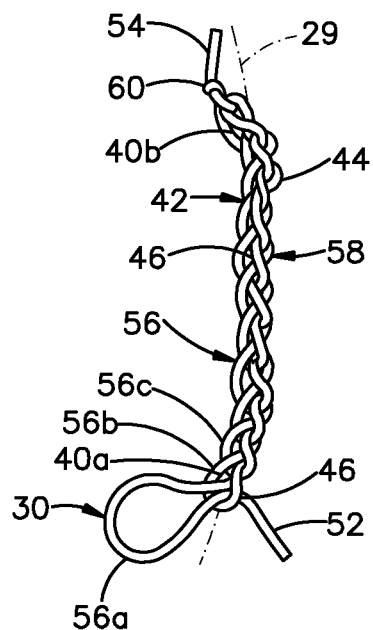
Fig.3A
Fig.3B
Fig.3C

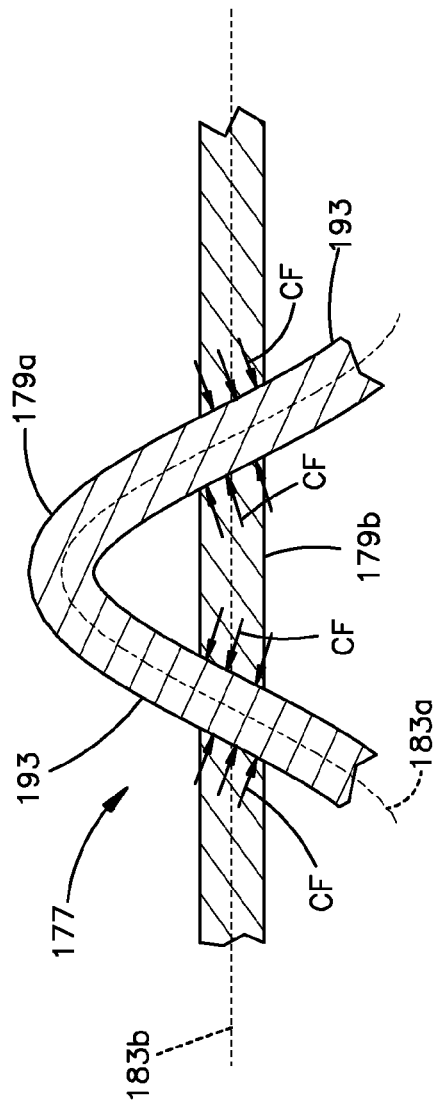
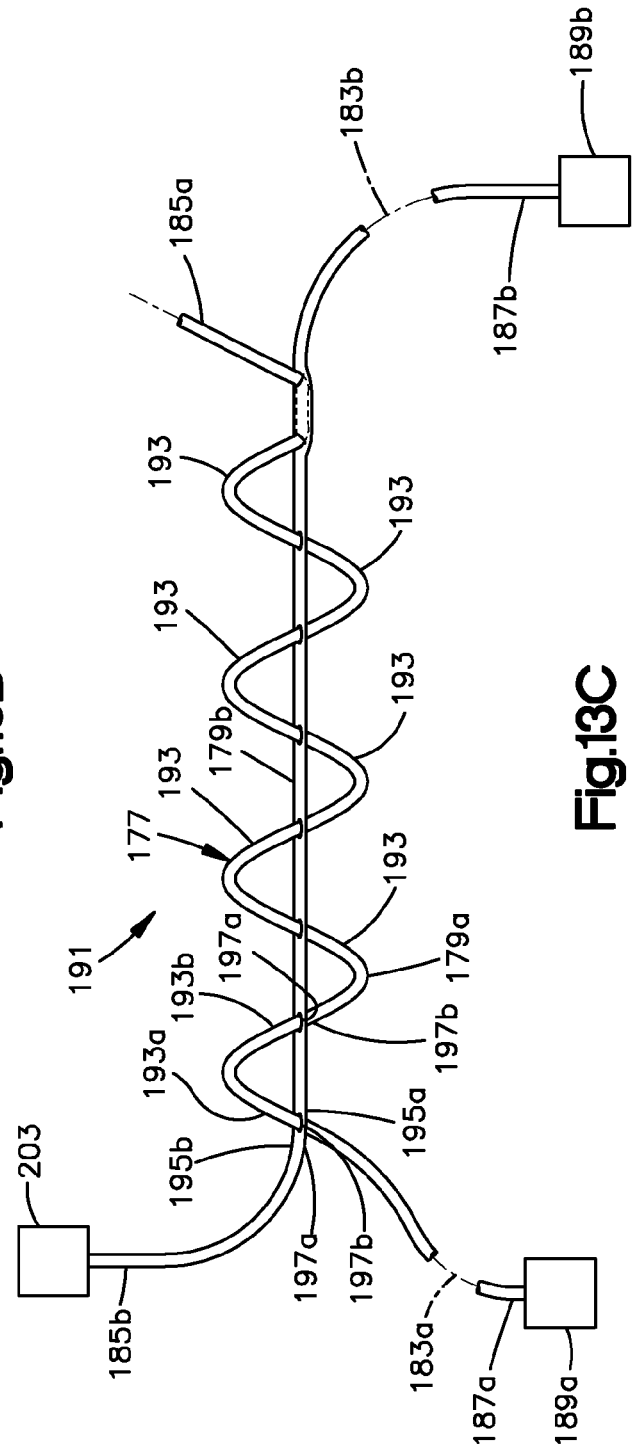
Fig.13B
Fig.13C

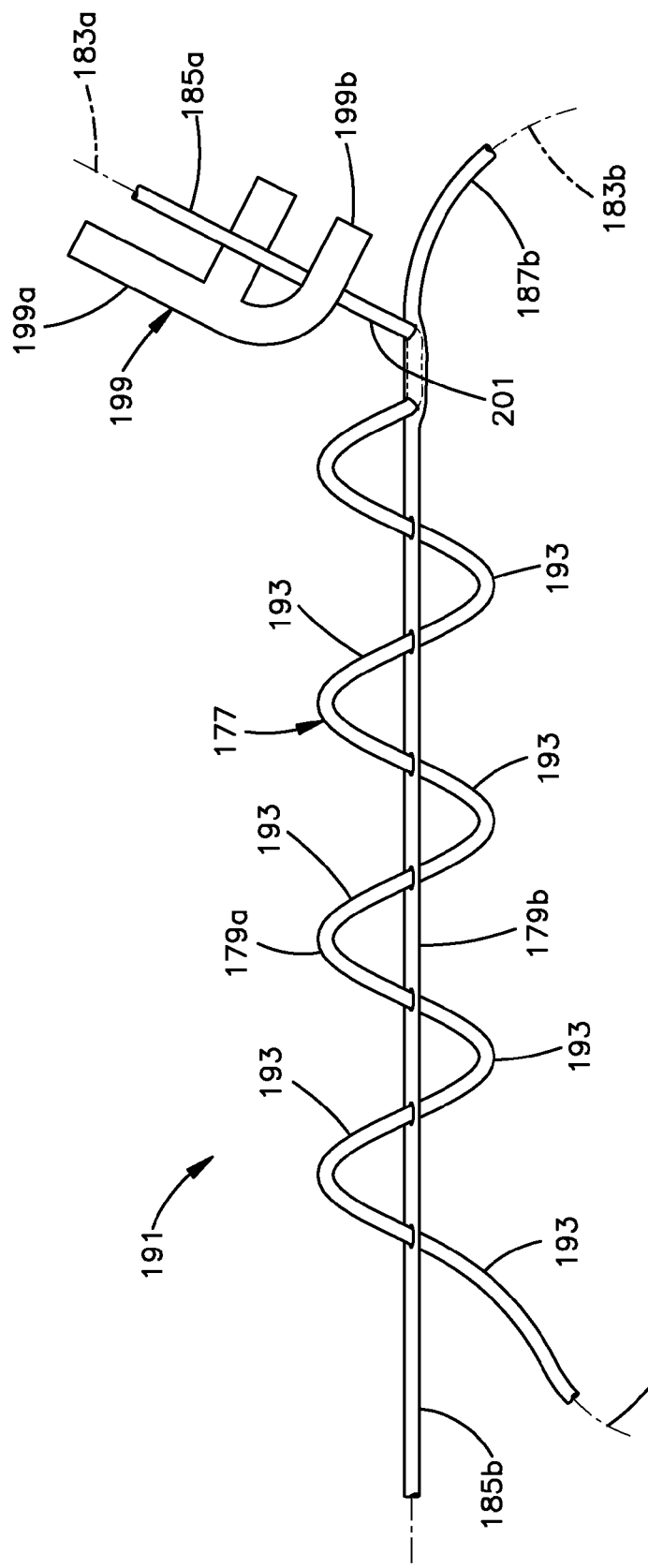

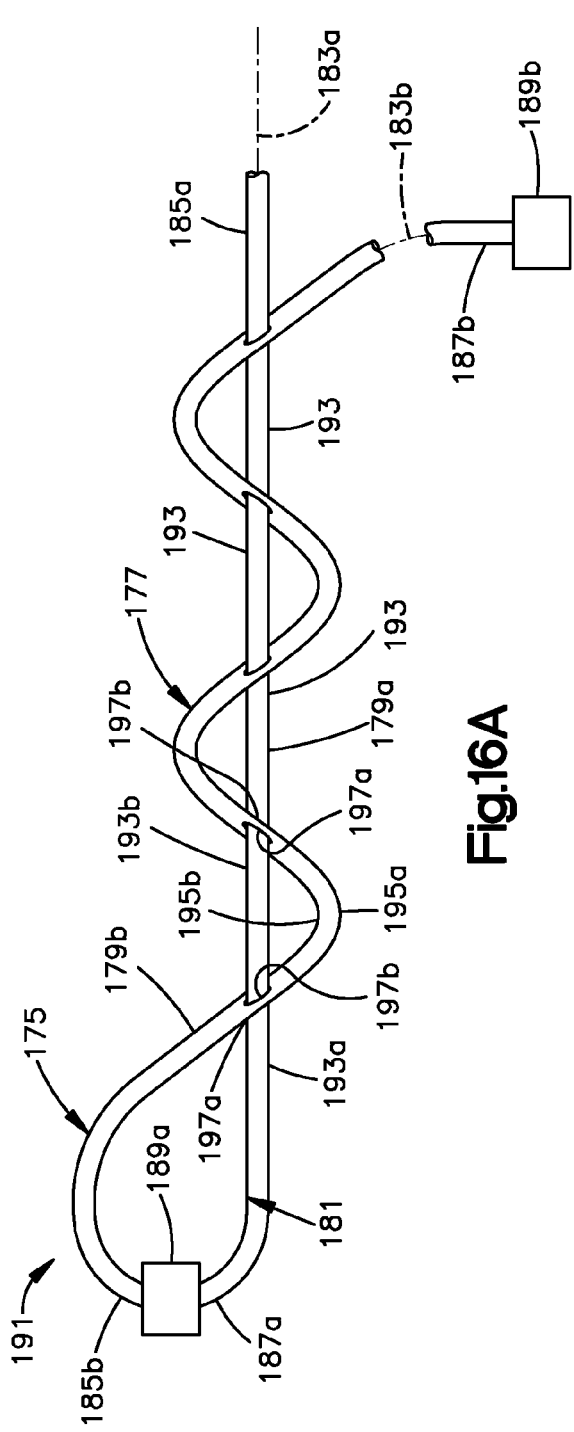
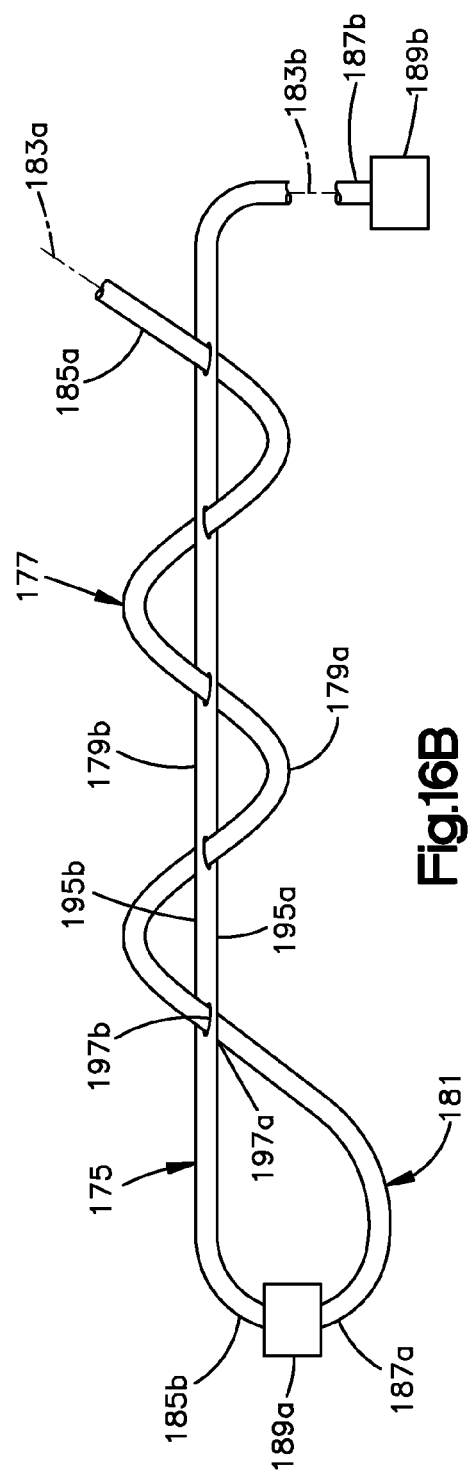
Fig.16A
Fig.16B

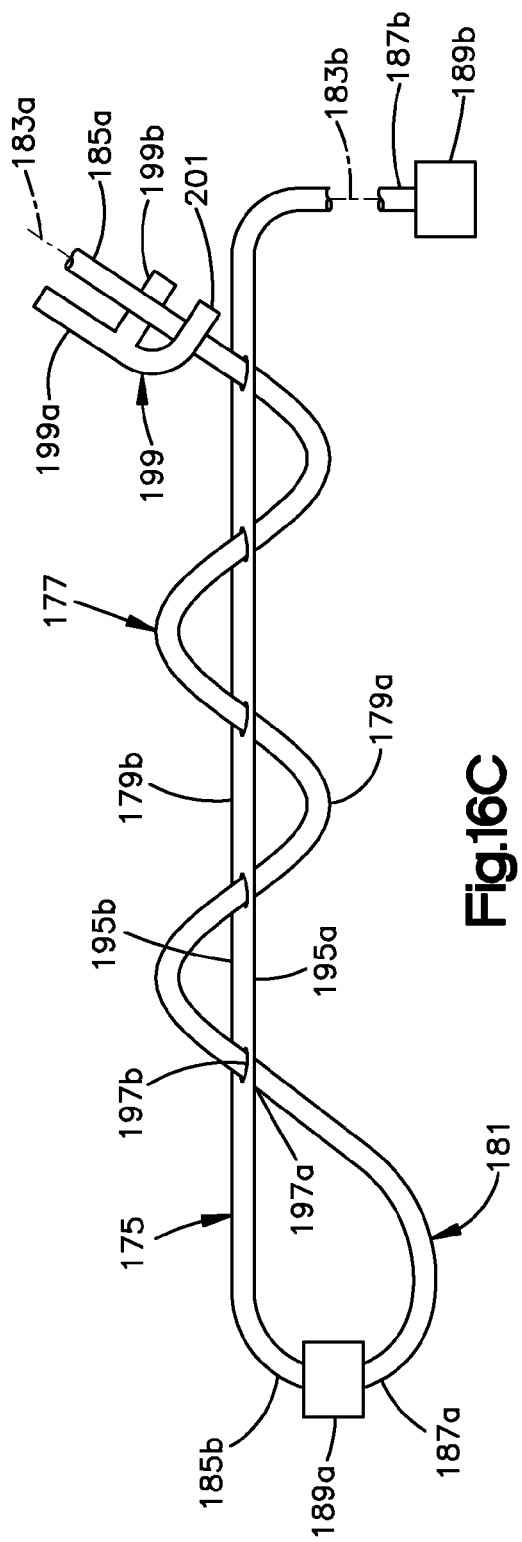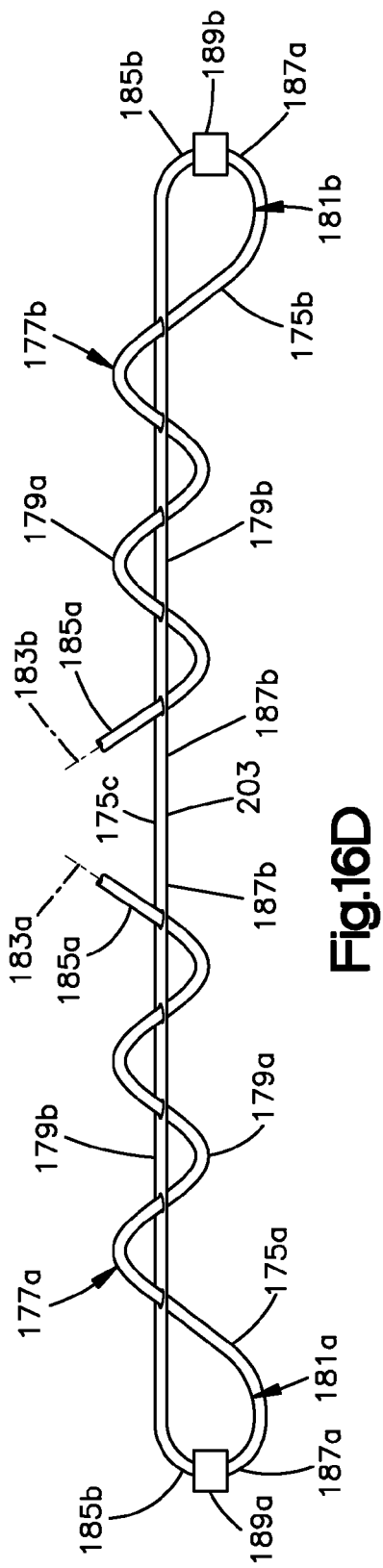
Fig.16C
Fig.16D

STITCH LOCK FOR ATTACHING TWO OR MORE STRUCTURES

CROSS-REFERENCE TO RELATED APPLICATIONS

This application is a continuation-in-part of U.S. patent application Ser. No. 13/172,619, filed Jun. 29, 2011, which is a continuation-in-part of U.S. patent application Ser. No. 13/095,192, filed Apr. 27, 2011. U.S. patent application Ser. No. 13/172,619 further claims the benefit of U.S. Patent Application Ser. No. 61/398,699 filed on Jun. 29, 2010 (Overes, et al.), U.S. Patent Application Ser. No. 61/432,755 filed on Jan. 14, 2011 (Henrichsen, et al.), U.S. Patent Application Ser. No. 61/461,490 filed on Jan. 18, 2011 (Henrichsen, et al.), and U.S. Patent Application Ser. No. 61/443,142 filed on Feb. 15, 2011 (Overes). U.S. patent application Ser. No. 13/095,192 claims the benefit of U.S. Patent Application Ser. No. 61/328,251 filed on Apr. 27, 2010 (Overes), U.S. Patent Application Ser. No. 61/398,699 filed on Jun. 29, 2010 (Overes, et al.), U.S. Patent Application Ser. No. 61/432,755 filed on Jan. 14, 2011 (Henrichsen, et al.), U.S. Patent Application Ser. No. 61/461,490 filed on Jan. 18, 2011 (Henrichsen, et al.), and U.S. Patent Application Ser. No. 61/443,142 filed on Feb. 15, 2011 (Overes). The disclosure of each of the above-identified patent applications is incorporated by reference as if set forth in its entirety herein. The disclosure of co-pending U.S. patent application Ser. No. 13/283,063 filed on Oct. 27, 2011 and entitled "Insertion Instrument for Anchor Assembly" is hereby incorporated by reference as if set forth in its entirety herein. The disclosure of co-pending U.S. patent application Ser. No. 13/283,198 filed on Oct. 27, 2011 and entitled "Method for Approximating a Tissue Defect Using an Anchor Assembly" is hereby incorporated by reference as if set forth in its entirety herein.

BACKGROUND

Orthopaedic surgical procedures often involve the use of a fixation device. Usually an access hole is produced in a bone or soft tissue wherein a suitable fixation device can be fastened. Apart from screws, expandable fixations devices can be used which are inserted into the hole in a collapsed state and transformed into an expanded state once being correctly positioned. The fixation devices can then be biased toward each other so as to approximate the defect. In conventional practice, fixation devices are attached to each other or to other structure by strands that are connected using a pre-tied knot, or a knot that is tied by the surgeon during the surgical procedure, which can be time consuming. In instances where the fixation devices are attached to another structure, such as another fixation device, across a defect, the knot can be subjected to loading during normal anatomical function of the patient. The loading can be static or cyclical, and can degrade the integrity of the knot over time.

In one example orthopaedic surgical procedure, such as a lumbar microdiscectomy, radiculopathy is treated by surgically removing the herniated nucleus pulposus to achieve neural decompression. The lumbar microdiscectomy is one of the most common spinal surgeries performed today. Many patients find relief with this procedure, but for others, the disc could re-herniate through the opening in the annulus resulting in continuing pain and potentially requiring additional surgery. Currently, the standard microdiscectomy technique does not involve closing the annular defect and presents the surgeon with a dilemma. The surgeon may elect to remove the herniated portion of the nucleus impinging on the nerves, which treats radiculopathy, but increases the risk of post-operative rehemiation of the remaining nucleus through the existing defect of the annulus. Alternately, the surgeon may elect to perform extensive debulking, in which most of the remaining nucleus material is removed in addition to the herniated portion to minimize the risk of post-operative reherniation. However, the risk of post-operative disc height collapse and subsequent progression to lower back pain increase.

SUMMARY

In accordance with one embodiment, a stitch lock assembly can include a first strand segment and a second strand segment that are attached to respective first and second structures. The stitch lock can be defined by a region whereby the first strand segment is woven at least into, for instance through, the second strand segment. When the second strand segment is placed in tension at a level greater than a threshold tension level at the stitch lock, the second strand segment applies a compressive force to the first strand segment that prevents the first strand segment from translating relative to the second strand segment at the stitch lock. When the level of tension in the second strand segment (including zero, for instance when the second strand segment is not in tension) is less than the threshold level, the first strand segment is movable with respect to the second strand segment through the stitch lock, thereby biasing at least one or both of the first and second structures to move with respect to the other. For instance, one or both of the first and second structures can be drawn toward the other so as to approximate a defect that is disposed between the first and second structures. In accordance with one embodiment, the first and second strand segments can be defined by separate strands that are fixed to the respective first and second structures. In accordance with another embodiment, the first and second strand segments are integral with each other so as to define at least one loop that is slidably connected to at least a respective one of the first and second structures.

Thus, in accordance with one embodiment, a stitch lock assembly includes a first segment of a strand of suture and a second strand of suture that is elongate along a central axis so as to define a length. The first segment is woven at least into the second segment along a portion of the length of the second segment so as to define a stitch lock having at least two woven segments, for instance at least four woven segments, of the first segment that are woven at least into the second segment. Each of the woven segments are defined at least by an entry location whereby the first segment enters the second segment. The woven segments are configured to translate through the second segment strand when the second segment is in tension at a first level of tension that is less than a threshold level of tension. The second segment applies a compressive force to the first strand when the second segment is in tension at a second level of tension that is at least substantially equal the threshold level of tension so as to prevent the first segment from translating through the second segment.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and instrumentalities shown. In the drawings:

FIGS. 3A-C illustrate method steps for creating an anchor body of an anchor;

FIG. 13B is a sectional side elevation view of a portion of the stitch lock illustrated in FIG. 13A, shown in a locked configuration;

FIG. 13C is a side elevation view of the stitch lock assembly illustrated in FIG. 13A, shown in the locked configuration;

FIG. 13D is a side elevation view of the stitch lock assembly illustrated in FIG. 13C, including a tension relief instrument;

DETAILED DESCRIPTION

Figure 1A:
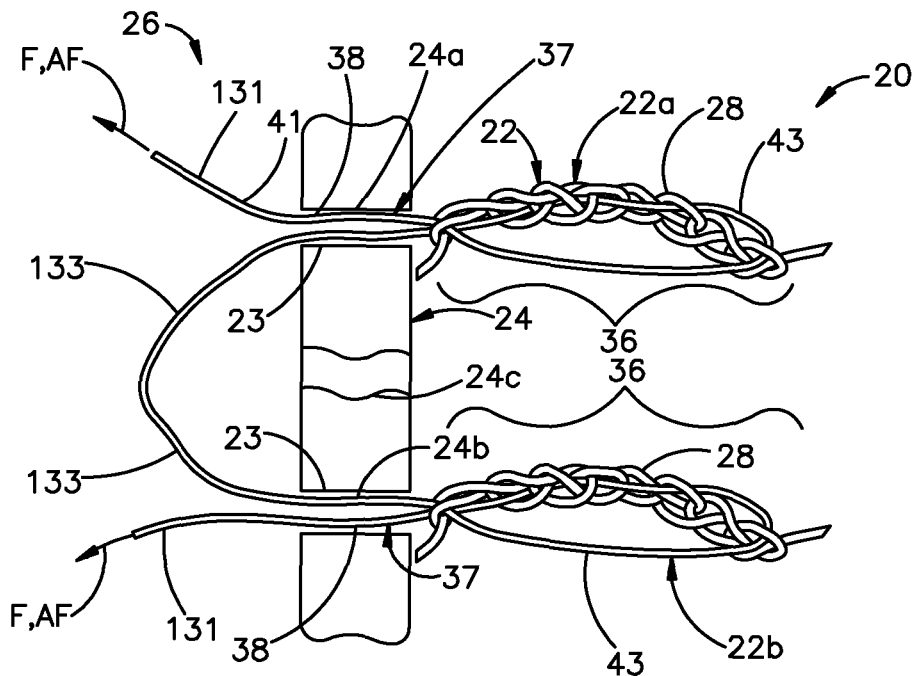
FIG. 1A is a schematic side elevation view of an anchor assembly including a pair of anchor bodies implanted across an anatomical defect and shown in a first configuration.

Referring initially to FIGS. 13A-D and 16A-E, embodiments of a stitch lock 177 are described that are configured to bias at least one of first and second structures 189a-b to move relative to the other structure, for instance toward the other structure. The stitch lock 177 can include a first strand segment 179a that is woven through a second strand segment 179b. When the second strand segment 179b is in tension at a level that is at least equal to a threshold level of tension, the stitch lock 177 assumes a locked configuration, whereby the second strand segment 179b applies a compressive force CF to the first strand segment 179a. The compressive force CF is sufficient to prevent the first strand segment 179a from translating through the second strand segment 179b at the stitch lock 177 when the stitch lock 177 is in a locked configuration. It has been found that while the stitch lock 177 defines a low profile, the stitch lock 177 maintains its structural integrity over time, including instances both whereby the first strand segment 179a is under a constant static load and instances whereby the first strand segment 179a is under a cyclical load. When the second strand segment 179b is in tension at a level that is less than the threshold level of tension, the stitch lock 177 assumes an unlocked configuration, whereby the first strand segment 179a is slidable with respect to the second strand segment. The first and second strand segments 179a-b can be defined by separate strands as illustrated in FIGS. 13A-D, or can be integral with each other and defined by a common strand 175 as illustrated in FIGS. 16A-E.

The first and second strand segments 179a and 179b can be attached to corresponding first and second structures 189a and 189b. The first and second structures 189a and 189b can be configured as any structure as desired. For instance, at least one or both of the structures 189a and 189b can be defined by an anatomical structure, an auxiliary structure (such as a graft, a mesh, a clay, hardware, a bone plate, or any alternative implant structure as desired), or an anchor that is configured to be fixed to a target anatomical location which be defined by the anatomical structure or the auxiliary structure. It is appreciated that conventional surgical procedures involve the use of a large number of anchors, for example toggle anchors and bone anchors (such as screws, pins, nails, rivets, and the like that are configured to be attached to at least one suture strand), and that any suitable anchor can be attached to the first and second strand segments 179a and 179b as described herein. One example of an anchor that is suitable for attachment to the first and second segments 179a and 179b will now be described below with reference to anchors 22, though it should be appreciated that any alternatively constructed anchor capable of attachment to at least one of the first and second strands can be used in combination with the stitch lock 177.

Figure 1B:
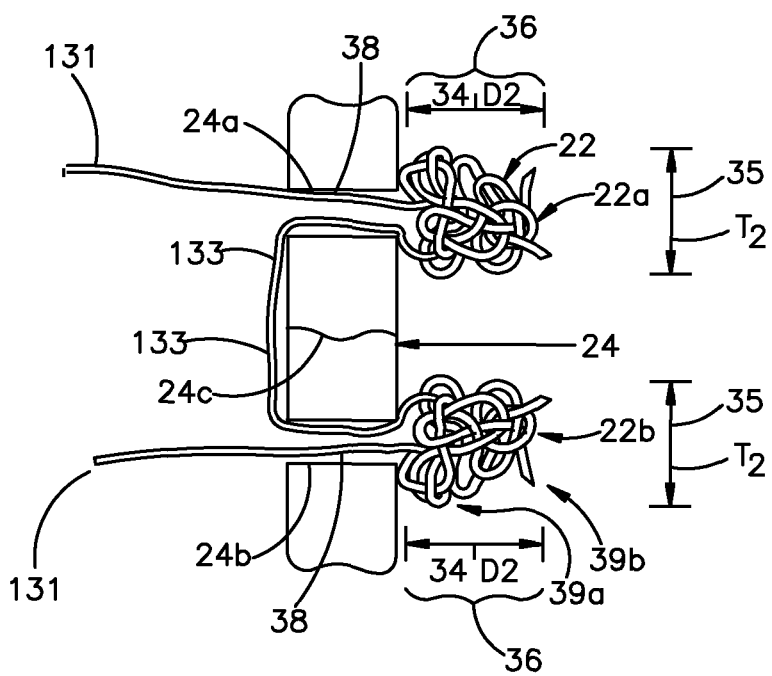
FIG. 1B is a schematic side elevation view of the anchor assembly illustrated in FIG. 1, showing the anchor bodies in an expanded configuration and in an approximated position.

For instance, referring initially to FIGS. 1A-B, an anchor assembly 20 can include at least one expandable anchor 22 such as a plurality of expandable anchors 22 that, in turn, include respective anchor bodies 28 configured to be secured to an anatomical location, which can be defined by at least one anatomical structure 24. In accordance with the illustrated embodiment, the anchor assembly 20 includes a first anchor 22a and a second anchor 22b each configured to be secured to the anatomical location, such as the anatomical structure 24. The anatomical structure 24 can be defined by, for instance, anatomy of a human or other animal, or an implant that is secured or configured to be secured to anatomy of a human or other animal. The anatomy can be defined by tissue that can include at least one of bone and soft tissue such as a tendon, a ligament, cartilage, the annulus of an intervertebral disc, or the like.

In accordance with one embodiment, the at least one anatomical structure 24 can define first and second target anatomical locations 24a and 24b on opposite sides of a gap, such as a gap 24c. Thus, the gap 24c can be disposed in an anatomical structure, and can for instance define an anatomical defect, or can be disposed between different anatomical structure. First and second anchors 22a and 22b can be injected or otherwise driven or inserted into the respective first and second target anatomical locations 24a and 24b on opposite sides of the gap 24c, and subsequently drawn toward each other so as to approximate the gap 24c. Alternatively or additionally still, as described in more detail below with respect to FIGS. 1C-D, the anchor assembly 20 is configured to secure an auxiliary structure 25 to the anatomical structure 24. In this regard, it should be further appreciated that the anchor assembly 20 can include any number of anchors 22 as desired.

Each anchor body 28 can include an expandable portion 36 and an actuation member 37, such as an actuation strand 38, that is configured to actuate the expandable portion 36, and thus the anchor body 28, from a first configuration illustrated in FIG. 1A, whereby the anchor body 28 is initially placed at the target anatomical location, to an expanded configuration illustrated in FIG. 1B, whereby the anchor body 28 can be secured to the anatomical structure 24. Thus, the anchor bodies 28 of the anchors 22a and 22b can be inserted through an opening 23 at the respective target anatomical locations 24a and 24b that can be created, for example, when injecting the anchor bodies 28 to the target anatomical locations 24a and 24b.

Each of the actuation strands 38 of the first and second anchors 22a and 22b can be attached to each other. For instance, the actuation strand 38 of the first anchor 22a can be integral with the actuation strand 38 of the second anchor 22b. Alternatively, as will be described in more detail below, the actuation strand 38 of the first anchor 22a can be separate from the actuation strand 38 of the second anchor 22a, such that the actuation strands 38 of the first and second anchors 22a and 22b are subsequently attached, directly or indirectly, using any suitable connector member 63 (see e.g., FIG. 12C). In accordance with one embodiment, the actuation strands 38 of the each of the first and second anchors 22a and 22b defines at least one actuation portion 131 and can further include at least one attachment portion 133. The actuation portions 131 are each configured to receive an actuation force that causes the respective anchor 22a and 22b to actuate from the first configuration to the expanded configuration.

In accordance with the illustrated embodiment, the attachment portions 133 of the actuation strands 38 of the first and second anchors are configured to be attached to each other. The attachment portions 133 can be integral with each other, or attached to each other using any suitable connector member. Furthermore, in accordance with the illustrated embodiment, the actuation portions 131 can also define attachment portions that are configured to be attached to each other in any suitable manner, either before or after the actuation force F is applied to the actuation portions 131. Thus, the attachment portion 133 of a respective anchor is configured to attach the respective anchor to another anchor, such as an attachment portion 133 of the other anchor. Furthermore, the actuation portion 131 of a respective anchor is configured to attach the respective anchor to another anchor. In accordance with the illustrated embodiment, the attachment portion 133 of the actuation strand 38 of the first anchor 22a is integral with the attachment portion 133 of the actuation strand 38 of the second anchor 22b, though it should be appreciated that the attachment portions 133 of the first and second anchors 22a and 22b can be separate from each other and attached to each other, as described in more detail below.

With continuing reference to FIGS. 1A-B, once the expandable portions 36 of the anchors 22a and 22b have actuated to the expanded configuration, the actuation strands 38 can be placed in tension. For instance, in accordance with one embodiment, an approximation Force AF can be applied to either or both of the actuation portion 131 of the actuation strands 38 of the first and second anchors 22a and 22b, thereby inducing a tension in the actuation strands 38 of the first and second anchors 22a and 22b so as to apply a biasing force that draws the first and second anchors 22a and 22b toward each other. Accordingly, if a gap 24c is disposed between the first and second anchors 22a and 22b, movement of the anchors 22a and 22b toward each other in response to the biasing force approximates the gap 24c which, in certain embodiments, can be an anatomical defect, such as a tissue defect as described above.

Figure 1C:
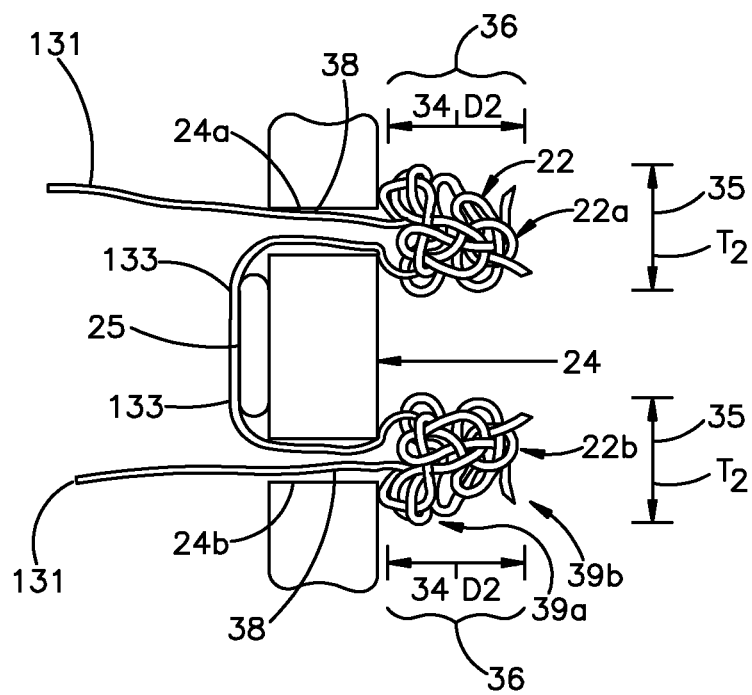
FIG. 1C is a schematic side elevation view of the an anchor assembly illustrated in FIG. 1A, shown secured to an auxiliary structure in accordance with one embodiment.

Alternatively or additionally, as illustrated in FIG. 1C, the anchor assembly 20 is configured to secure an auxiliary structure 25 to the anatomical structure 24 that can define the respective target anatomical locations 24a and 24b. The auxiliary structure 25 can be configured as an anatomical structure, such as tissue as described above or an implant that can be configured as a graft, a mesh, a clay, hardware, a bone plate, or any alternative structure as desired. In this regard, it should be further appreciated that the anchor assembly 20 can include any number of anchors 22 as desired. For instance, the auxiliary structure 25 can be positioned between one or both of the actuation strands 38, and in particular between one or both of the attachment portions 133, and the at least one anatomical structure 24. Accordingly, when tension is induced in the actuation strand 38, and in particular in the attachment portions 133, the auxiliary structure 25 (such as soft tissue) can be drawn toward and secured to the anatomical structure 24 (such as bone), for instance between the actuation strand 38 and the anatomical structure 24 at a location between the first and second target anatomical locations 24a and 24b. In this regard, it should be appreciated that a gap is reduced between the auxiliary structure 25 and the anatomical structure 24. Furthermore, if a gap is disposed between the anchors 22a and 22b, as illustrated in FIGS. 1A-B, tension in the actuation strand 38 can further approximate the gap 24c in addition to securing the auxiliary structure 25 to the anatomical structure 24. Accordingly, unless otherwise indicated, descriptions below of tension in the actuation strand 38 that are configured to approximate the gap 24c is also configured to secure an auxiliary structure between the actuation strand 38 and the at least one anatomical structure 24 that defines the first and second target anatomical locations 24a and 24b.

Figure 1D:
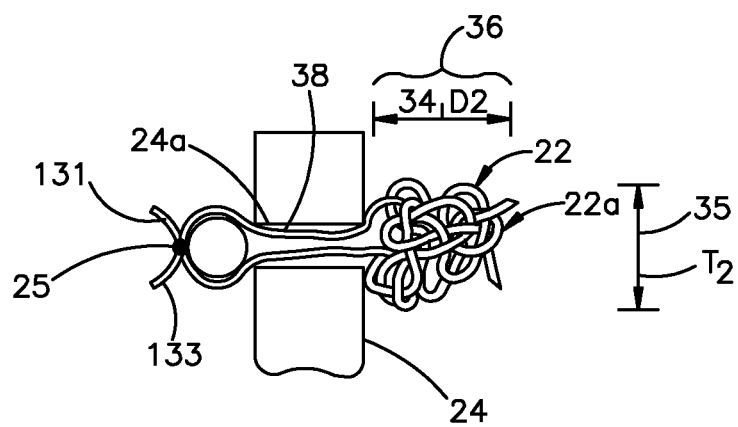
FIG. 1D is a schematic side elevation view of the anchor assembly as illustrated in FIG. 1C, but shown secured to an auxiliary structure in accordance with another embodiment

Alternatively or additionally still, as illustrated in FIG. 1D, the anchor assembly 20 can include at least one anchor 22 that is configured to secure the auxiliary structure 25 between the actuation strand 38 and the anatomical structure 24. For instance, the anchor 22 can be fixed to a target anatomical location 24a of an anatomical structure 24 in the manner described above. The actuation strand 38, such as opposed first and second ends (which can be defined by the actuation portion 131 and the attachment portion 133, respectively) can be tied, stitched, or otherwise secured to another anatomical structure 27, thereby inducing tension in the actuation strand 38 and drawing and securing the auxiliary structure 25 (such as soft tissue) to the anatomical structure 24 (such as bone), for instance between the actuation strand 38 and the anatomical structure 24. In this regard, it should be appreciated that a gap is reduced between the auxiliary structure 25 and the anatomical structure 24. The actuation strand 38 can be separate from and woven through the anchor body 28, for instance as illustrated in FIGS.

Figure 7A:
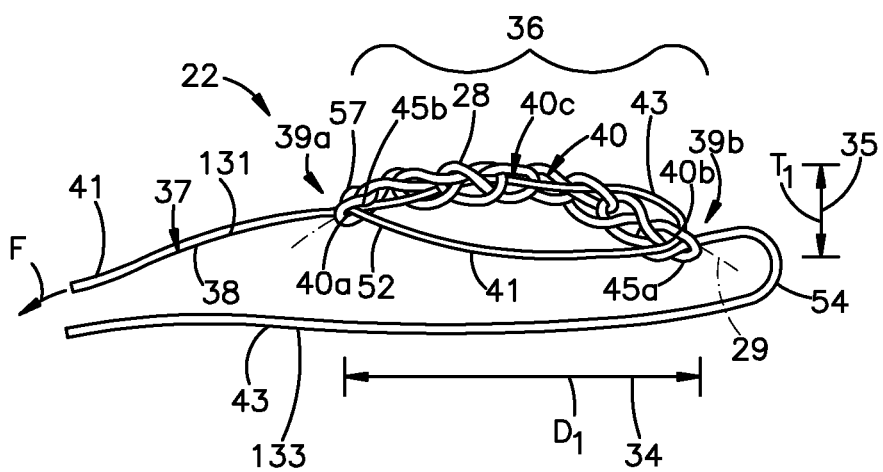
FIG. 7A is a perspective view of an anchor including an actuation strand integral with an anchor body woven through a plurality of openings defined by an expandable portion of the anchor body in accordance with an alternative embodiment, showing the anchor body in a first configuration.

2A-B, or can be integral with the anchor body 28, for instance as illustrated in FIG. 7A.

Furthermore, when the actuation strands 38 are maintained in tension after the defect 24 has been approximated, the anchor bodies 28 are prevented from backing out from the anatomy which could allow the anatomical defect to open. Thus, once the gap 24c has been approximated, the actuation strand 38 of the first anchor 22a can be fixed with respect to the actuation strand 38 of the second anchor 22b so as to maintain tension between the first and second anchors 22a and 22b and prevent the first and second anchors 22a and 22b from separating.

While the first and second anchors 22a and 22b illustrated in FIGS. 1A-B are constructed as described below with reference to FIGS. 2A and 2B, respectively, it should be appreciated that the anchors 22a and 22b can be constructed in accordance with any embodiment described herein or any alternative embodiment as desired. Furthermore, it should be appreciated that while the anchor assembly 20 includes first and second anchors 22a and 22b that are configured to be implanted on opposed sides of the gap 24c, the anchor assembly 20 can include as many anchors 22 as desired that can be attached in a plurality of (e.g., at least two) anchors 22, which can be arranged in individual pairs or otherwise arranged as desired, for instance across the same gap, or anatomical defect, across more than one gap, or disposed on the same side of a gap as desired. Alternatively still, the plurality of anchors 22 can all be attached together, such that select ones of the anchors 22 can be disposed on one side of the anatomical defect and select others of the anchors 22 can be disposed on another side of the anatomical defect, or alternatively disposed across different anatomical defects.

Figure 2A:
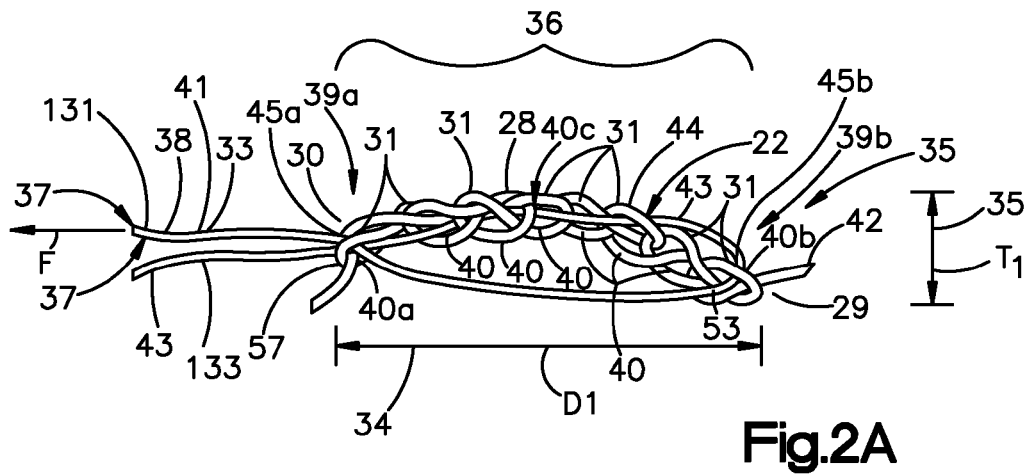
FIG. 2A is a perspective view of an anchor constructed in accordance with one embodiment.
Figure 2B:
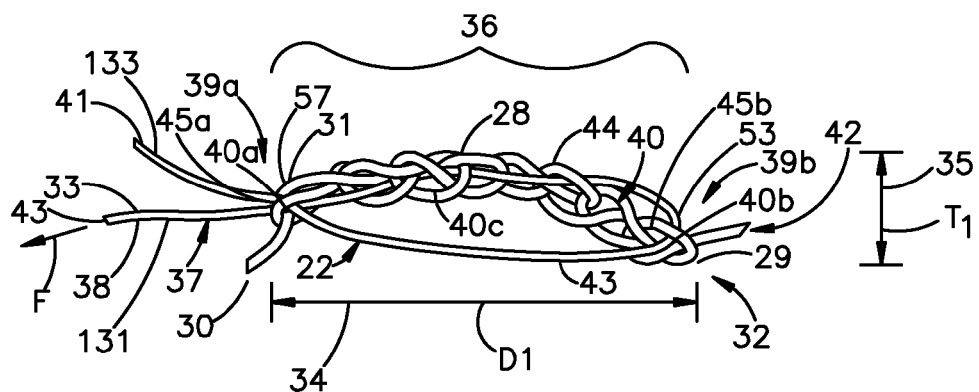
FIG. 2B is a perspective view of an anchor constructed in accordance with another embodiment.

With continuing reference to FIGS. 2A-B, the anchor body 28, and also the expandable portion 36, is elongate along a central axis 29, and defines a first or proximal end 30 and a second or distal end 32 that is spaced from the proximal end 30 substantially along the central axis 29. The central axis 29 can define any shape, or portions having any shape as desired. For instance, the central axis 29, or portions of the central axis 29, can be linear, substantially linear, nonlinear, including regularly, irregularly, otherwise curved, or can be otherwise shaped as desired. Accordingly, the anchor body 28 can define a direction of elongation 34 that extends linearly between the first and second ends 30 and 32. It should be appreciated, for instance when the central axis 29 is substantially straight, that the direction of elongation 34 can be substantially coincident with the central axis 29. It should be further appreciated, for instance when the central axis 29 is nonlinear that the direction of elongation 34 at least partially or substantially entirely spaced from the central axis 29. The anchor body 28 further defines an expandable portion 36 that has a first or proximal end 39a and a second or distal end 39b. The proximal end 39a of the expandable portion 36 can be coincident with or different than (for instance recessed with respect to) the proximal end 30 of the anchor body 28, and the distal end 39b of the expandable portion 36 can be coincident or different than (for instance recessed with respect to) the distal end 32 of the anchor body 28.

The anchor 22 further includes an actuation member 37 that can be configured as an actuation strand 38 that can actuate the expandable portion 36, and thus the anchor body 28, from the first configuration illustrated in FIG. 1A to the expanded configuration illustrated in FIG. 1B. The actuation strand 38 can be provided as a suture or any alternatively constructed strand as desired. The expandable portion 36 of the anchor body 28 extends along the direction of elongation 34 so as to define an initial distance D1 as measured from the proximal end 39a to the distal end 39b along the direction of elongation 34 when in the first configuration. The initial distance D1 can be any length as desired, such within a range having a lower end that can be defined by approximately 5 mm, alternatively approximately 10 mm, alternatively still approximately 20 mm, and alternatively still approximately 24.5 mm, and having an upper end that can be defined by approximately 50 mm, alternatively approximately 40 mm, alternatively still approximately 30 mm, and alternatively still approximately 25.5 mm.

Furthermore, when in the first configuration, the expandable portion 36 defines an initial maximum thickness T1 that extends in a second direction 35 that is substantially perpendicular, with respect to the direction of elongation 34. The initial maximum thickness T1 can be sized as desired. As illustrated in FIG. 1B, when the expandable portion 36 in the expanded configuration, the expandable portion 36 is collapsed, for instance compressed or tangled, along the direction of elongation 34 to a second distance D2 as measured from the proximal end 39a to the distal end 39b along the direction of elongation 34. The second distance D2 can be less than the initial distance D1. As the expandable portion 36 collapses along the direction of elongation, for instance as it is actuated from the first configuration to the expanded configuration, the expandable portion 36 expands along the second direction 35 to a second maximum thickness T2 that is greater than the initial maximum thickness T1. The second maximum thickness T2 extends along the second direction 35 which is substantially perpendicular to the direction of elongation 34.

The maximum thicknesses T1 and T2 in the second direction 35 can be defined such that the anchor body 28 does not define a thickness in the second direction 35 that is greater than the maximum thicknesses T1 and T2, respectively. It should be appreciated that the proximal and distal ends 39a and 39b can change locations on the expandable portion 36 as the expandable portion 36 actuates to the expanded configuration, for instance due to configuration of the expandable portion 36 when in the expanded configuration. However, when the expandable portion 36 is in the expanded configuration, the proximal and distal ends 39a and 39b continue to define the proximal-most and distal-most ends of the expandable portion 36, such that the distance D2 along the direction of elongation 34 is defined linearly between the proximal and distal ends 39a and 39b of the expandable portion 36 when the expandable portion 36 is in the expanded configuration.

The expandable portion 36 can define a plurality of loops 31 that define respective openings 40 (such as at least two openings 40) that extend through the expandable portion 36 along the second direction 35. For instance, the loops 31 can be constructed as described below with respect to the loops 56 as illustrated in FIGS. 3A-C, the loops 99 illustrated in FIGS. 10A-H, or any suitable alternatively constructed loops. The expandable portion 36 can include any number of loops 31, for instance eight loops, more than eight loops, or less than eight loops. The openings 40 are spaced substantially along the central axis 29, and thus are also spaced substantially along the direction of elongation 34. For instance, the openings 40 are spaced along a direction having a component along the direction of elongation 34. Thus, the openings 40 can be spaced both along the direction of elongation 34 and along the second direction 35.

The openings 40 can define a proximal-most opening 40a, and distal-most opening 40b, and at least one intermediate opening 40c such as a plurality of intermediate openings 40c disposed between the proximal-most opening 40a and the distal-most opening 40b. The expandable portion 36 can be disposed between and including the loops 31 that define the proximal and distal openings 40a and 40b. The actuation strand 38 is configured to be woven through at least one of the openings 40, including a plurality of the openings 40 (for instance at least two up to all of the openings 40). Accordingly, when an actuation force F is applied to the actuation strand 38 substantially along the direction of elongation 34, the actuation strand 38 can bias the expandable portion 36, and thus the anchor body 28, to collapse along the direction of elongation 34 and expand along the second direction 35, thereby expanding the anchor from the first configuration to the expanded configuration. The force F can be a tensile force, including a pure tensile force or a force that can be offset from a pure tensile force but has a component that is a pure tensile force. It should thus be appreciated that the force F can be applied to the respective actuation strand 38 substantially along the direction of elongation 24, such that the force F can have a directional component that is parallel to or coincident with the direction of elongation 24, or can be entirely parallel to or coincident with the direction of elongation 24.

It should be appreciated that when the expandable portion 36 is in the first configuration, at least one of the openings 40 up to all of the openings 40 can define a first maximum dimension between the proximal and distal ends of the respective loops 31, and a second maximum dimension between opposed sides of the respective loops 31 that extend between the proximal and distal ends of the respective loops 31. The ratio of the second dimension to the first dimension of at least one of the loops 40 up to all of the loops 40 can increase when the expandable portion 36 expands from the first configuration to the expanded configuration. Furthermore, when the expandable portion is in the expanded configuration, a plurality of the loops 31, such as the opposed sides of the loops 31, can overlap along the second direction 35 an amount greater than when the expandable portion 36 is in the first configuration. In accordance with one embodiment, the opposed sides of the loops 31 do not overlap along the second direction 35, or can overlap slightly along the second direction 35 depending on the amount of tension induced in the expandable portion 36.

Referring now to FIGS. 3A-C, the anchor body 22 can be in the form of a substrate 42, which in one embodiment can be a strand, such as a suture strand or any alternatively constructed strand, that defines an anchor body strand 44. The anchor body strand 44, along with the other components of the anchor assembly 20, can be resorbable as desired. The anchor body strand 44 can have any suitable USP (United States Pharmacopia) size (or diameter) as desired, for instance between and including USP 7-0 and USP 5, such as between and including USP 2-0 and USP 5, for instance USP 2. The anchor body strand 44 can be woven and porous so as to defining openings, or can be nonwoven and devoid of openings as desired. Whether the anchor body strand 44 is woven or nonwoven, the anchor body strand 44 can be braided as desired so as to define the openings 40. One method of constructing the anchor body 22, and thus the expandable portion 36, from the anchor body strand 44 includes the step of tying a first stopper knot 46, which can define a proximal stopper knot 46 of the anchor body 28, having a post end 48 and a free end 50.

The anchor body strand 44 defines a first end portion 52, such as a proximal end portion, that defines the free end 50 of the first stopper knot 46, and a second end portion 54, such as a distal end portion, that defines the post end 48 of the proximal stopper knot 46. The method further includes the step of looping the first end portion 52 at a location adjacent the first stopper knot 46 so as to form a first proximal loop 56a, which can be a terminal loop disposed at the proximal end 30. The first proximal loop 56a is passed through the stopper knot 46 such that the first end portion 52 extends from the first proximal loop 56a through the stopper knot 46. The first end portion 52 can be further drawn through the first proximal loop 56a and tightened so as to define a proximal-most loop 57 of the loops 31 of the anchor body 28 as illustrated in FIGS. 2A-B. The first end portion 52 of the anchor body strand 44 can be cut or tied in a simple knot if desired at a location proximate to the proximal-most loop 57 of the loops 31, and thus proximate to the proximal ends 30 and 39a, and singed as desired so as to maintain structural integrity of the anchor strand 44 during use. Thus, the first end portion 52 can define the free end of the proximal-most loop 57 of the loops 31 of the anchor body 28.

The method further includes the step of braiding the second end portion 54 distally so as to define a plurality of similarly constructed loops 56 of the expandable portion 36 that are spaced substantially along the central axis 29. The loops 56 define respective ones of the plurality of openings 40. For instance, the method can further include the step of looping the second end portion 54 so as to form a new loop, such as a second distal loop 56b, adjacent a prior loop, such as the first proximal loop 56a, and passing the second distal loop 56b through the first proximal loop 56a The step of braiding can further include additional steps of creating a new loop, which can be a third distal loop 56c, from the second end portion 54 such that a prior loop, such as the second loop 56b, is disposed proximal with respect to the additional distal loop 56c. The additional distal loop 56c is disposed immediately adjacent the prior loop 56b, and the method further includes the step of passing the additional distal loop 56c through the immediately proximal loop 56b.

The method further includes the steps of creating additional distal loops from the second end portion 54 as desired, and passing each of the additional new distal loops 56 through the respective prior loop to creating another new distal loop. Additional new distal loops 56 can be created as desired until a braid 58 of a desired length and a desired number of loops 56 has been created. Once the braid 58 has reached the desired length, the second end portion 54 can be knotted or otherwise terminated at a location distal of the distal-most loop 56 so as to define a second stopper knot 60, which can define the distal stopper knot of the anchor body 28. The second end portion 54 can be cut or tied into a simple knot if desired at a location proximate to the second stopper knot 60, and singed so as to maintain structural integrity during use. Thus, the second end portion 54 defines the free end of the second stopper knot 60.

It should be appreciated that while the loops 56 of the expandable portion 36 can be constructed from the same anchor body strand 44 as illustrated in FIGS. 3A-C, and thus are integral with each other in accordance with the illustrated embodiment, the expandable portion 36 can alternatively include two or more anchor strands 55 that alone and/or in combination define braided segments or loops 56 that can be joined, for instance welded (as described in more detail below with respect to FIG. 5C), stitched (as described in more detail below with respect to FIG. 5D), tied, spliced, or otherwise attached. It should be further appreciated that the anchor body strand 44 can alternatively be braided in any alternative manner as desired so as to define the anchor body 28 having an expandable portion 36 that is configured to be actuated from the first configuration to the expanded configuration as described herein.

The actuation strand 38 can be separate or non-integral from the expandable portion 36, and thus anchor body 28, and attached to the expandable portion 36 as illustrated in FIGS. 1A-B and 2A-B in any manner as desired such that the actuation force F applied to the actuation strand 38 causes the anchor body 28 to actuate from the first configuration to the expanded configuration. The actuation strand 38 can have any suitable USP (United States Pharmacopia) size (or diameter) as desired, for instance between and including USP 7-0 and USP 5, such as between and including USP 2-0 and USP 5. For instance, as illustrated in FIG. 2A, the anchor 22 can include an auxiliary strand 33 that is separate or non-integral from the substrate 42 of the actuation body 28, and attached to the substrate 42. The auxiliary strand 33 can be woven, and thus extend, through a pair of the openings 40, such as a first or proximal select opening 45a and a second or distal select opening 45b that is disposed distal with respect to the first select opening 45a. The anchor auxiliary strand 33 can define an actuation strand 38 that is configured to actuate the anchor 22 between the first configuration and the expanded configuration. In accordance with the illustrated embodiment, the first select opening 45a is the proximal-most opening 40a and the second select opening 45b is the distal-most opening 40b, though it should be appreciated that either or both of the first and select openings 45a and 45b can be selected from the intermediate openings 40c. The actuation strand 38 can define a first portion 41 that can define an actuation portion that extends out, for instance proximally out, from the anchor body 28 at a location proximal with respect to the openings 40 that receive the actuation strand 38. The first portion 41 can further extend and out the anatomical location 24, and is configured to receive the actuation force F. In accordance with some embodiments, the first portion 41 can furthermore define a terminal end of the actuation strand 38. The actuation strand 38 can extend distally from the first portion 41.

Several embodiments are described herein with reference to first and second select openings 45a and 45b. It should be appreciated that the reference numbers "45a" and "45b" are used to conceptually identify first and select openings with respect to the various embodiments that identify first and second select openings. The particular ones of the openings 40 that define the particular first and select openings 45a and 45b do not necessarily coincide from embodiment to embodiment, and can in fact vary from embodiment to embodiment as desired.

The actuation strand 38 can be further looped through the second select opening 45b so as to define first and second portions that define the first portion 41 and a second portion 43 that can define a looped portion that extends proximally out the anatomical structure 24 and is opposite the first portion 41. As will be described in more detail below, in accordance with certain embodiments, the actuation force F can be applied to the actuation strand 38, for instance to at least one or both of the first portion 41 and the second portion 43, so as to actuate the expandable portion 36 from the first configuration to the expanded configuration. In accordance with the illustrated embodiment, the second portion 43 can be woven through, and thus extend through, at least one of the openings 40 such as a plurality of select openings 40 that can be disposed between the first and second select openings 45a and 45b, such that the actuation strand 38 defines a loop 53. For instance, the second portion 43 of the actuation strand 38 can be woven through a plurality of the intermediate openings 40c, and further woven through the first select opening 45a, which can be the proximal-most opening 40a. The first and second portions 41 and 43 can extend proximally from the anchor body and out the anatomy, such that the actuation force F can be applied to the first portion 41, the second portion 43 can attach to the actuation strand of a second anchor. Thus, in accordance with the illustrated embodiment, the first portion 41 defines an actuation portion 131 of the actuation strand 38, and the second portion 43 defines an attachment portion 133 of the actuation strand 38. Alternatively, as illustrated in FIG. 2B, the second portion 43 can receive the actuation force F and the first portion 41 can attach to the actuation strand of a second anchor. Thus, the second portion 43 can define the actuation portion 131 of the actuation strand 38 and the first portion 41 can define the attachment portion 133 of the actuation strand 38.

As described above with respect to FIGS. 1A-B, the actuation strand 38 can be integral with the actuation strand of the second anchor. Alternatively, the actuation strands 38 can be attached in any manner as desired. For instance, one or both of the actuation strands 38 can be woven through the other so as to attach the actuation strands 38, as described below with reference to FIG. 17C.

During operation, with continuing reference to FIG. 2A, when the actuation force F is applied to the actuation strand 38 and in particular to the first portion 41 of the actuation strand 38 when the proximal end 39a of the expandable portion 36 is braced and the second portion 43 of the actuation strand 38 is in tension, the distal end 39b of the expandable portion 36 is drawn toward the proximal end 39a of the expandable portion 36 as the size of the loop 53 decreases. The proximal end 39 can be braced for instance by the anatomical structure 24 or a bracing tool, or can alternatively be braced when the proximal end 30 of the anchor body 28 is braced, for instance by the anatomical structure 24 or a bracing tool. Accordingly, the expandable portion 36 expands from the first configuration to the expanded configuration. In accordance with the illustrated embodiment, as the distal end 39b is drawn toward the proximal end 39a, the expandable portion 36 can define a substantial u-shape.

Referring also to FIGS. 1A-B, as the actuation force F continues to be applied to the first portion 41, the auxiliary strand 38 is translated through the anchor body 28, thereby reducing slack in the second portion 43 and eventually inducing tension in the second portion 43. Once the second portion 43 is under tension, further application of the actuation force F to the first portion 41 causes the loop 53 to decrease in size, which thereby causes the expandable portion 36 to slide along the second portion 43 of the actuation strand 38, thereby drawing the distal end 39b further toward the proximal end 39a along the actuation strand 38, and causing the expandable portion 36 to become tangled or otherwise collapsed as it remains in the expanded configuration. It should be appreciated that additional tension induced in the second portion 43 of the actuation strand, or the end of the actuation strand 38 that is attached to the second anchor, can bias the anchor 22 toward the second anchor, thereby approximating the gap 24c as described above.

When the anchor 22 illustrated in FIG. 2A defines the first anchor 22a illustrated in FIGS. 1A-B and the anchor 22 illustrated in FIG. 2B defines the second anchor 22b illustrated in FIGS. 1A-B, first portion 41 of the actuation strand 38 of the first anchor 22a receives the actuation force F, and the second portion 43 of the actuation strand 38 of the second anchor 22b can receive the actuation force F. The second portion 43 of the actuation strand 38 of the first anchor 22a can be attached to the first portion 41 of the actuation strand 38 of the second anchor 22b. Thus, tension induced in the actuation strands 38 of the first and second anchors 22a and 22b due to the application of the actuation force to the actuation strands 38 causes the first and second anchors 22a and 22b to actuate from the first configuration to the expanded configuration. As described in more detail below, it should be appreciated that either or both of first and second portions 41 and 43 of the actuation strand 38 of the first anchor 22a can receive the actuation force F, either or both of the first and second portions 41 and 43 of the actuation strand 38 of the first anchor 22a can be attached to the actuation strand 38 of the second anchor 22b (either integrally or separately attached), either or both of first and second portions 41 and 43 of the actuation strand 38 of the second anchor 22b can receive the actuation force F, and either or both of the first and second portions 41 and 43 of the actuation strand 38 of the second anchor 22b can be attached to the actuation strand 38 of the first anchor 22a (either integrally or separately attached).

It should further be appreciated that actuation of the first and second anchors 22a and 22b can occur independent of tension that is induced in the actuation strands 38 across the gap 24c. For instance, one of the anchors 22a and 22b can be actuated to its expanded configuration, and the other of the anchors 22a and 22b can be actuated to its expanded configuration. Continued application of force to the actuation portion 131 of either or both of the actuation strands 38 can induce tension in the attachment portion 133 of the actuation strands 38 when the attached portions 133 of the actuation strands 38 are attached to each other.

Figure 2C:
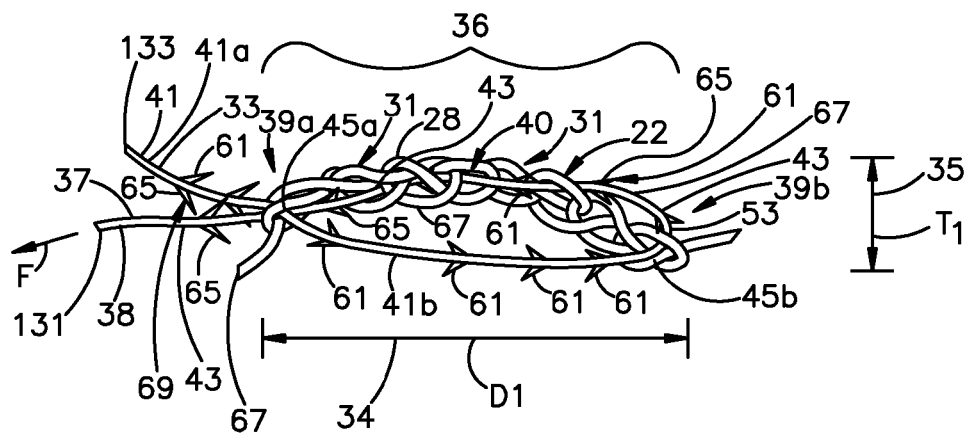
FIG. 2C is a perspective view of an anchor constructed in accordance with another embodiment.

Referring now to FIG. 2C, it should be appreciated that the actuation strand 38 can be barbed so as to facilitate movement of the actuation strand 38 through the openings 40 along an actuation direction that causes the expandable portion 36 to actuate from the first configuration to the expanded configuration. Thus, the actuation strand 38 can define a ratchet that allows for unidirectional movement of the actuation strand through the expandable portion 36 along the actuation direction, but prevents or limits movement of the actuation strand 38 along a direction that is opposite the actuation direction.

The actuation strand 38 can comprise a monofilament, and in one embodiment can be a quill suture. The actuation portion 131 of the actuation strand 38, which can be the second portion 43 as illustrated, can include a first at least one barb 61, such as a first plurality of barbs 61, that each define a leading end 65 that defines a cam so as to facilitate movement of the actuation strand 38 in the direction of the leading ends 65 (e.g., the actuation direction). Each of the barbs 61 can further define a trailing end 67 that defines a catch so as to prevent movement of the actuation strand 38 through the openings 40 along a direction opposite the actuation direction.

The attachment portion 133 of the actuation strand 38, which can be the first portion 41 as illustrated, includes first portion 41a that is configured to remain external to the expandable portion 36 both prior to and during actuation of the expandable portion 36 from the first configuration to the expanded configuration. The first portion 41a of the first portion 43 can include a second at least one barb 69, such as a second plurality of barbs 69, that each defines a leading end 65 that is oriented opposite the leading end 65 of each of the first plurality of barbs 61. Each of the second plurality of barbs 69 can further define a trailing end 67 that are oriented opposite the trailing ends 67 of the first plurality of barbs 61. Accordingly, the trailing ends 67 of the first and second barbs 61 and 69, respectively, face each other. The trailing end 67 of each of the second barbs 69 can define an engagement member that is configured to catch the anchor body strand 44 so as to prevent movement of the actuation strand 38 through the openings 40 as the actuation strand 38 travels along the actuation direction. The attachment portion 133 of the actuation strand 38, which can be the first portion 41 as illustrated, further includes a second portion that is disposed distal of the first select opening 45a and can also carry a plurality of the first barbs 61.

Accordingly, during operation, when the actuation force F is applied to the actuation portion 131 of the actuation strand 38, such as the second portion 43, the actuation strand 38 travels through the openings 40. Each of the first plurality of barbs 61 is oriented so as to define a ratchet that permits movement of the actuation strand 38 through the openings 40 along a direction that actuates the expandable portion 36 from the first configuration to the expanded configuration. The actuation strand 38 translates through the openings 40 until the trailing end 67 of one of the second barbs 69 catches the anchor body strand 44 at a location proximate to the first select opening 45a, which can be the loop 31 that defines the proximal-most opening 40. As the actuation force F is further applied to the actuation strand 38 while the proximal end 39a of the expandable portion 36 is braced, the mated second barb 69 causes the actuation strand 38 to move the expandable portion from the second select opening 45b toward the first select opening 45a, thereby entangling or otherwise collapsing the expandable portion 36 and actuating the expandable portion 36 from the first configuration to the expanded configuration.

Figure 2D:
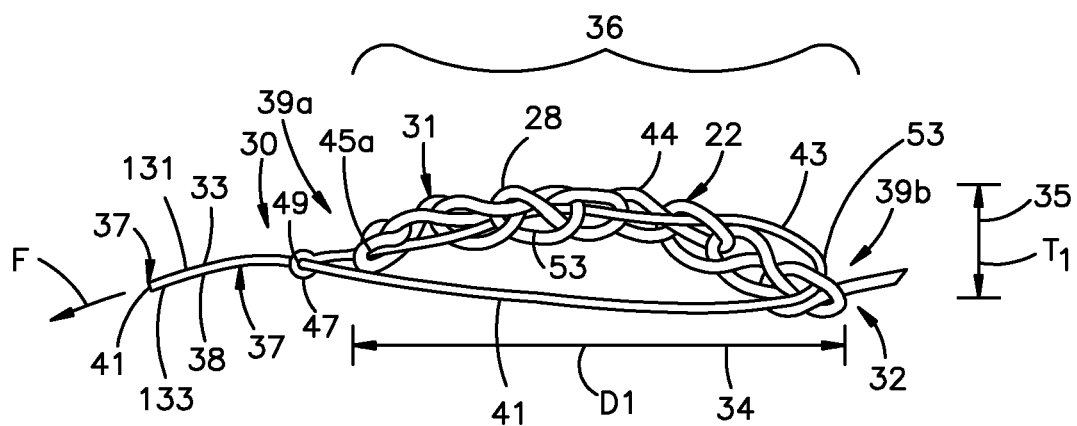
FIG. 2D is a perspective view of an anchor constructed in accordance with another embodiment.

Alternatively still, referring to FIG. 2D, the auxiliary strand 33 can define or carry a sliding member 47 which can define an opening 49 disposed proximally with respect to the expandable portion 36. In particular, the second portion 43 can be woven through a plurality of the openings 40 and can further define the sliding member 47. In accordance with the illustrated embodiment, the second portion 43 can terminate at the sliding member 47. The first portion 41 can be woven through at least one of the openings 40, for instance through a plurality of the openings 40, and can extend proximally through the opening 49 of the sliding member 47 so as to define the loop 53. Accordingly, the first and second portions 41 and 43 are slidably coupled to each other. In accordance with one embodiment, the actuation strand 38 can be configured as a woven strand that defines a plurality of openings including the opening 49. Alternatively, the opening 49 can be cut, for instance laser cut, through the second portion 43. During operation, the actuation force F can be applied to the first portion 41 when at least one of the sliding member 47 and the expandable portion 36 is braced (for instance by the anatomical structure 24 or a bracing tool) which decreases the size of the loop 53 and causes the expandable portion 36 to ride along the actuation strand 38, for instance the second portion 43, as the expandable portion 36 actuates from the first configuration to the expanded configuration. The first portion 41 can further be attached to the actuation strand 38 of a second anchor. Thus, the first portion 41 can define both the actuation portion 131 and the attachment portion 133. Otherwise stated, the actuation strand can define an end, such as the portion 41 or the portion 43, that can both receive the actuation force F and be attached to the actuation strand 38 of a second anchor. In this regard, it should be appreciated that the first portion 41 can define or carry the sliding member 47 and the second portion 43 can define the actuation portion 131 and the attachment portion 133.

Figure 2E:
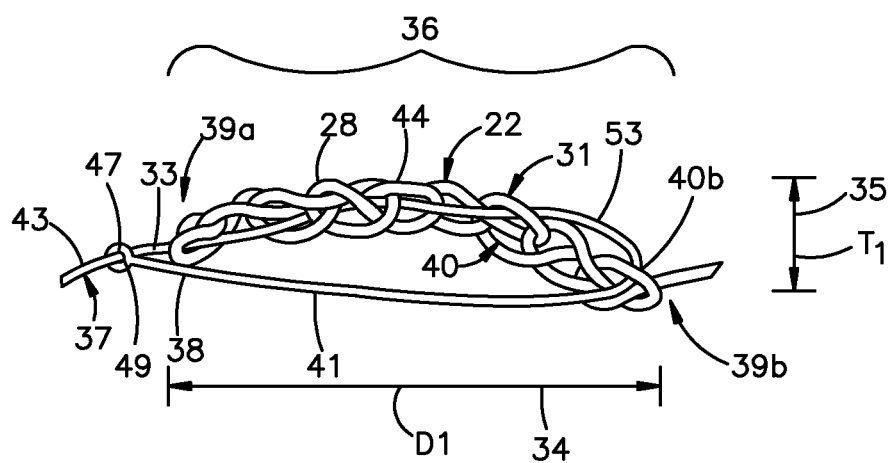
FIG. 2E is a perspective view of an anchor constructed in accordance with another embodiment.

For instance, referring to FIG. 2E, the first portion 41 can define or carry the sliding member 47 as described above with respect to FIG. 2D. In accordance with the illustrated embodiment, the first portion 41 can terminate at the sliding member 47. In particular, the second portion 43 can be woven through a plurality of the openings 40 and extend proximally from the anchor body 28 through sliding member 47. Accordingly, the first and second portions 41 and 43 are slidably coupled to each other.

It should thus be appreciated that the sliding member 47 can slidably couple the actuation portion 131 of the actuation strand 38 (for instance the first portion 41 or the second portion 43) with respect to the attachment portion 133 of the actuation strand 38 (for instance the other of the first portion 41 and the second portion 43). During operation, the actuation force F can be applied to the actuation portion 131 when the sliding member 47 or the expandable portion 36 is braced (for instance by the anatomical structure 24 or a bracing tool) which decreases the size of the loop 53 and causes the expandable portion 36 to ride along the actuation strand 38 as the expandable portion 36 actuates from the first configuration to the expanded configuration.

Figure 2F:
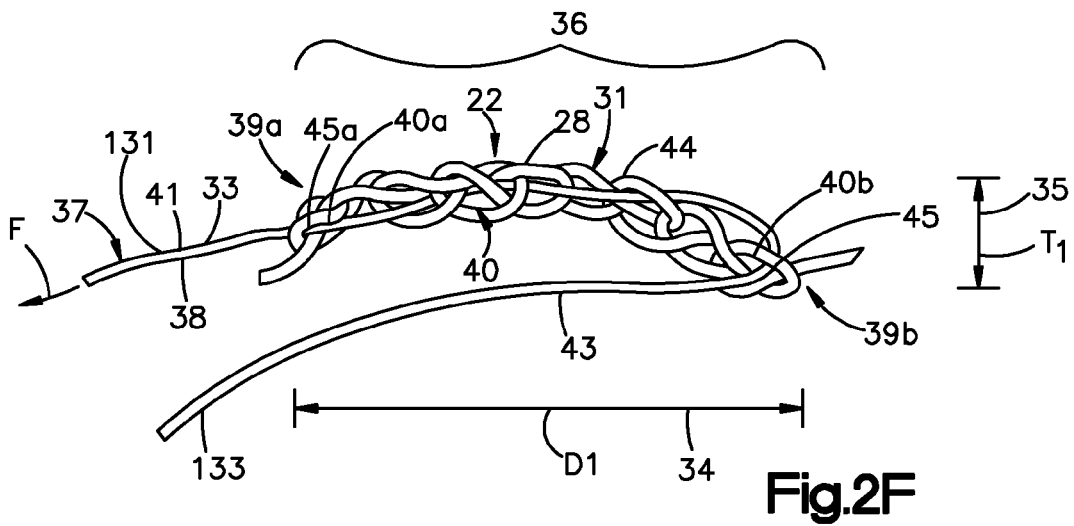
FIG. 2F is a perspective view of an anchor constructed in accordance with another embodiment.

Alternatively still, referring to FIG. 2F, the first portion 41 can extend through a plurality of the openings 40 as described above and proximally out of the anchor body 28 so as to define the actuation portion 131, and the second portion 43 can extend from the distal-most one of the openings 40 that the second portion 43 extends through, and proximally out the anatomical structure 24 without passing through any of the openings 40 or anywhere else in the anchor body 28. The second portion 43 can define the attachment portion 133 that can attach to an actuation strand 38 of the anchor 22 and is configured to attach to another anchor 22. During operation, when the actuation force F is applied to the actuation portion 131 of the actuation strand 38, such as the first portion 41 in accordance with the illustrated embodiment, when the proximal end 39a of the expandable portion 36 is braced (for instance by the anatomical structure 24 or a bracing tool), the distal end 39b of the expandable portion 36 is drawn toward the proximal end 39a along the portion of the actuation strand 38 that is woven through the openings 40, thereby causing the expandable portion 36 to become tangled as it is actuated from the first configuration to the expanded configuration.

Figure 2G:
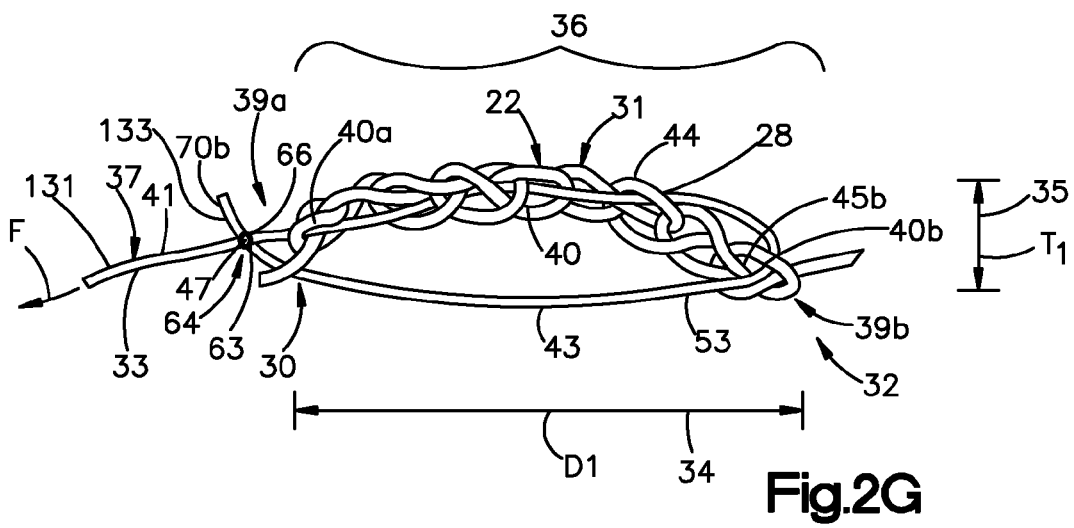
FIG. 2G is a perspective view of an anchor constructed in accordance with another embodiment.
Figure 4A:
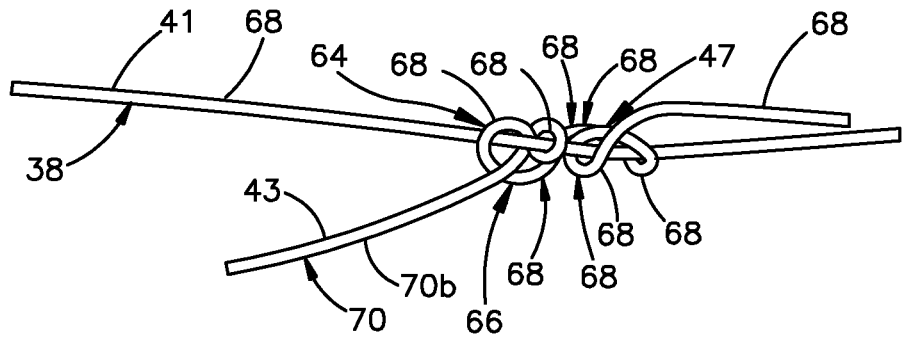
FIGS. 4A-F illustrate method steps for creating a sliding knot of the anchor illustrated in FIG. 2G in accordance with one embodiment.

Referring now to FIGS. 2G and 4A, the anchor 22 can further include a any suitable connector member 63 that can define a locking member 64 configured to selectively fix the relative position of the slidable portions (e.g., the actuation portion 131 and the attachment portion 133) of the actuation strand 38. The connector member 63 can be configured as a knot 66 or as any suitable alternatively constructed connector member 63 of the type described herein or any suitable alternative connector member. The knot 66 can be defined by the actuation strand 38 and can be disposed proximal with respect to the proximal end 30 of the anchor body 28. The actuation strand 38 can define a post end 68 of the knot 66 and a free end 70 of the knot 66 that is looped and knotted around the post end 68 such that the post end 68 is slidable with respect to the free end 70 before the free end 70 is tightened about the post end 68 at the knot 66. In accordance with the illustrated embodiment, the free end 70 can define a plurality of loops, such as four loops 71A-D about the post end 68, though it should be appreciated that the free end 70 can define as many loops about the post end 68 as desired. The free end 70 of the actuation strand 38 includes a static portion 70a that extends distally from the knot 66 and into the anchor body 28, and a free portion 70b that extends from the knot 66 and does not extend into the anchor body 28.

The post end 68 can be defined by one of the first portion 41 and the second portion 43, and the free end 70 can be defined by the other of the first portion 41 and the second portion 43. In accordance with the illustrated embodiment, the post end 68 is defined by the actuation portion 131, illustrated as the first portion 41, and the free end 70 is defined by the second portion 43. Accordingly, the first portion 41 and the second portion 43 are slidably coupled to each other such that the first portion 41 slides relative to the second portion 43. Thus, it should be appreciated that the locking member 64 can further define the sliding member 47, and the knot 66 can further be referred to as a sliding locking knot.

During operation, when the actuation force F is applied to the first portion 41, the first portion 41 slides proximally with respect to the second portion 43 thereby reducing the size of the loop 53 and actuating the anchor body 28 from the first configuration to the expanded configuration. The free end 70, which can be defined by the second portion 43, can be tightened so as to tighten the free end 70 about the post end 68, thereby locking the post end 68, defined by the first portion 41, with respect to translation relative to the free end 70. When the free end 70 is tightened about the post end 68, thereby fixing the knot 66 about the post end 68, the free end 70 can define the attachment 133 of the actuation strand 38. Alternatively or additionally, once the anchor body 28 has been expanded to the expanded configuration, the knot 66 can translate distally along the post end 68, thereby decreasing the size of the loop 53 and actuating the expandable portion 36 to the expanded configuration, and the knot 66 can subsequently be tightened about the post end 68 so as to fix the decreased size of the loop 53 and in some instances assist in retaining the anchor body 28 in the expanded configuration.

Figure 4B:
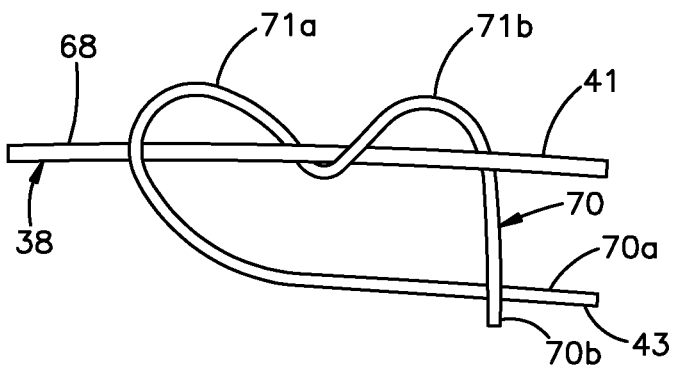

The construction of the knot 66 in accordance with one embodiment will now be described with reference to FIGS. 4A-E. As illustrated in FIG. 4A, the free end 70 defines a plurality of sliding loops 71A-D about the post end 68 that are configured to slide along the post end 68. At least one of the loops 71A-D, for instance the distal-most loops 71A and 71B as illustrated, can further define locking loops that are configured to be tightened when a tightening force F1 is applied to the free portion 70b, thereby tightening the free end 70 about the post end 68 in the manner described above. As illustrated in FIG. 4B, the knot 66 is created by looping the free end 70 about the post end 68 any of at least once such as twice along the same direction, thereby creating at least one sliding loop 71A such as a pair of loops, for instance a first sliding loop 71A and a second sliding loop 71B, about the post end 68. It should be appreciated that the free end 70 can be looped about the post end 68 as many times as desired so as to create as many sliding loops 71 as desired. In accordance with the illustrated embodiment, the free end 70 is translated distally as it is looped about the post end 68 such that the first loop 71A is disposed proximally with respect to the second loop 71B. The free end 70 thus defines a free portion 70b that extends proximally from the loops 71 and a static portion 70a that extends distally from the loops 71, and can also define the second portion 43 of the actuation strand 38.

Figure 4C:
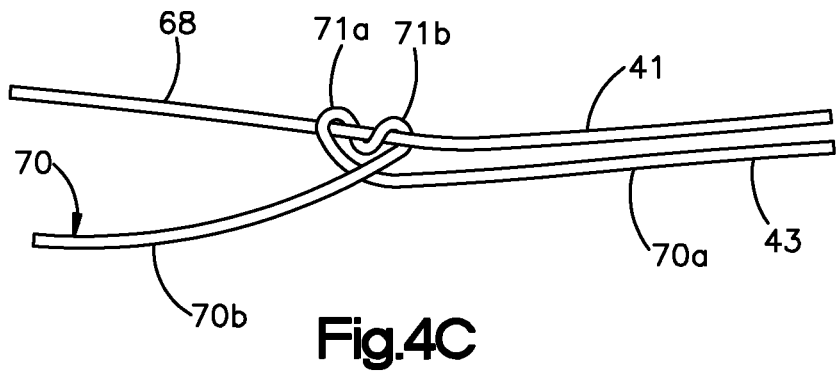
Figure 4D:
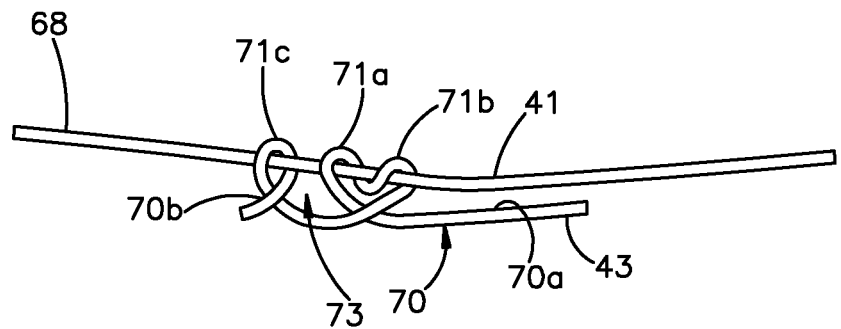
Figure 4E:
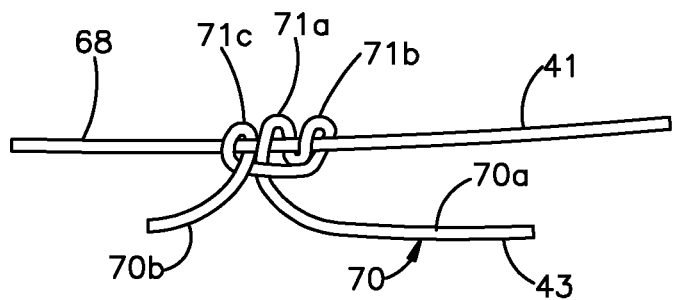

Next, referring to FIG. 4C, the free portion 70b of the free end 70 is tightened while maintaining the post end 68 and the static portion 70a in tension so as to bring the sliding loops 71A and 71B against each other. For instance, a distal tightening force can be applied to the free portion 70b, thereby bringing the second loop 71B against the first loop 71A. Next, as illustrated in FIG. 4D, the free portion 70b is again looped around the post end 68 in the same direction as the sliding loops 71A and 71B, at a location proximal of the first sliding loop 71A, so as to define a third sliding loop 71C. As the free portion 70b is looped the post end 68, a gap 73 is defined between the free portion 70b and the post end 68. The free portion 70b can then be fed through the gap 73 such that the sliding loop 71C further defines a locking loop, and the free portion 70b extends out from the sliding loop 71C. Next, referring to FIG. 4E, the free portion 70b can be tightened so as to bring the third sliding loop 71C against the immediately adjacent and proximally spaced first sliding loop 71A, such that the free portion 70b extends out from the gap 73.

Figure 4F:
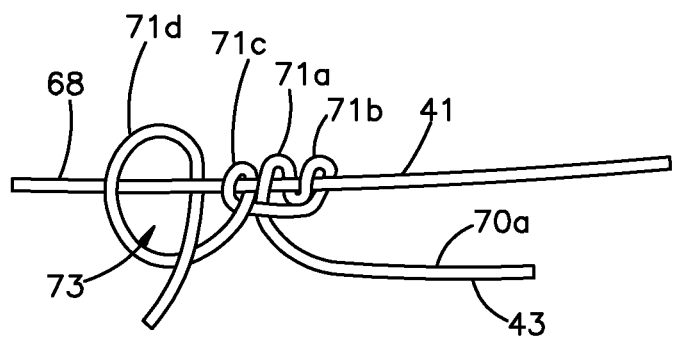

As illustrated in FIG. 4F, the free portion 70b is again looped the post end 68 in the same direction as the sliding loops 71A-C, at a location proximal of the third sliding loop 71C, so as to define a fourth sliding loop 71D. As the free portion 70b is looped the post end 68, a gap 73a is defined between the free portion 70b and the post end 68. The free portion 70b can then be fed through the gap 73 such that the fourth sliding loop 71D further defines a locking loop, and the free portion 70b extends out from the fourth sliding loop 71D. Next, the free portion 70b can be tightened so as to bring the fourth sliding loop 71D against the immediately adjacent and proximally spaced third sliding loop 71C, as illustrated in FIG. 4A.

It be appreciated that the knot 66 can define any number of sliding loops 71, such as at least one sliding loop 71 or a plurality of sliding loops 71. It should be further appreciated that at least one up to all of the sliding loops 71 can further define locking loops 71 as desired. During operation, once the knot 66 has been created, the actuation force F can be applied to the post end 68, which can define the actuation portion 131, illustrated as the first portion 41, such that the expandable portion 36 of the anchor body 28 expands from the first configuration to the expanded configuration. It should be further appreciated that the knot 66 can be disposed in an unlocked configuration whereby the post end 68 can translate through to the knot 66 relative to the loops 71 as the anchor body 28 expands. A locking force, which can be a tensile force, can be applied to the free portion 70b so as to actuate the knot 66 to a locked configuration. In particular, the locking loops 71 are tightened about the post end 68, preventing the actuation portion 131 from translating through the knot 66. The free portion 70b of the free end 70 can extend from the knot 66 as illustrated in FIG. 2G and define the attachment portion 133 of the actuation strand 38 that attaches the anchor body 28 to another anchor.

Figure 2H:
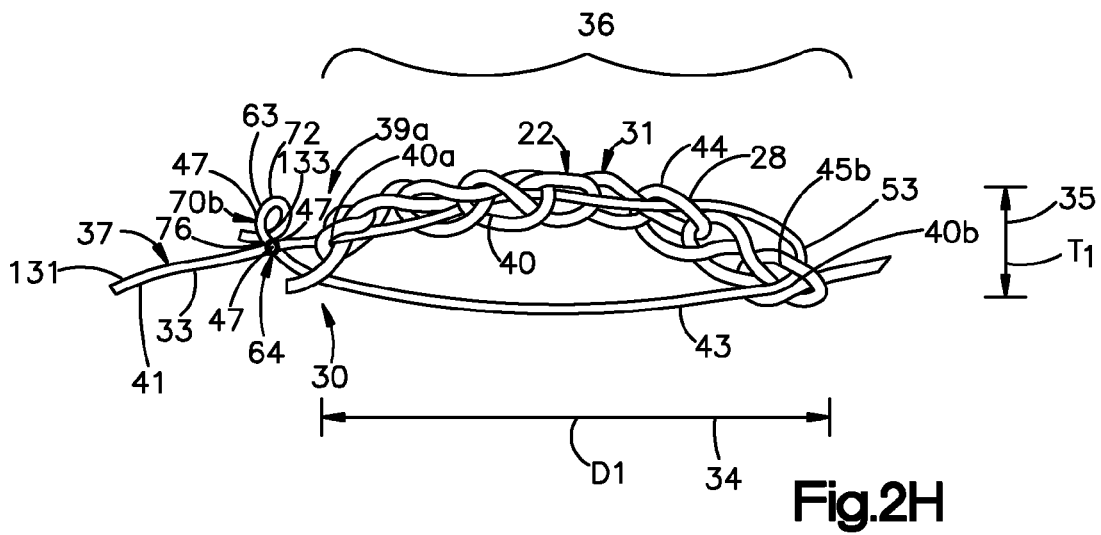
FIG. 2H is a perspective view of an anchor constructed in accordance with another embodiment.

As illustrated in FIG. 2H, the free portion 70b, and thus the attachment portion 133, can define a connector member 63 that is configured to attach to an actuation strand of another anchor, either directly or indirectly. In accordance with the illustrated embodiment, the connector member 63 is configured as an eyelet 72 that is integral with the actuation strand 38. Accordingly, because the actuation strand 38 extends from the expandable portion 36 of the anchor body 28, it can also be said that the eyelet 72 likewise extends from the expandable portion 36. Alternatively or additionally, the anchor body 28 can include an eyelet that extends from the expandable portion 36, an eyelet 90 (see FIGS. 8A-C) that also extends from the expandable portion 36, or any alternatively constructed eyelet that extends, directly or indirectly, from the expandable portion 36.

The attachment portion 133 can be defined by the free portion 70b of the actuation strand 48 as illustrated in FIG. 2G can be fed through an eyelet of a second anchor body, configured as the eyelet 72, the eyelet 84b, the eyelet 90, or any suitable alternatively constructed eyelet that is attached, directly or indirectly, to the expandable portion of an anchor body so as to attach the anchor body 28 to the second anchor body. In that regard, it should be appreciated that the anchor assembly 20 can include at least one connector member 63 that is configured to join more than one anchor together. The connector member 63 can be integral with at least one of the actuation strands 38, or can be separate and attached to at least one of the actuation strands 38.

Figure 5A:
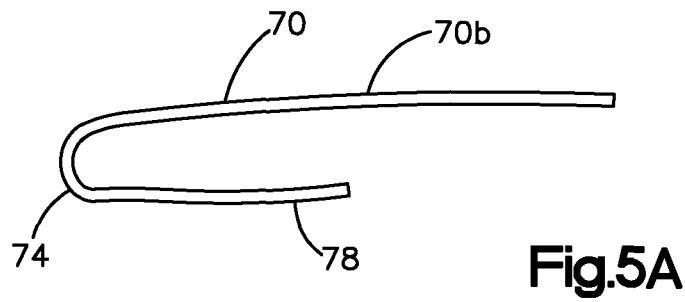
FIGS. 5A-B illustrate method steps for creating an eyelet of the anchor illustrated in FIG. 2H in accordance with one embodiment.
Figure 5B:
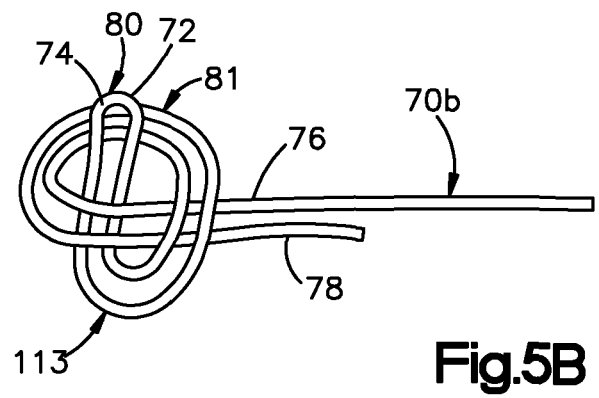

Referring to FIGS. 5A-B, the eyelet 72 can be constructed by first folding the free portion 70b over itself so as to define a folded portion 74 that extends from a first end, such as a stem 76. The stem 76 thus extends between the knot 66 (see FIG. 2H) and the folded portion 74. The free portion 70b defines a second end, such as a terminal end 78, that extends from the folded portion 74. The free portion 70b can be oriented such that the terminal end 78 can be disposed adjacent the stem 76. The folded portion 74 can be looped over the stem 76 and the terminal end 78 so as to define a loop 81, and can subsequently be fed under the stem 76 and the terminal end 78, and through the loop 81 so as to define an eyelet knot 80 at a closure location 111 that closes the folded portion 78 and defines the eyelet 72. A tensile force can then be applied to the folded portion 78 so as to tighten the knot 80 and close the folded portion 74, such that the stem 76 and the terminal end 78 extend from the knot 80, and the folded portion 74 also extends from the knot and defines the eyelet 72. Thus, the eyelet 72 has a base that is defined, for instance, by the knot 80, or can be defined by any alternative closure member.

Figure 5C:
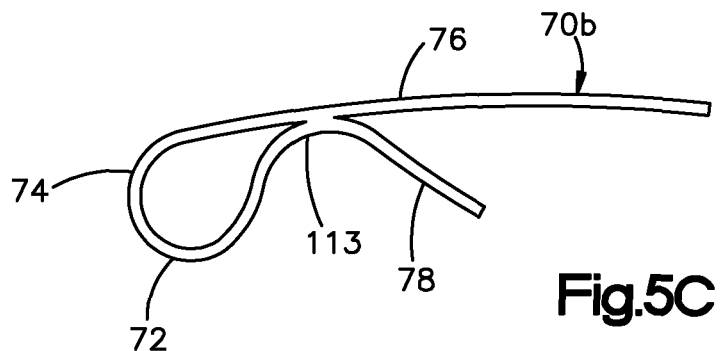
FIG. 5C illustrates method steps for creating an eyelet of the anchor illustrated in FIG. 2H in accordance with an alternative embodiment.
Figure 5D:
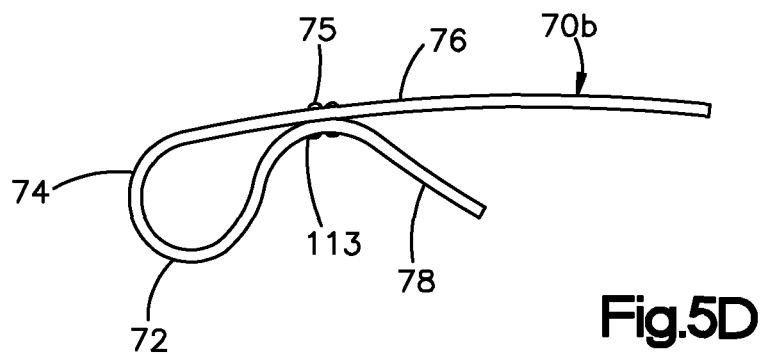
FIG. 5D illustrate method steps for creating an eyelet of the anchor illustrated in FIG. 2H in accordance with an alternative embodiment.

For instance, referring to FIG. 5C, the terminal end 78 can be welded, for instance heated or via an adhesive, to the stem 76 at the closure location 113 so as to close the folded portion 74 and define the eyelet 72. The closure location 113 can define the base of the eyelet 72. Alternatively still, referring to FIG. 5D, the terminal end 78 can be stitched to the stem 76 at the closure location 113 so as to close the folded portion 74 and define the base of the eyelet 72. For instance, a strand, such as at least one suture strand 75, can be stitched through the terminal end 78 and the stem 76 so as to join the terminal end 78 to the stem 76. Thus, it should be appreciated that the terminal end 78 can be attached to the stem 76 in any known manner so as to define the eyelet 72, such that a strand, such as an actuation strand, of another anchor 22 or a connection strand can be fed through the eyelet 72 and apply a force, for instance an approximation force, to the eyelet 72 as described above with respect to FIGS. 1A-B. The approximation force can be sufficient so as to approximate a gap 24c that is disposed between the anchor bodies 28 as illustrated in FIGS. 1A-B.

While the actuation strand 38 can be separate or non-integral from the substrate 42 of the anchor body 28 and attached to the anchor body 28 as described above, it should be appreciated that the actuation member 37 can alternatively be integral with the anchor body 28. Thus, the actuation strand 38 can alternatively be integral with the substrate 42, such as the anchor body strand 44, and thus also therefore integral with the expandable portion 36.

Figure 6A:
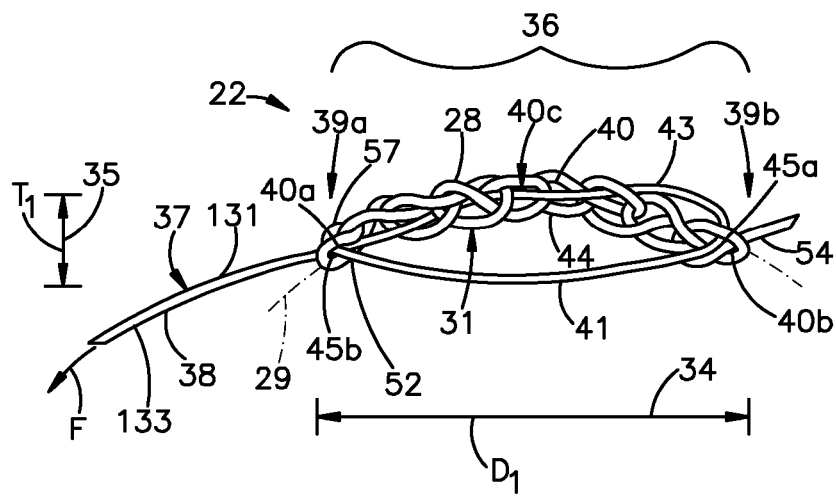
FIG. 6A is a perspective view of an anchor including an actuation strand integral with an anchor body woven through a plurality of openings defined by an expandable portion of the anchor body, showing the anchor body in a first configuration.
Figure 6B:
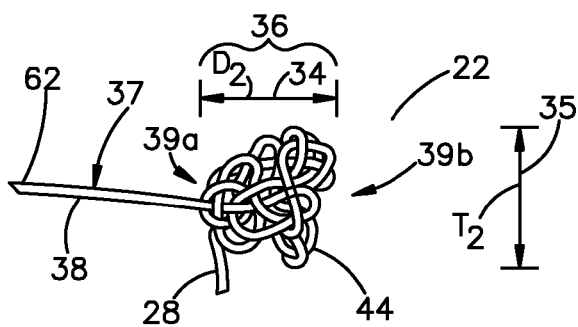
FIG. 6B is a perspective view of the anchor illustrated in FIG. 6A, showing the anchor body in an expanded configuration.
Figure 6C:
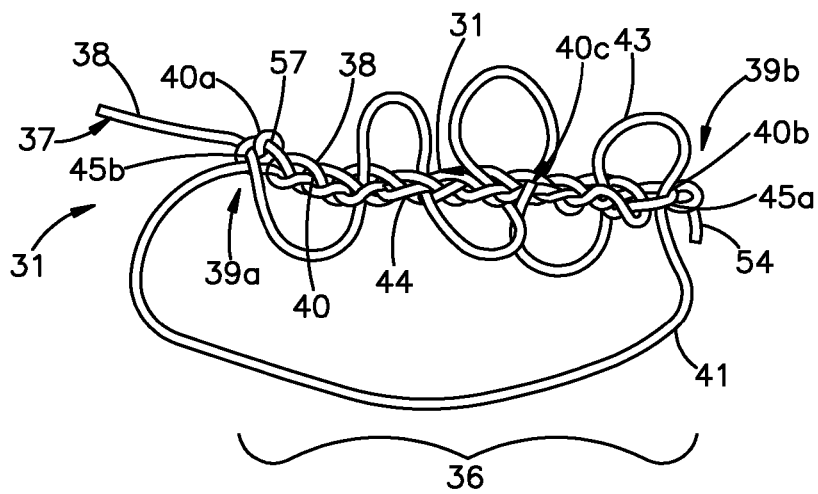
FIG. 6C is a perspective view illustrating the insertion of the actuation strand through the openings when the anchor body is in the first configuration as illustrated in FIG. 6A.

For instance, Referring now to FIGS. 6A-C, the actuation strand 38 can be defined by one of the first and second end portions 52 and 54 of the anchor body strand 44, which can be configured as described above with respect to FIGS. 3A-C, or otherwise configured. Thus, the actuation strand 38 can be integral with the anchor body 28, and thus integral with the expandable portion 36. In accordance with the illustrated embodiment, the first end portion 52 that extends proximally from the anchor body 28 defines the actuation strand 38, and the second end portion 54 that extends distally from the anchor body 28 can be terminated at a location proximate to the anchor body 28, for instance proximate to corresponding distal end 39b of the expandable portion 36, such that the second end portion 54 has a length insufficient to attach the anchor body 28 to an anchor body of a second anchor.

While the first end portion 52 of the anchor body strand 44 can be terminated at a location proximate to the proximal-most loop 57 of the loops 31 as described above with reference to FIGS. 3A-C, the first end portion 52 can alternatively define the actuation strand 38 that extends distally from the proximal end 39a of the expandable portion 36, and can be woven through, and thus extend through, at least one select opening 45a of the openings 40 that is spaced distally from the proximal end 39a of the expandable portion 36. The select opening 45a can be the distal-most opening 40b as illustrated, or can alternatively be one of the intermediate openings 40c. The actuation strand 38 can be extended through the select opening 45a so as to define a loop 53, including first and second portions 41 and 43. For instance, the first portion 41 can extend from the first end portion 52 distally to the first select opening 45a. The second portion 43 can extend from the first select opening 45a proximally out the anchor body 28 and out the anatomical structure 24. For instance, in accordance with the illustrated embodiment, the second portion 43 can be woven through, and thus extend through, at least one of the openings 40 such as a plurality of select openings 40 that can be disposed between the proximal end 39a and the select opening 45a. For instance, the second portion 43 of the actuation strand 38 can be woven through at least one of the intermediate openings such as a plurality of the intermediate openings 40c. The second portion 43 can extend out the expandable portion 36 of the anchor body 28 through the second select opening 45b of the openings 40, which can be the proximal-most opening 40a, for instance of the proximal-most stopper knot 46.

Thus, a tensile force F, which can be a proximally directed force, applied to the actuation strand 38, for instance at the first portion 41, when the expandable portion 36, such as the proximal end 39a, is braced, causes the expandable portion 36 to move from the first configuration to the expanded configuration. The first portion 41 can thus define the actuation portion 131 of the integral actuation strand 38. In particular, the expandable portion 36 slides along the actuation strand 38, for instance along the second portion 43, as it collapses along the direction of elongation 35 from the first distance D1 to the second distance D2 along the direction of elongation 34. As the expandable portion 36 collapses along the actuation strand 38, the expandable portion 36 can become entangled or otherwise deformed in the second direction as it travels along the second portion 43, thereby causing the expandable portion 36 to expand in the second direction 35 from the initial maximum thickness T1 to the expanded maximum thickness T2 that is greater than the initial maximum thickness T1. The first portion 41 can then be terminated, for instance cut and singed at a location proximate to the anchor body 28, or can alternatively define an attachment portion 133 that can be attached to a second anchor, for instance joined to a complementary connector member of the second anchor in any desired manner as described herein. Thus, it should be appreciated that the first portion 41 that extends out the anatomical structure 24 from the anchor body 28 can define at least one of or both of the actuation portion 131 and the attachment portion 133.

Figure 7B:
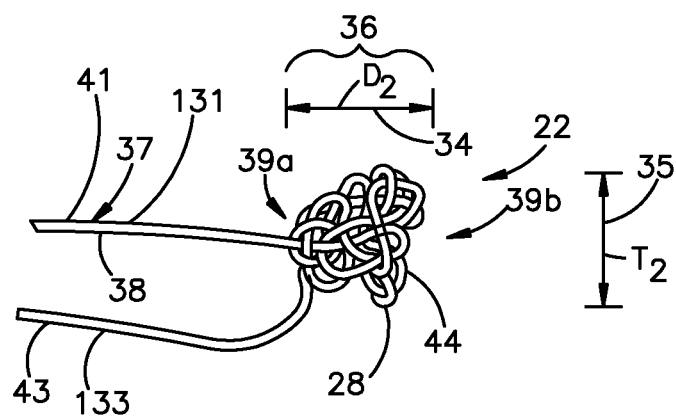
FIG. 7B is a perspective view of the anchor illustrated in FIG. 7A, showing the anchor body in an expanded configuration.

Alternatively, as illustrated in FIGS. 7A-B, the anchor 22 can be constructed as described above with respect to FIGS. 6A-C, however the second end portion 54 of the anchor body strand 44 can extend from the distal end 39b of the expandable portion 36 a sufficient distance so as to define the attachment portion 133 that is configured to attach to a second anchor so as to attach the anchor 22 to the second anchor. For instance, the attachment portion 133 can attach to an anchor strand of the second anchor. The attachment portion 133 can be integral with the anchor strand of the second anchor, or the anchor assembly 20 can include a connector that attaches the attachment portion 133 to the second anchor, such as the actuation strand of the second anchor. The connector can be integral with at least one or both of the actuation strand 38 and the actuation strand of the second anchor, or can be separate and attached to at least one or both of the actuation strand 38 and the actuation strand of the second anchor. During operation, the actuation force F can be applied to the first portion 41, which can define the actuation portion 131 as described above. It should be appreciated that the actuation force F can be at least partially counterbalanced by the attachment portion 133, which defined by the second portion 43 in the illustrated embodiment. Furthermore, as described above with respect to FIG. 1D, the opposed first and second ends of the actuation strand 38 (which can be defined by the actuation portion 131 and the attachment portion 133, respectively) can be tied, stitched, or otherwise secured to another anatomical structure 27, thereby inducing tension in the actuation strand 38 and securing the auxiliary structure 25 between the actuation strand 38 and the anatomical structure 24.

Figure 8A:
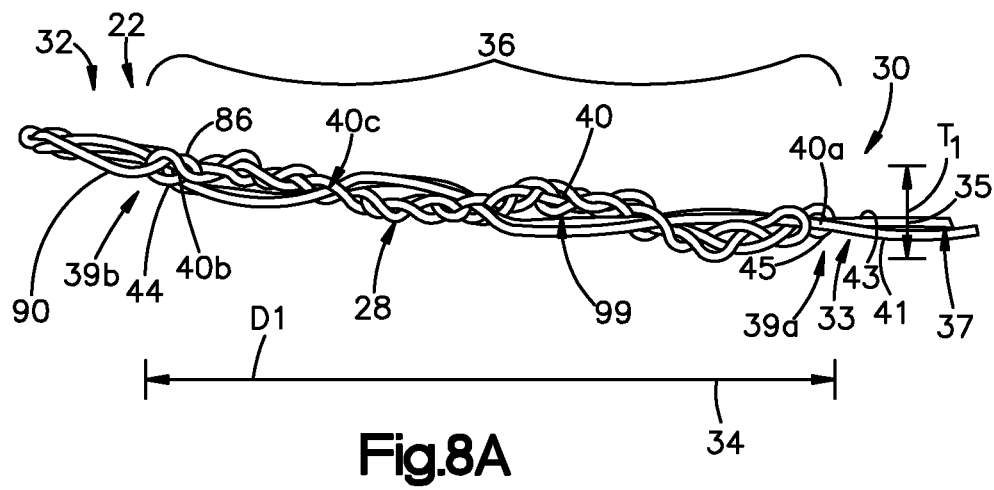
FIG. 8A is a perspective view of an anchor including an anchor body and an eyelet extending from the anchor body, and an actuation strand attached to the eyelet and woven through an expandable portion the anchor body, showing the expandable portion in a first configuration.

Referring now to FIG. 8A, and as described above, the anchor body 28 can include an eyelet 90 that extends from the expandable portion 36. In accordance with the illustrated embodiment, the eyelet 90 can be disposed at the distal end 32 of the anchor body 28 when the expandable portion 36 is in the first configuration. The eyelet 90 can be constructed as described herein, or can alternatively comprise a select one of the loops of the anchor body 28, for instance a loop that might be larger than one or more of the other loops defined by the anchor body 28. The anchor 22 can include an auxiliary strand 33 that can define an actuation strand 38 configured to actuate the anchor 22 between the first configuration and the expanded configuration in the manner described above when the anchor is implanted at the target anatomical structure 24.

The auxiliary strand 33 can define first and second portions 41 and 43, and a connection location such as a fold 86 that is disposed between and integrally attached between the first and second portions 41 and 43. The fold 86 can extend through the eyelet 90, so as to attach the auxiliary strand 33 to the eyelet 90, such that the first and second portions 41 and 43 extend proximally from the eyelet 90 through at least a select opening 45 such as a plurality of select openings 45 of the openings 40 when the expandable portion 36 is in the first configuration. The select openings 45 can include at least one intermediate opening 40c, and can further include the proximal-most opening 40a. The auxiliary strand 33 can further be tied or otherwise attached to the eyelet 90 if desired. In accordance with the illustrated embodiment, the first and second portions 41 and 43 extend through a plurality of select openings 45 of the openings 40, and further extend through the same openings 40. For instance, the first and second portions 41 and 43 can extend through every other opening 40 along the proximal direction from the eyelet 90, every third opening 40 along the proximal direction from the eyelet 90, every opening 40 along the proximal direction from the eyelet 90, or can extend through the eyelets 40 in any regular repeating pattern or any irregular nonrepeating pattern as desired.

Figure 8B:
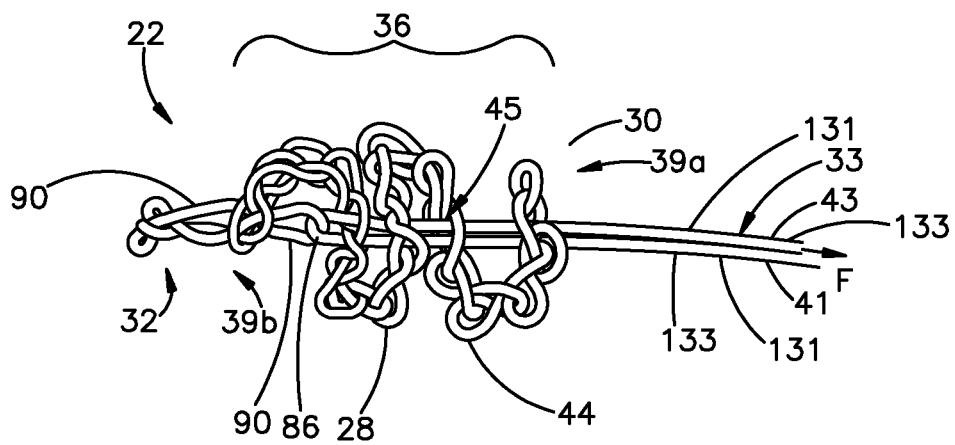
FIG. 8B is a perspective view of the anchor illustrated in FIG. 8A, showing the expandable portion being actuated from the first configuration to an expanded configuration.
Figure 8C:
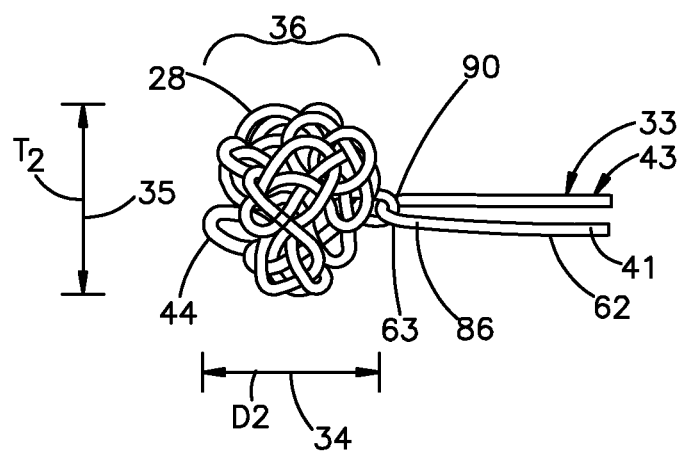
FIG. 8C is a perspective view of the anchor illustrated in FIG. 8A, showing the expandable portion in the expanded configuration.

Referring to FIG. 8B, because the first and second portions 41 and 43 extend through the same select openings 45 along the proximal direction from the eyelet 90, the first and second portions 41 and 43 define a travel path for the eyelet 90 through the select openings 45 when the actuation force F is applied to the first and second portions 41 and 43. Accordingly, as the first and second portions 41 and 43 of the auxiliary strand 33 travel proximally through the select openings 45 of the anchor body 28 in response to the applied actuation force F, the eyelet 90 travels with the actuation strand 38 through the select openings 45 as the expandable portion actuates from the first configuration to the expanded configuration. As a result, as illustrated in FIG. 8C, the auxiliary strand 33 can travel a sufficient distance in response to the applied actuation force F such that the fold 86 is disposed proximally with respect to the expandable portion 36 when the expandable portion 36 is in the expanded configuration. Accordingly, the eyelet 90 also extends proximally from the expandable portion 36 when the expandable portion 36 is in the expanded configuration.

The eyelet 90 can thus define a connector member 63 of the anchor body 28, and thus the anchor 22, that is configured to attach to a second anchor, either directly (for instance via a connector member that is integral with the second anchor), or indirectly (for instance via at least one connector member that is separate or non-integral from and attached to the second anchor). In accordance with one embodiment, the eyelet 90 can receive a strand that attaches the anchor 22 to the second anchor. For instance, the received strand can be the actuation strand of the second anchor, or a connector strand that attaches, directly or indirectly, the actuation strand of the second anchor to the eyelet 90.

The anchor body 28 can be constructed in any manner as desired, for instance by creating the eyelet 90 and further by creating the expandable portion 36 in any suitable manner as desired. Thus, the anchor body strand 44 can be tied in a knot so as to define the eyelet 90, or welded, stitched, or otherwise attached to itself so as to define the eyelet 90.

Figure 9A:
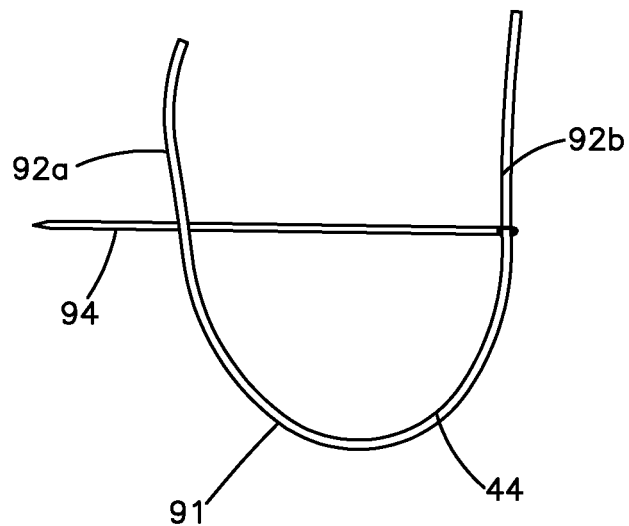
FIGS. 9A-G illustrate method steps of creating the eyelet illustrated in FIG. 8A in accordance with one embodiment.
Figure 9B:
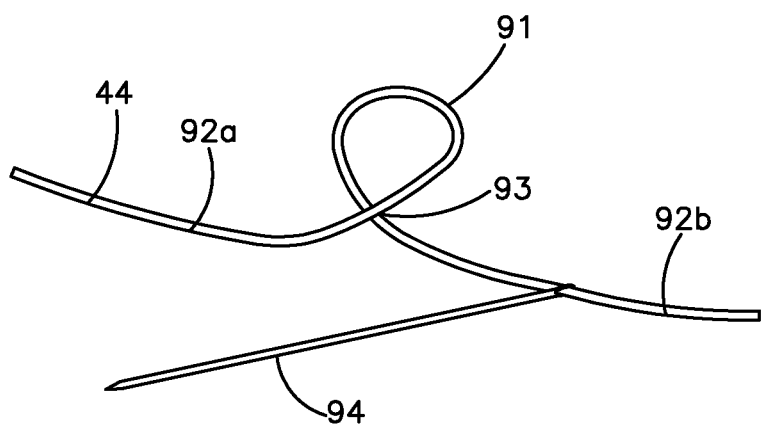
Figure 9C:
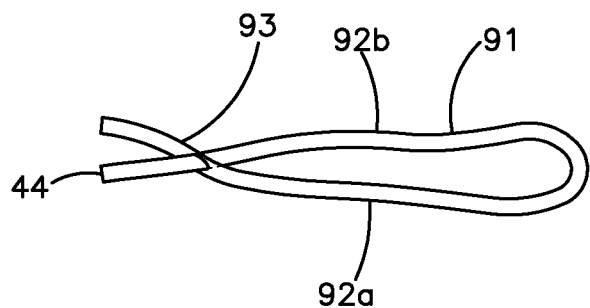

In accordance with one embodiment, referring to FIGS. 9A-B generally, the anchor body strand 44 can be folded and stitched through itself so as to define a loop 91, and first and second segments 92*a* and 92*b*, respectively, that extend from opposed sides of the loop 91. The tip of a needle 94 can be inserted through the first segment 92*a* so as to define a first channel that extends through the first segment 92*a*. The second segment 92*b* can be fed through the eyelet of the needle 94 at the trailing end of the needle 94. The needle 94 can then be translated forward through the first segment 92*a* such that the second segment 92*b* is drawn through the channel in the first segment 92*a* as created by the needle 94, thereby closing the loop 91 as illustrated in FIG. 9B and defining a first stitch 93. The loop 91 extends distally from the first stitch 93. As illustrated in FIG. 9C, the second segment 92*b* can be translated in opposite directions through the first segment 92*a* so as to adjust the size of the loop 91 as desired. In accordance with one embodiment, the loop 91 can be adjusted to a length of approximately 5 mm when pulled taught as illustrated in FIG. 9C.

Figure 9D:
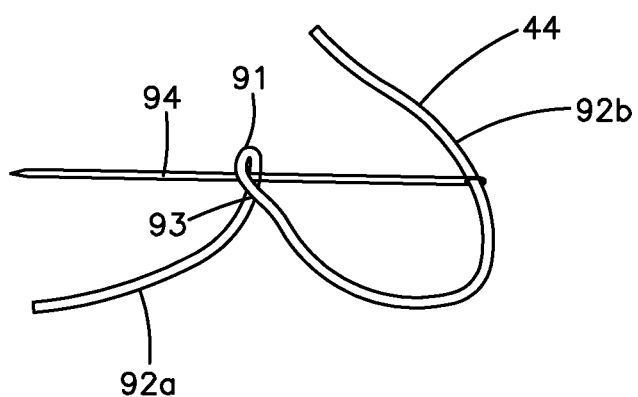
Figure 9E:
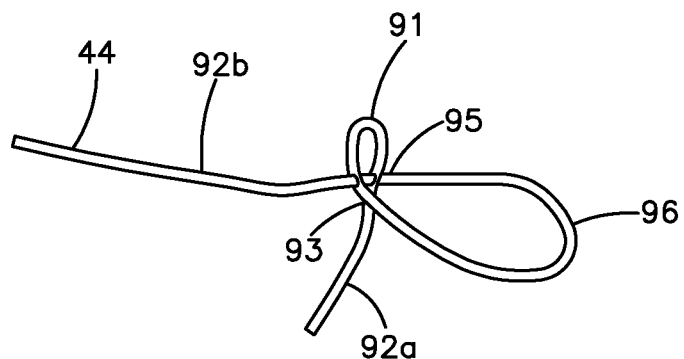

Next, referring to FIGS. 9D-E, the anchor body strand 44 can be stitched through itself a second time. For instance, the tip of the needle 94 can be driven through both segments 92*a* and 92*b* of the anchor body strand 44 at a location distal of the first stitch 93, thereby creating second and third channels that extend through the first and second segments 92*a* and 92*b*, respectively, at a location distal of the first stitch 93. As illustrated in FIG. 9E, the second segment 92*b* can be fed through the eyelet of the needle 94, and the needle 94 can then be translated forward through the second and third channels such that the second segment 92*b* is drawn through itself at one side of the loop 91, and further drawn through the first segment 92*a* at the opposite side of the loop 91 so as to define a second stitch 95 at a location distal of the first stitch 93. The first and second stitches 93 and 95 can define a base of the loop 91. The second segment 92*b* further defines a loop 96 that extends from the first and second stitches 93 and 95. It is appreciated that the size of the loop 91 is therefore decreased, for instance by approximately 1 mm, after the second stitch 95 is created.

Figure 9F:
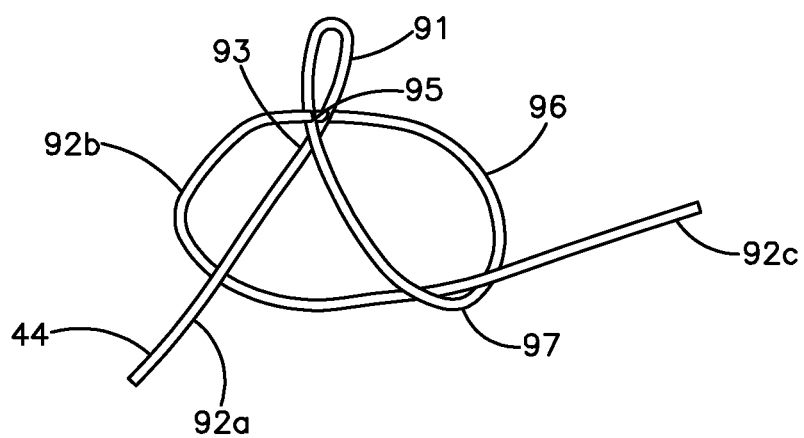
Figure 9G:
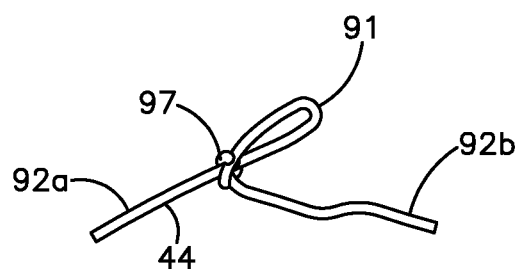

Referring to FIGS. 9F-G, the anchor body strand 44 can be tied in a knot 97 at the first and second stitches 93 and 95 to fix the size of the loop 91, which defines the eyelet 90. For instance, the second segment 92*b* can define a free end 92*c* that extends from the third channel of the second segment 92*b* through the loop 96, and is subsequently tightened so as to define the knot 97. Thus, the knot 97 is disposed at the base of the loop. It should be appreciated that the second segment 92*b* can be stitched through the loop 91 as many times as desired prior to creating the knot 97 so as to fix the loop 91. Thus, it should be appreciated that the eyelet 90 can be created by stitching the anchor body strand 44 through itself so as to create at least one stitch, for instance two stitches, thereby define a loop, and subsequently tying a knot 97 about the base of the loop so as to fix the eyelet 90.

Figure 10A:
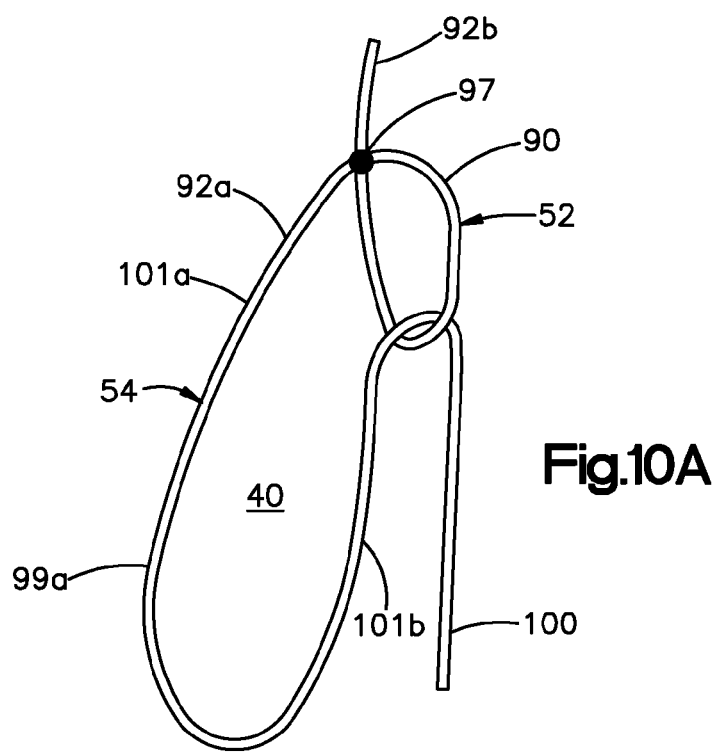
FIGS. 10A-H illustrate method steps of creating the expandable portion illustrated in FIG. 8A in accordance with one embodiment.

One method of constructing the expandable portion includes braiding the actuation strand 44 as will now be described with reference to FIGS. 10A-H. For instance as illustrated in FIG. 10A, one end of the anchor body strand 44 includes the eyelet 90 having a base that is defined, for instance, by the knot 97 or any alternative closure member, such as the closure members illustrated in FIGS. 5A-D. The anchor body strand 44 thus defines a first or proximal end portion 52 that defines the eyelet 90 and the second segment 92*b*, and a second or distal end portion 54 that extends from the eyelet 90 and can include the first segment 92*a*.

The method of constructing the expandable portion 36 of the anchor body 28 generally includes the step of braiding the second end portion 54 distally so as to define a plurality of similarly constructed loops 99 defining respective openings 40 that are spaced substantially along the direction of elongation 34 as illustrated in FIG. 8A. It should be appreciated that if the loops 99 and respective openings 40 are spaced along a direction that has a directional component along the direction of elongation 34, the loops 99 and openings 40 can be said to be spaced substantially along the direction of elongation 34. Each of the loops 99 can define respective ones of the plurality of openings 40 as described above. For instance, as illustrated in FIG. 10A, the method can further include the step of looping the second end portion 54 through a first prior loop, such as the eyelet 90, so that the second end portion 54 defines a first new loop, such as a first loop 99*a* that extends between the knot 97 and the eyelet 90. The first loop 99*a* defines a respective opening 40, and includes a first segment 101*a* and a second segment 101*b*. The first segment 101*a* of the first loop 99*a* extends from the knot 97, and the second segment 101*b* extends distally from the first segment 101*a* so as to define the first loop 99*a*. The second end portion 54 can define a free end 100 that extends distally from the second segment 101*b*, such that the free end 100 of the second end portion 54 and the first loop 99a are on opposite sides of the eyelet 90.

Figure 10B:
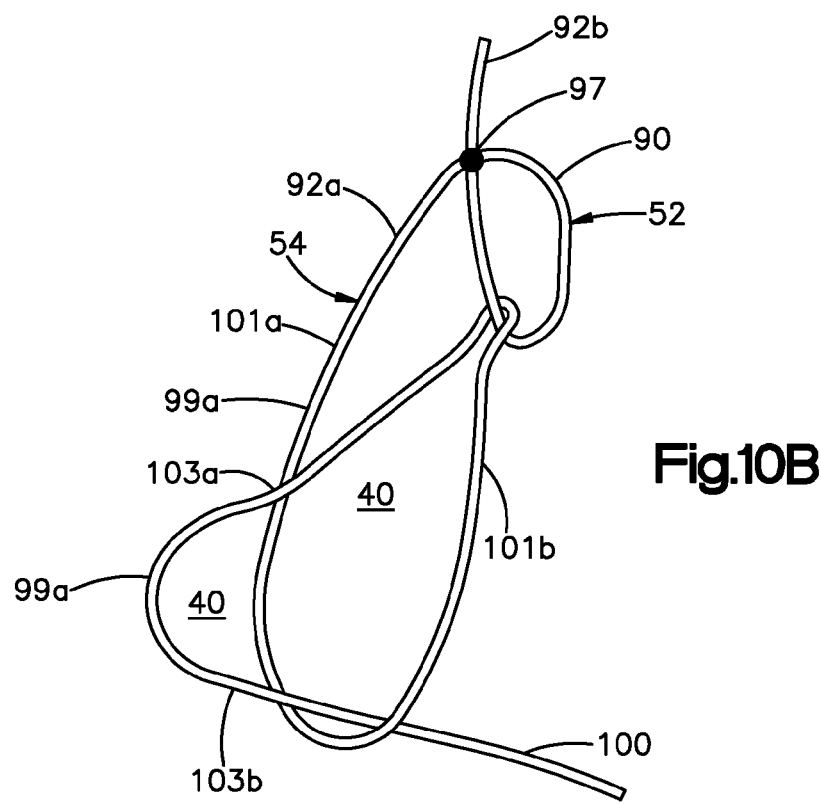
Figure 10C:
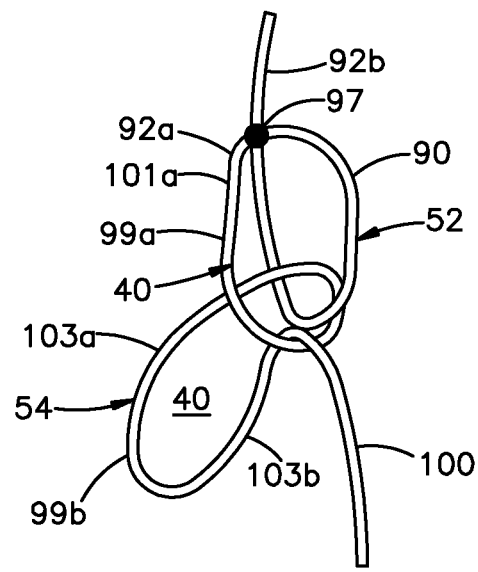

Next, as illustrated in FIG. 10B, the second end portion 54 can be folded so as to define a second new loop, such as a second loop 99b that defines a respective opening 40 and includes a first segment 103a and a second segment 103b. The second loop 99b can be pulled through a second prior loop, which can be defined by the first loop 99a, such that the first segment 103a is disposed proximally with respect to the second segment 103b. Alternatively, the free end 100 can be fed through the first loop 99a in a first direction, folded so as to define the second loop 99b, and fed back through the first loop 99a in a second direction that is opposite the first direction. Accordingly, the first segment 103a extends from the eyelet 90, and the second segment 103b extends from the first segment 103a so as to define the second loop 99b. The free end 100 of the second end portion 54 extends distally from the second segment 103b, such that the free end 100 of the second end portion 54 and the second loop 99b are on opposite sides of the first loop 99a. As illustrated in FIG. 10C, tension can be applied to the first segment 103a of the second loop 99b, which causes the size of the first loop 99a to decrease and tighten about the second loop 99b.

Figure 10D:
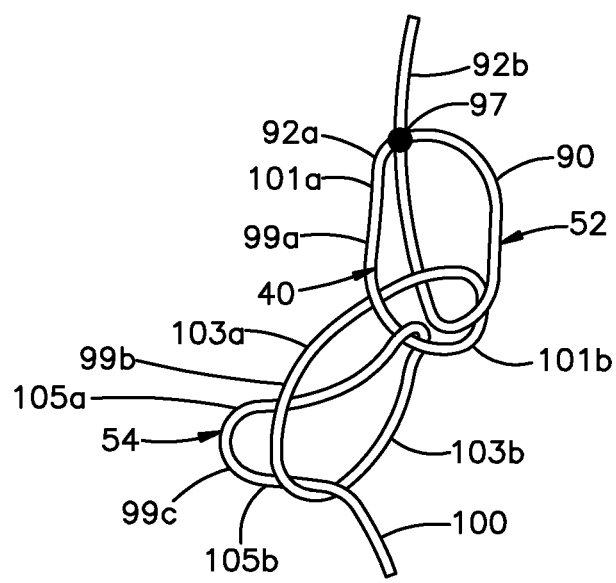
Figure 10E:
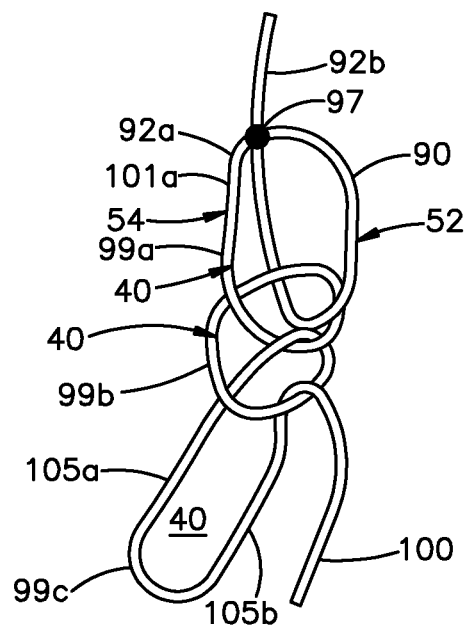

Next, as illustrated in FIG. 10D, the second end portion 54 is again folded so as to define a new loop, such as a third loop 99c, that defines an opening 40 and includes a first segment 105a and a second segment 105b. The third loop 99c can be pulled through the opening 40 of a prior loop, such as the second loop 99b, such that the first segment 105a is disposed proximal with respect to the second segment 105b. Alternatively, the free end 100 can be fed through the second loop 99b in a first direction, folded so as to define the third loop 99c, and fed back through the second loop 99b in a second direction that is opposite the first direction. Accordingly, the first segment 105a extends from the first loop 99a, and the second segment 105b extends from the first segment 105a so as to define the third loop 99c. The free end 100 of the second end portion 54 extends distally from the second segment 105b, such that the free end 100 of the second end portion 54 and the third loop 99c are on opposite sides of the second loop 99b. Referring to FIG. 10E, the first segment 105a is tightened, which causes the size of the second loop 99b to decrease and tighten about the third loop 99c.

Figure 10F:
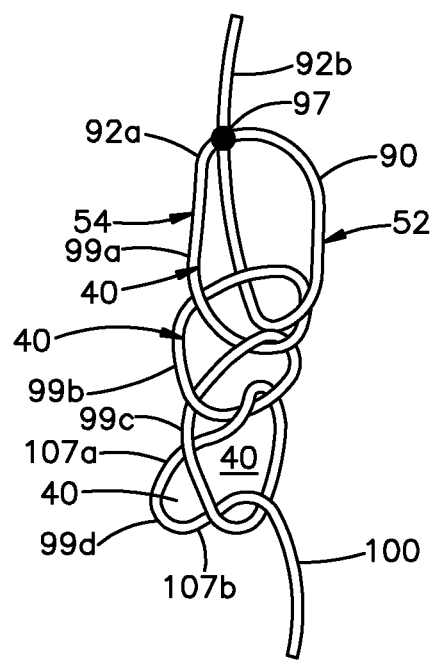
Figure 10G:
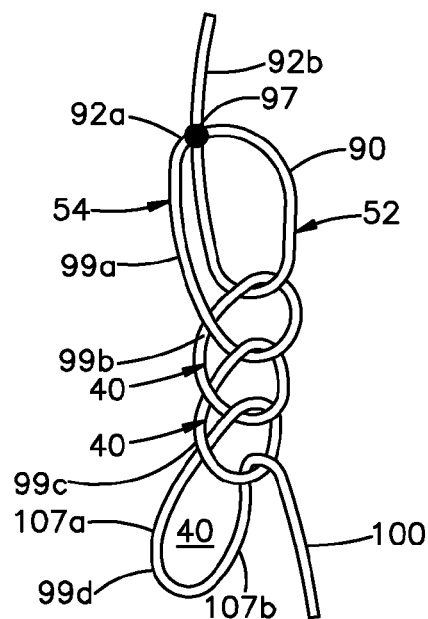

Next, as illustrated in FIG. 10F, the second end portion 54 can again be folded so as to define a new loop, such as a fourth loop 99d, that defines a respective opening 40 and includes a first segment 107a and a second segment 107b. The fourth loop 99d can be pulled through the opening 40 of a prior loop, such as the third loop 99c, such that the first segment 107a is disposed proximally with respect to the second segment 107b. Alternatively, the free end 100 can be fed through the third loop 99c in a first direction, folded so as to define the fourth loop 99d, and fed back through the third loop 99c in a second direction that is opposite the first direction. Accordingly, the first segment 107a extends from the second loop 99b, and the second segment 107b extends from the first segment 107a so as to define the fourth loop 99d. The free end 100 of the second end portion 54 extends distally from the second segment 107b, such that the free end 100 of the second end portion and the fourth loop 99d are on opposite sides of the third loop 99c. Referring to FIG. 10G, the first segment 107a is tightened, thereby causing the size of the third loop 99c to decrease and tighten about the fourth loop 99d.

Figure 10H:
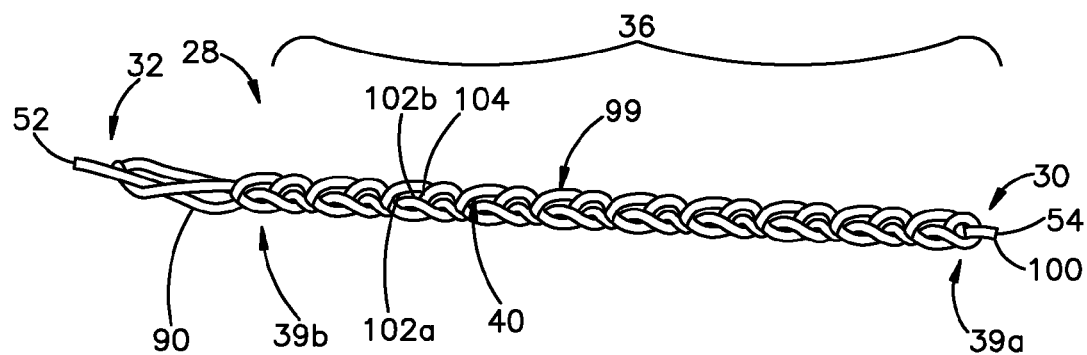

Thus, the method of creating the expandable portion 36, and thus the anchor body 28, can include repeated method steps of creating a prior loop, folding the second end portion 54 such that a subsequent loop 99 is disposed on one side of the prior loop and an end portion extends from the subsequent loop 99 on an opposite side of the prior loop, and applying tension to the first segment of the subsequent loop 99 so as to reduce the size of the prior loop. The method steps can be repeated so as to create as many loops 99 as desired, depending for instance on the desired length and expandability of the resulting anchor body 28 as illustrated in FIG. 10H. Once the final loop 99 has been created, the free end 100 of the second end portion 54 can be fed through the final loop and tightened so as to define a knot that closes the distal end 39b of the expandable portion 36. The remainder of the second end portion 54 can then be terminated at a location proximate to the distal end 39b of the expandable portion 36, or can extend proximally from the expandable portion so as to define an actuation strand 38 that is integral with the anchor body 28 and can be woven through select openings 40 as described above with respect to FIGS. 6A-7B, or can alternatively define an integral connector strand that is configured to attach the anchor 22 to another anchor. It should be appreciated that the final loop 99 can be devoid of an opening 40 in accordance with the illustrated embodiment. In one embodiment, the expandable portion 36 can include fifteen loops 99 each having an opening 40. In another embodiment, the expandable portion 36 can include eighteen loops 99 each having an opening 40. In still another embodiment, the expandable portion 36 can define eight openings 40.

While the anchor body 22 includes the expandable portion 36 and the eyelet 90 that can be constructed as described above, it should be appreciated that the expandable portion 36 and the eyelet 90 can be created using any suitable alternative method. For instance, the anchor body strand 44 can alternatively be braided in any alternative manner as desired so as to define the anchor body 28 having an expandable portion 36 that is configured to be actuated from the first configuration to the expanded configuration as described herein. Additionally, the expandable portion 36 can be created from the anchor body strand 44, the eyelet 90 can be fabricated from a strand that is separate or non-integral from the anchor body strand 44, and the eyelet 90 can be attached to the expandable portion 36, for instance using an adhesive, a splice, a knot, or any suitable alternative attachment. Thus, the eyelet 90 can be integral with the anchor body strand 44, and thus integral with the expandable portion 36, or can be separate or non-integral from and attached to the expandable portion 36. Furthermore, while the loops 56 of the expandable portion 36 can be constructed from the same anchor body strand 44, and thus are integral with each other in accordance with the illustrated embodiment, the expandable portion 36 can be include two or more anchor body strands that alone and/or in combination define braided segments or loops 56 that can be joined, for instance stitched (see FIG. 5C), welded (see FIG. 5D), tied, spliced, or otherwise attached together.

Figure 11A:
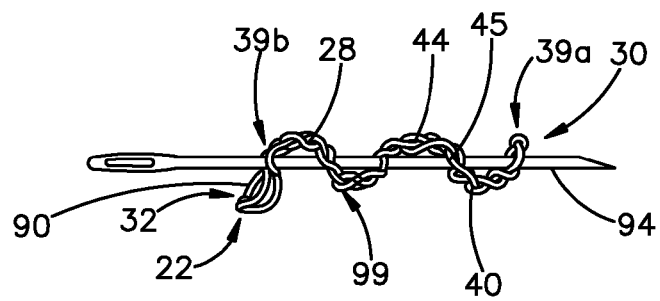
FIGS. 11A-B illustrate method steps of removably attaching of the actuation strand into the anchor body as illustrated in FIG. 8A.
Figure 11B:
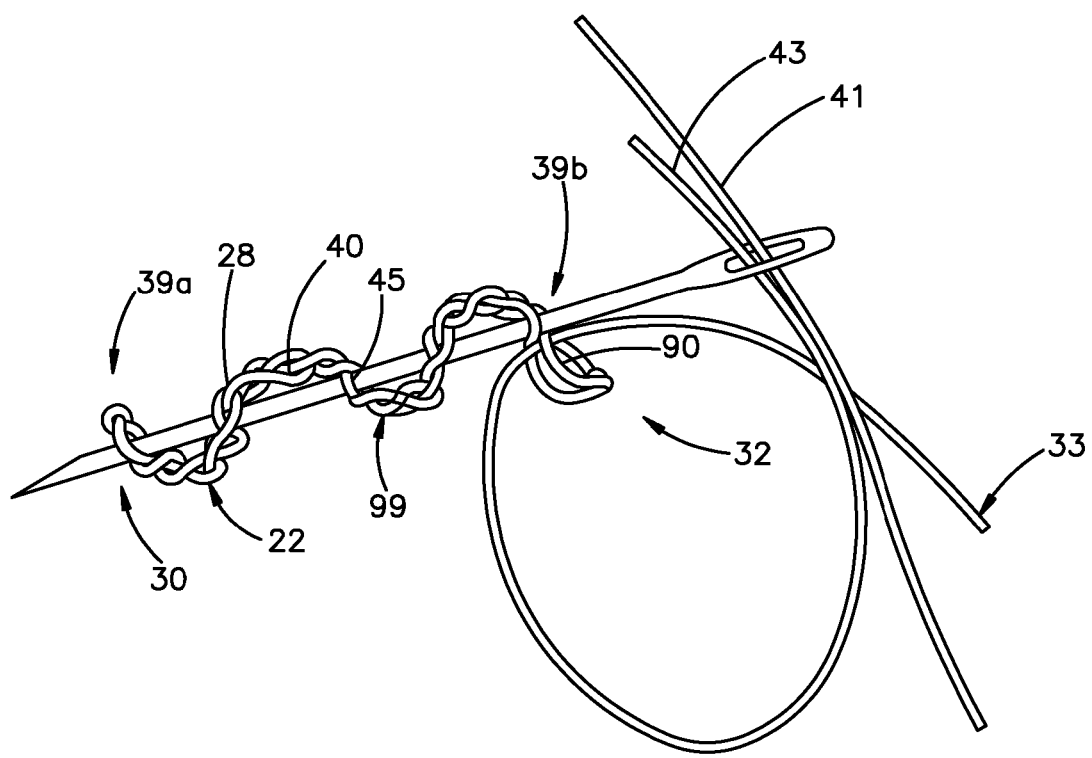

Referring now to FIGS. 11A-B, the auxiliary strand 33 can extend through the eyelet 90, and can further extend through at least a select opening 45 of the openings 40, such as a plurality of select openings 40, when the expandable portion 36 is in the first configuration. For instance, one of the first and second portions 41 and 43 of the auxiliary strand 33 can be fed through the eyelet 90. A needle, such as the needle 94 can be fed through the select openings 40 that have been identified as openings 40 that the auxiliary strand 33 is to extend through. The select openings 40 can be defined by any one or more, up to all, of the openings 40 of the expandable portion 36. For instance, the needle 94 can extend distally through the opening 40 of the second loop 99, and every fourth subsequent loop 99. The first and second portions 41 and 43 can be fed through the eye of the needle 94, and the needle 94 can be translated proximally through the expandable portion 36, thereby weaving the first and second portions 41 and 43 proximally from the eyelet 90 through at least one of the openings 40, such as each of the select openings 45. Once the eye of the needle 94 has passed through the expandable portion 36, the first and second portions 41 and 43 can be subsequently removed from the needle 94 as illustrated in FIG. 8A.

Referring now to FIGS. 10H and 11A-B, each of at least a plurality of the openings 40 up to all of the openings 40 is divided so as to define a first portion 102a and a second portion 102b adjacent the first portion 102a substantially along the second direction and separated by a strand 104 that extends through the opening 40 and is integral with the anchor body strand 44. In accordance with one embodiment, the first and second portions 41 and 43 extend alternatingly through a select one of the first and second portions 102a and 102b through the select openings 45 sequentially. Furthermore, the first and second portions 41 and 43 extend through the same portions 102a and 102b. For instance, the first and second portions 41 and 43 extend through a the same first one of the first and second portions 102a and 102b of the first select opening 45, through the same second one of the first and second openings 102a and 102b of the second select opening, and continue to alternate between the first and second portions 102a and 102b of the sequentially subsequent select openings.

Referring again to FIGS. 8A-C, it should be appreciated that the first and second portions 41 and 43 of the auxiliary strand 33 are attached to the eyelet 90, extend from the eyelet 90 through the same openings 40, extend through the same portions 102a and 102b of the openings 40, and extend out the anchor body 28, for instance proximally out the anchor body 28, and out the target anatomical location. Accordingly, the auxiliary strand 33, and in particular the first and second portions 41 and 43, define a travel path for the eyelet 90 when an actuation force F is applied to the auxiliary strand 33, and in particular to at least one of the first and second portions 41 and 43. Thus, at least one or both of the first and second portions 41 and 43 can define the actuation portion 131, and at least one or both of the first and second portions 41 and 43 can define the attachment portion 133. Accordingly, when the actuation force F is applied to at least one of the first and second portions 41 and 43 while the proximal end 39a of the expandable portion 36 is braced with respect to the actuation force F, the eyelet 90 travels proximally through the expandable portion 36, which causes the expandable portion 36 to actuate from the first configuration to the expanded configuration. The actuation force F can be applied to the auxiliary strand 33 until the eyelet 90 extends proximally from the expanded actuation body 36.

As will be described in more detail below, the eyelet 90 can define a connector member 63 that is configured to attach the anchor 22, directly or indirectly, to an to a second anchor. For instance, the auxiliary strand 33 of the anchor 22 can be attached, to the second anchor. For instance, the auxiliary strand 33 can be integral or separate from and attached to the actuation strand of the second anchor, directly or indirectly, or can alternatively be attached directly to the anchor body of the second anchor, for instance if the actuation strand is removed from the second anchor after the second anchor has been actuated from the first configuration to the expanded configuration. Alternatively, the auxiliary strand 33 can be removed from the anchor 22 and another strand, for instance an auxiliary strand of another anchor, can be inserted into the eyelet 90 so as to attach the anchor 22 to the other anchor and provide an actuation strand when the anchor 22 is implanted in the anatomical structure as described in more detail below.

Figure 12A:
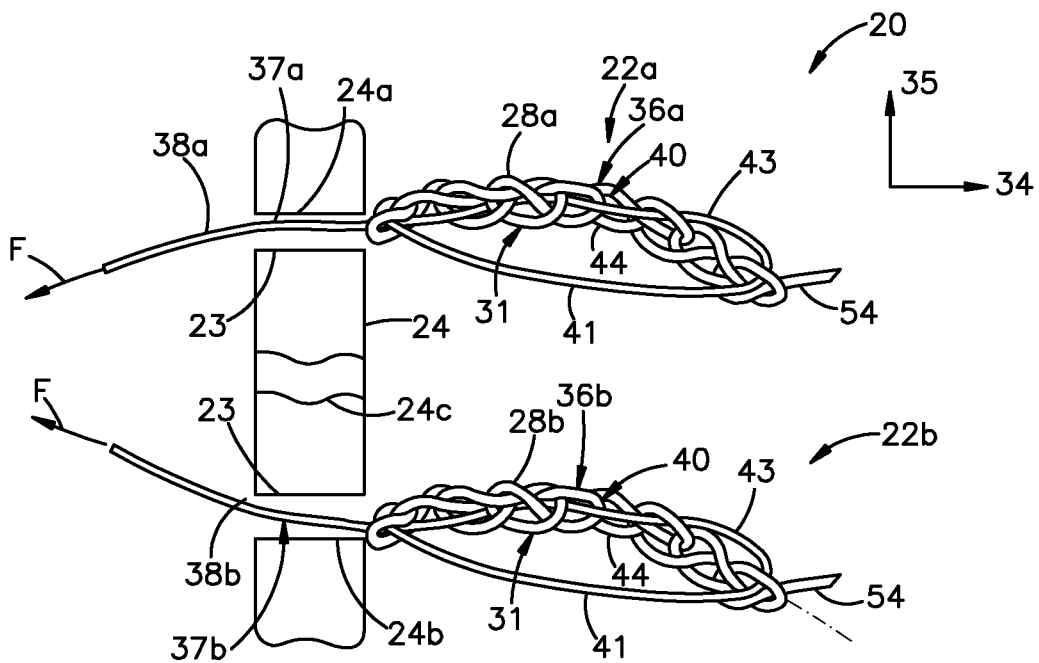
FIG. 12A is a side elevation view of an anchor assembly including first and second anchors shown in respective first configurations and implanted in an anatomical structure
Figure 12B:
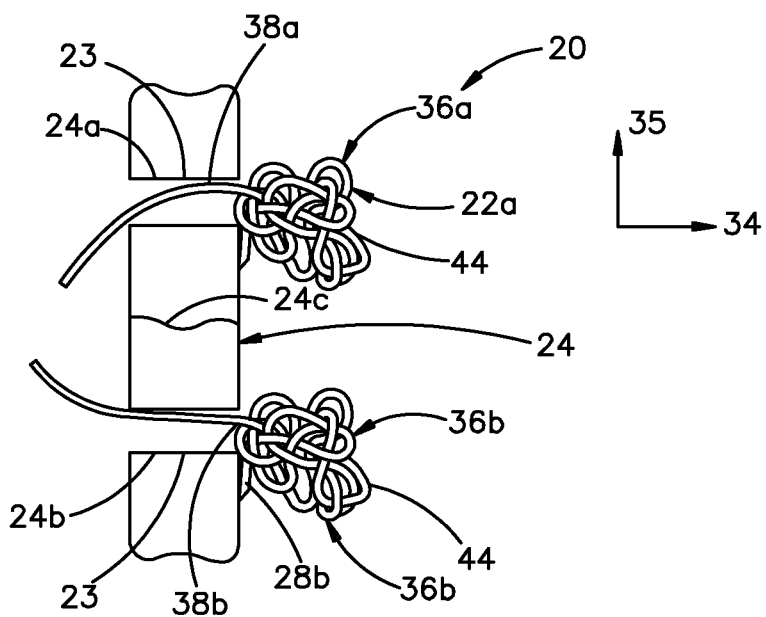
FIG. 12B is a side elevation view of the anchor assembly illustrated in FIG. 12A, showing the first and second anchors in respective expanded configurations.
Figure 12C:
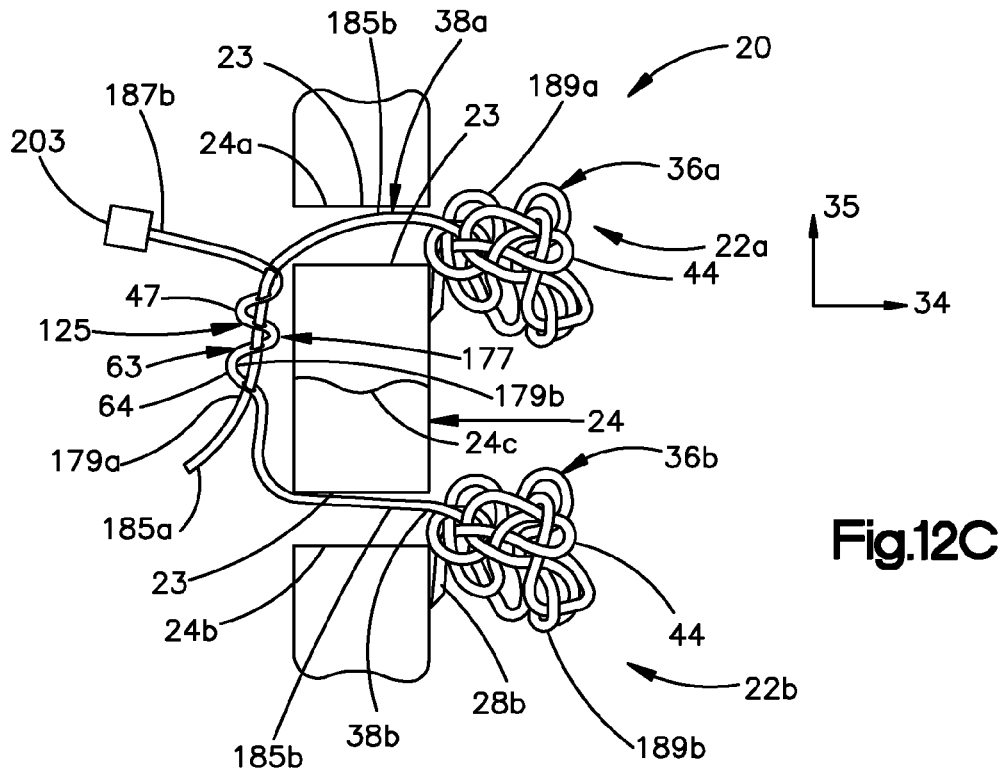
FIG. 12C is a side elevation view of the anchor assembly illustrated in FIG. 12B, including a schematically illustrated connector member that attaches the first anchor to the second anchor.

Referring now to FIGS. 12A-C, and as generally described above with respect to FIGS. 1A-B, the anchor assembly 20 can include first and second anchors 22a and 22b. The first anchor 22a includes a first anchor body 28a that extends substantially along the direction of elongation 34 and defines a first plurality of openings 40a that extend through the first anchor body 28a. The first anchor 22a further includes a first actuation strand 38a that extends through at least one of the openings 40a, such as a plurality of the openings, and is configured to receive an actuation force F that causes the first anchor body 28a to actuate from the first configuration to the expanded configuration in the manner described above. The first actuation strand 38a can be separate from and attached to, for instance woven through, the first anchor body 28a as described, for instance, with respect to FIGS. 2A-H, or can be integral with the first anchor body 28a as described above with respect to FIGS. 6A-C.

The second anchor 22b includes a second anchor body 28b that extends substantially along the direction of elongation 34 and defines a second plurality of openings 40b that extend through the second anchor body 28b. The second anchor 22b further includes a second actuation strand 38b that extends through at least one of the openings 40b, such as a plurality of the openings, and is configured to receive an actuation force F that causes the second anchor body 28b to actuate from the first configuration to the expanded configuration in the manner described above. The second actuation strand 38b can be separate from and attached to, for instance woven through, the second anchor body 28b as described above with respect to FIGS. 2A-H, or can be integral with the second anchor body 28b as described above with respect to FIGS. 6A-C.

Both the first anchor 22a and the second anchor 22b can include respective first and second anchor bodies 28a and 28b that include respective first and second expandable portions 36a and 36b that are configured to actuate from a first configuration to a second expanded configuration as described above. Both the first and second anchors 22 and 22b further include respective first and second actuation members 37a and 37b, such as actuation strands 38a and 38b.

In accordance with the embodiment illustrated in FIGS. 12A-B, the first and second actuation strands 38a and 38b are integral with the respective first and second anchor bodies 28a and 28b, and separate from, or non-integral with, each other. In accordance with other embodiments, the first and second actuation strands 38a and 38b are illustrated as separate from and attached to the respective first and second anchor bodies 28a and 28b (see FIGS. 14A-D). In accordance with still other embodiments, one of the first and second actuation strands 38a and 38b is integral with the respective anchor body and the other of the first and second actuation strands 38a and 38b is separate from and attached to the respective anchor body (see FIGS. 20A-B). In accordance with embodiments whereby the first and second actuation strands 38a and 38b are illustrated and described as integral with the respective first and second anchor bodies 28a and 28b, it should be appreciated that the first and second actuation strands 38a and 38b can alternatively be separate from and attached to the respective first and second anchor bodies 28a and 28b, unless otherwise indicated.

Furthermore, in accordance with embodiments whereby the first and second actuation strands 38a and 38b are illustrated and described as separate from and attached to the respective first and second anchor bodies 28a and 28b, it should be appreciated that the first and second actuation strands 38a and 38b can alternatively be integral with the respective first and second anchor bodies 28a and 28b, unless otherwise indicated. In accordance with still other embodiments, it should be appreciated that the first and second actuation strands 38a and 38b can be defined by a single auxiliary strand, and thus can be integral with each other (See, for instance, FIGS. 19A-B). The auxiliary strand can be woven through both of the anchor bodies 28a and 28b, or can be woven through one of the anchor bodies and integral with the other of the anchor bodies.

With continuing reference to FIG. 12C, the anchor assembly 20 can include at least one connector member 63 that is configured to join the anchors 22 and allow a biasing force to be applied to at least one of the anchors 22a and 22b that draws the anchors 22a and 22b together, thereby approximating the anatomical defect 24. The connector member 63 can be integral with one or both of the first and second anchors 22a and 22b, for instance integral with one or both of the first and second actuation strands 38a and 38b. At least one or both of the actuation strands, or a connector strand that can be attached to, for instance, the eyelet 90 (see, e.g., FIGS. 9A-9C) or any suitable alternative eyelet after the actuation strand 38 has been removed from the eyelet 90, is configured to receive an approximation force AF that biases at least one of the first and second anchors 22a and 22b toward the other so as to approximate the gap 24c.

As described above, each of the first and second anchor bodies 28a and 28b can be implanted at respective first and target anatomical locations 24a and 24b that are disposed, for instance, on opposite sides of an gap 24c as illustrated in FIG. 12A. Each of the first and second actuation strands 38a and 38b can receive an actuation force F substantially along the direction of elongation 34 that causes the respective first and second anchor bodies 28a and 28b, and in particular the respective first and second expandable portions 36a and 36b, to actuate from the first configuration to the expanded configuration so as to fix the first and second anchor bodies 28a and 28b at the respective first and second target anatomical locations 24a and 24b.

Referring now to FIG. 12B, once the first and second anchor bodies 28a and 28b are secured to the respective first and second target anatomical locations 24a and 24b, an approximation force AF can be applied to at least one or both of the first and second actuation segments 38a and 38b substantially along a direction toward the other of the respective first and second anchor bodies 28a and 28b, which can also be toward the respective gap 24c. Thus the approximation force AF can have a directional component that is toward the other of the respective first and second anchor bodies 28a and 28b, for instance can be directed purely toward the other of the first and second anchor bodies 28a and 28b. Likewise, the approximation force AF can have a directional component that is directed toward the gap 24c, for instance directed purely toward the gap 24c. Accordingly, the approximation force AF biases at least one or both of the anchor bodies 28a and 28b toward the other of the anchor bodies 28a and 28b to respective biased positions that to approximate the gap 24c.

Referring again to FIG. 12C, the connector member 63 that can define at least one of a sliding member 47 and a locking member 64 that attaches the first and second connector actuation strands 38a and 38b together, for instance at a junction 125. Thus, it should be appreciated that the at least one of the sliding member 47 and locking member 64 can likewise attach the first actuation strand 38a to the second actuation strand 38b. In accordance with one embodiment, the connector member 63 can attach the first and second actuation strands 38a and 38b after the first and second actuation strands 38a and 38b have been put under tension so as to maintain the gap 24c in an approximated state. The connector member 63 can be actuated to the locked configuration so as to prevent or resist separation of the first and second anchors 22a and 22b that would cause the gap 24c to open from the approximated state. Alternatively or additionally, the connector member 63 can attach the first and second actuation strands 38a and 38b to each other prior to applying the approximation force AF to the actuation strands 38a and 38b, and placing the actuation strands 38a and 38b under tension, and therefore prior to approximating the gap 24c.

Figure 13A:
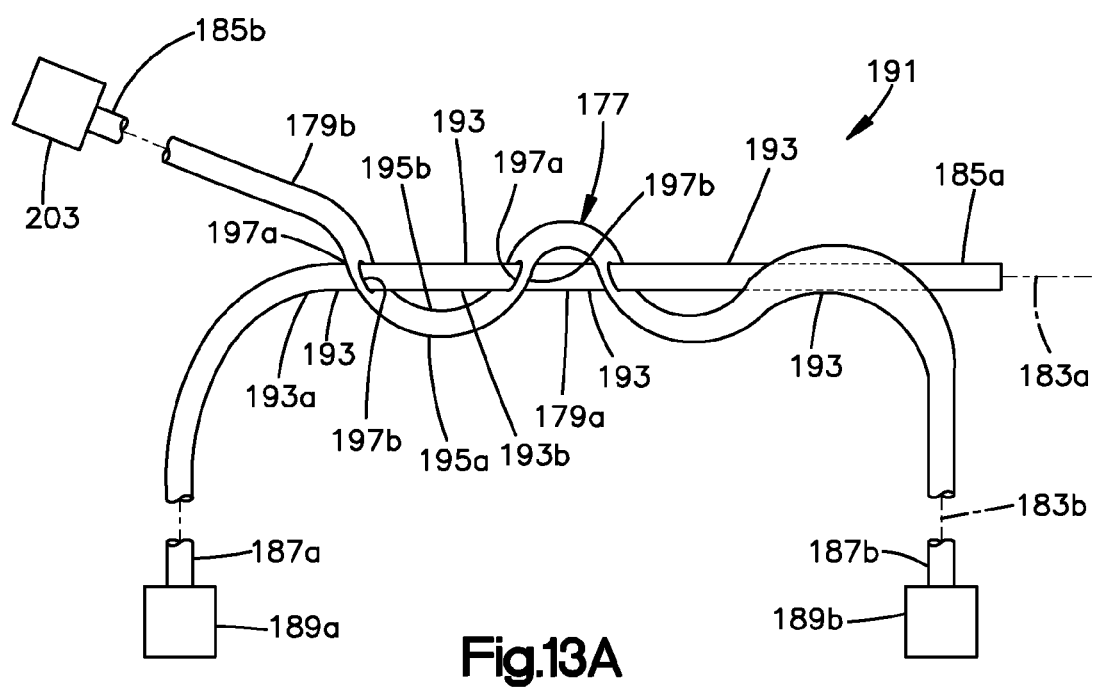
FIG. 13A is a side elevation view of a stitch lock assembly that defines the connector member illustrated in FIG. 12C configured as a stitch lock including first and second strand segments that are separate, and thus non-integral, with each other.

Referring now to FIG. 13A, in accordance with one embodiment, the connector member 63 can define a splice 134 in the form of a stitch lock 177 whereby at least a first segment of a strand, for instance of suture, also referred to as a first strand segment 179a that is elongate along a corresponding first central axis 183a is woven into, or through, a second segment of a strand, for instance of a suture, also referred to as a second strand segment 179b that is elongate along a corresponding second central axis 183b. The first and second strand segments 179a and 179b can be made from any suitable suture material as described herein, including polyester, ultra high molecular weight polyethylene, nylon, silk, or the like. Thus, the first strand segment 179a defines a first end 185a, which can be a free end that defines an actuation end configured to receive a tensile force, that extends out from a first side of the stitch lock 177. The first strand segment further defines a second end 187a, which can be a grounded end, extends out from a second side of the stitch lock 177 opposite the first side, such that the stitch lock 177 is disposed between the first end 185a and the second end 187a. The second end 187a of the first strand segment 179a can define an attachment location that can be attached to any first structure 189a as desired. Similarly, the second strand segment 179b defines a first end 185b, that extends out from a first end of the stitch lock 177, and a second end 187b that can extend out from a second end of the stitch lock that is opposite the first end. The stitch lock 177 is thus disposed between the first end 185b and the second end 187b. The second end 187b of the second strand segment 179b can be attached to a second structure 189b, and the first end 185b of the second strand segment 179b can be attached to a brace structure 203, so as to induce tension in the second strand segment 179b.

It should be appreciated that the first, second, and brace structures 189a-b and 203 can be configured as any suitable structure as desired, including any anatomical structure or any auxiliary structure that, for instance, can be attached to an anatomical structure. For instance, at least one up to all of the first, second, and brace structures 189a-b and 203 can be configured as one of the anchor bodies 28 of the type described herein. Thus, a stitch lock assembly 191 can include the first strand segment 179a that is configured to attach to the first structure 189a, and the second strand segment 179b that is configured to attach to the second structure 189b and the brace structure 203, whereby the first and second strand segments 179a-b define at least one stitch lock 177 constructed in any manner described herein. In accordance with certain embodiments, the stitch lock assembly 191 can include the structures 189*a-b* and 203 attached to the respective first and second strand segments 179*a-b*.

It should be appreciated that the structures 189*a-b* and 203 can be configured as anchor bodies as described above, or can alternatively be configured as any structure as desired. For instance at least one or both of the first and second structures can be defined by the human anatomy, such as a bone or soft tissue, including an annulus, or can be any alternatively structure as desired. Furthermore, the first and second structures can be integral with each other or separate from each other as desired. The first and second strand segments 179*a* and 179*b* can be attached to the respective structures 189*a-b* and 203 so as to be substantially translatably attached to (either separately attached or integral with) the structures 189*a-b* and 203 as illustrated, such that the strand segments 179*a-b* are fixed to the structures 189*a-b* and 203, or can be attached in any suitable alternative manner as desired.

The present inventors were surprised to discover that the stitch lock 177 is configured to iterate between an unlocked configuration and a locked configuration. When the stitch lock 177 is in the unlocked configuration, the first strand segment 179*a* is able to translate through the second strand segment 179*b* along a first direction that biases the first and second structures 189*a* and 189*b* toward each other. When the stitch lock 177 is in the locked configuration, the stitch lock 177 prevents the first strand segment 179*a* from translating through the second strand segment 179*b* along a second direction opposite the first direction that would allow the first and second structures 189*a* and 189*b* to separate from each other, even when the stitch lock 177 is constructed having a short length. Once the stitch lock 177 has been actuated from the unlocked configuration to a locked configuration, the stitch lock 177 prevents the first strand segment 179*a* from translating through the second strand segment 179*b* along both the first and second directions. For instance, the locked stitch lock 177 prevents the first strand segment 179*a* from translating through the second strand segment 179*b* whether a static load tensile load is applied the second end 187*a* of first strand segment 179*a*, or a cyclical load is applied to the second end 187*a* of the first strand segment 179*a* during normal anatomical function.

As will be described in more detail below in accordance with certain embodiments, at least one up to all of the first and second structures 189*a-b* and 203 can be configured as anchor bodies of any of the types described herein. When the first and second structures 189*a-b* are configured as first and second anchor bodies 28*a-b* respectively, translation of the first strand segment 179*a* through the second strand segment 179*b* along the first direction can draw the first and second anchors bodies 28*a* and 28*b* toward each other so as to approximate the gap 24*c*. Prevention of the first strand segment 179*a* from translating through the second strand segment 179*b* along the second direction maintains the gap 24*c* in the approximated state and prevents the gap 24*c* from opening. The present inventors have found that conventional sliding knots, such as those commonly known as hangman's knots, noose knots, and inside clinch knots, allow at least one of the stands to slide in both a first direction and a second direction that is opposite the first direction, which could thus allow the gap 24*c* to re-open once approximated.

The stitch lock 177 can be constructed as a woven construct whereby the first strand segment 179*a* defines a plurality of woven segments 193 that are woven at least into, for instance through, the second strand segment 179*b*. For instance, the first strand segment 179*a* can be woven at least into the second strand segment 179*b* along a direction from the first end 185*b* of the second strand segment 179*b* toward the second end 187*b* of the second strand segment 179*b* (e.g., away from the corresponding first structure 189*a*). Alternatively, the first strand segment 179*a* can be woven at least into the second strand segment 179*b* along a direction from the second end 187*b* of the second strand segment 179*b* toward the first end 185*b* of the second strand segment 179*b*.

With continuing reference to FIG. 13A, the first strand segment 179*a* defines a first woven segment 193*a* that extends at least into, for instance through, the second strand segment 179*b* along a first direction having a first directional component. For instance, the first woven segment 193*a* can extend into a first side 195*a* of the second strand segment 179*b* at an entry location 197*a* of the second strand segment 179*b*, and can further extend through the second strand segment 179*b* so as to exit from a second side 195*b* of the second strand segment 38 at an exit location 197*b* of the second strand segment 179*b*. The first strand segment 179*a* can define a second woven segment 193*b* that extends at least into, for instance through, the second strand segment 179*b* at a location spaced from the first woven segment 193*a* along the second central axis 183*b* of the second strand segment 179*b*. The second woven segment 193*b* can extend at least into, for instance through, the second strand segment 179*b* along a second direction having a second directional component that is opposite the first directional component of the previous, or first, woven segment. Thus, the second direction can be opposite the first direction or otherwise angularly offset with respect to the first direction. For instance, in one embodiment, the second woven segment 193*b* can extend along the second direction into the second side 195*b* of the second strand segment 179*b* so as to define the corresponding entry location 197*a*, and can further extend through the second strand segment 179*b* so as to exit from the first side 195*a* of the second strand segment 179*b* at the corresponding exit location 197*b*. Alternatively, the exit location 197*b* of at least one or more of the woven segments 193 can be disposed on the same side as the corresponding entry location 197*a*. The entry location 197*a* of the second woven segment 193*b* can be spaced from the entry location 197*a* of the first woven segment 193*a* along the second central axis 183*b* of the second strand segment 179*b* in a direction from the second end 187*a* toward the first end 185*a* of the first strand segment 179*a*.

Thus, the first strand segment 179*a* defines a plurality of woven segments 193 that can each be defined by the first strand segment 179*a* at a location between adjacent entry locations 197*a*. The first strand segment 179*a* can define as many woven segments 193 as desired, such as greater than one. At least one up to all of the woven segments 193 extend through the second strand segment 179*b* along a respective direction that includes a directional component that is opposite the directional component of an adjacent one of the woven segments 193. It should be further appreciated that the woven segments 193 can cross the plane that includes the second central axis 183*b* of the second strand segment 179*b*, and can furthermore cross the second central axis 183*b* of the second strand segment 179*b*. The entry locations 197*a* of at least one up to all of the woven segments 193 can be spaced from the entry locations 197*a* of adjacent ones of the woven segments 193 along a direction substantially parallel to the second central axis 183*b* of the second strand segment 179*b*.

Furthermore, the exit location 197*b* at least one up to all of the woven segments 193 can be spaced from the corresponding entry location 197*a* along the second central axis 183*b* of the second strand segment 179*b* as desired. Alternatively or additionally, the exit location 197b of at least one up to all of the woven segments 193 can be aligned with the corresponding entry location 197a with respect to the central axis 183b of the second strand segment 179b. Thus, it should be appreciated that the first central axis 183a of the first strand segment 179a can define any angle as desired with respect to the second central axis 183b of the second strand segment 179b as desired at the exit location 197b, between and including approximately 0 degrees and approximately 180 degrees, including approximately 90 degrees. For instance, the first central axis 183a of the first strand segment 179a can define an angle of approximately zero degrees (or approximately 180 degrees) with respect to the second central axis 183b of the second strand segment 179b when the first strand segment 179a extends substantially along the second central axis 183b as the first strand segment 179a is disposed in the second strand segment 179b. The first strand segment 179a can exit the second strand segment 179b at the same side of the second strand segment 179b in which it entered, or in an opposite side of the second strand segment 179b in which it entered.

It should be further appreciated that the angle defined at the entry location 197a of a given woven segment 193 can be the same angle or a different angle that is defined at the corresponding exit location 197b. Thus, the woven segments 193 can be symmetrically arranged along the length of the second strand segment 179b, or can be asymmetrically arranged along the length of the second strand segment 179b. In accordance with one embodiment, the first and second sides 185a-b, and thus the entry location 197a and the exit location 197b of a given woven segment 193, can be disposed on opposite sides of a plane that includes the second central axis 183b of the second strand segment 179b. Adjacent woven segments 193 can extend through the second strand segment 179b at locations spaced from each other at any distance as desired along the second central axis 183b of the second strand segment 179b, for instance between and including approximately 0 mm and approximately 3 mm.

In accordance with the illustrated embodiment, the first strand segment 179a can extend substantially straight through the second strand segment 179b so as to define the stitch lock 177, and the second strand segment 179b can be kinked so as to define folded segments between adjacent entry locations 197a, and thus also between adjacent exit locations 197. During operation, when the tension in the second strand segment 179b is at a first level of tension less than a threshold tension level defined by the stitch lock 177, the stitch lock 177 is in an unlocked configuration whereby the first strand segment 179a can translate through the second strand segment 179b, for instance along a direction from the second end 187a toward the first end 185a. When the tension in the second strand segment 179b reaches a second level of tension that is greater than the threshold tension level defined by the stitch lock 177, the stitch lock 177 actuates to a locked configuration whereby the first strand segment 179a is prevented from translating through the second strand segment 179b, for instance along a direction from the second end 187a toward the first end 185a.

For instance, referring to FIGS. 13B-C, when a tensile force is applied to the first and second ends 185b and 187b, thus placing the second strand segment 179b in tension, the second strand segment 179b applies a compressive force CF to at least one up to all of the woven segments 193 of the first strand segment 179a. The compressive force CF can be applied to the first strand segment 179a along a direction substantially perpendicular to the first central axis 183a of the first strand segment 179a or angularly offset with respect to the central axis 183a. As the compressive force CF increases, frictional engagement between the first and second strand segments 179a and 179b likewise increases, which resists movement of the first strand segment 179, for instance at the woven segments 193, through the second strand segment 179b. It should be appreciated that the cumulative compressive force CF applied by the second strand segment 179b to the first strand segment 179a can be directly proportional to the number of woven segments 193 defined by the first strand segment 179a. Thus, as the number of woven segments 193 of the stitch lock 177 increases, the compressive force CF increases at a given tension of the second strand segment 179b. When the second strand segment 179b is in tension at a level of tension at the stitch lock 177 that is at least substantially equal to a threshold level of tension defined by the stitch lock 177, the locked configuration of the stitch lock 177 causes the compressive force CF to prevent the first strand segment 179a from translating relative to the second strand segment.

In accordance with the illustrated embodiment, as the stitch lock 177 actuates to the locked configuration, the stitch lock 177 inverts as illustrated in FIGS. 13B-C, whereby the second actuation strand 179b straightens to a substantially straight configuration (for instance, more straight than when in the stitch lock 177 is in the unlocked configuration) and the first actuation strand 179a becomes kinked about the first actuation strand 179b (for instance more kinked than when the stitch lock 177 is in the unlocked configuration).

When the second strand segment 179b is in tension at a first level that is less than a threshold level of tension (which includes a circumstance where the second strand segment is not in any tension, such that the first level of tension is zero), the stitch lock 177 is in an unlocked configuration, such that woven segments 193 of the first strand segment 179a can travel through the second strand segment 179b, for instance along a first direction from the second end 187a to the first end 185a when a tensile force is applied to the first end 185a, such that the first end 185a translates away from the stitch lock 177. Thus, it should be appreciated that the stitch lock 177 defines a sliding member that permits the first strand segment 179a to translate through the second strand segment 179b when the stitch lock 177 is in the unlocked configuration.

Once the tension of the second strand segment 179b at the stitch lock 177 increases from the first level of tension to a second level of tension that is at least substantially equal to the threshold level of tension, the stitch lock 177 transitions to the locked configuration, such that the compressive force CF of the second strand segment 179b about the first strand segment 179a provides a locking force that produces a frictional engagement between the first and second strand segments 179a-b that prevents the woven segments 193 of the first strand segment 179a from translating through the second strand segment 179b at the stitch lock 177, both along the first direction, and along the second direction opposite the first direction from the first end 185a toward the second end 187a, such that the first end 185a is prevented from translating toward the stitch lock 177. It should thus be appreciated that the stitch lock 177 can define a locking member that prevents the first strand segment 179a from translating through the second strand segment 179b when the stitch lock is in the locked configuration.

Referring now to FIG. 13D, the stitch lock assembly 191 can further include a tension relief instrument 199. For instance, if it is desired to further translate the first strand segment 179a through the second strand segment 179b along the second direction after the stitch lock 177 has been locked, the tension relief instrument 199 can releasably attach to the, for instance abut, the second strand segment 179b so as to decrease the tension of the second strand segment 179b at the stitch lock 177 to a level that is less than the threshold level. For instance, the tension relief instrument 199 can include a handle 199a and an engagement member 199b that extends from the handle 199a. The engagement member 199b is configured to operably engage the stitch lock 177 so as to decrease the tension of the second strand segment 179b to a level less than the threshold level of tension. In accordance with one embodiment, the engagement member 199 can releasably abut the second strand segment 179b at a location 201 adjacent the stitch lock 177, and the handle 199a can be actuated so as to translate the location 201 toward the stitch lock 177 so as to decrease the level of tension in the second strand segment 179b at the stitch lock 177, which allows the woven segments 193 of the first strand segment 179a to travel through the second strand segment 179b, for instance along the first direction or the second direction. Thus, the tension relief instrument 199 can apply a compressive force to the second strand 179b of the stitch lock 177 while a tensile force is applied to the first end 185a of the first strand segment 179a so as to allow the first strand segment 179a to travel through the second strand segment 179b at the stitch lock 177. Once the first strand segment 179a has translated a desired distance, the tension relief instrument 199 can be disengaged from both the first strand segment 179a and the second strand segment 179b. If the tension in the second strand segment 179b is greater than the threshold level once the tension relief instrument has been disengaged from the second strand segment, the compressive force applied by the second strand segment 179b against the first strand segment 179a prevents the woven segments 193 of the first strand segment 179a from translating through the second strand segment 179b at the stitch lock 177 as described above.

During operation, the second strand segment 179b can be placed in tension at a level that is substantially equal to the threshold level of tension. The tension relief instrument 199 can be coupled to the stitch lock 177 so as to release tension in the second strand segment 179b to a level less than the threshold level of tension, and a tensile force can be applied to the first or free end 185a of the first strand segment 179a so as to cause the first strand segment 179a to translate relative to the second strand segment 179b. As the first strand segment 179a translates relative to the second strand segment 179b, the first structure 189a is drawn along a direction that can be defined by the central axis 183b of the second strand segment 179b at the stitch lock 177. Thus, when the central axis 183b of the second strand segment 179b extends along a direction that includes a directional component toward the second structure 189b (for instance when the central axis 183 at the stitch lock 177 defines a direction that is oblique to the central axis 183 at the second end 187b), the first structure 189a can move along a direction toward the second structure 189b. If the central axis 183b of the second strand segment 179b extends substantially perpendicular to the second end 187b of the second strand segment 179b, the first structure 189a can move along a direction tangential to the second structure 189b.

Referring now to FIG. 12C, the connector member 63 can define at least a first stitch lock 177 that is defined by the first and second actuation strands 38a and 38b. The stitch lock 177 can be constructed after the anchors 22a and 22b have been implanted into the respective target anatomical locations 24a and 24b before they are expanded or after they have been expanded. Alternatively still, stitch lock 177 can join the anchors 22a and 22b, and the anchor assembly 20 can be packaged and provided to the surgeon, such that the anchors 22 and 22b are pre-connected with the stitch lock 177 prior to inserting the anchor bodies 28a and 28b into the respective target anatomical locations 24a and 24b.

The first strand segment 179a of the first stitch lock 177 can be defined by one of the first and second actuation strands 38a and 38b, and the second strand segment 179b of the first stitch lock 177 can be defined by the other of the first and second actuation strands 38a and 38b. In accordance with the illustrated embodiment, the first strand segment 179a is defined by the first actuation strand 38a, and the second strand segment 179b is defined by the second actuation strand 38b. Furthermore, the first structure 189a is defined by the first anchor body 28a, and the second structure 189b is defined by the second anchor body 28b. Alternatively, the first strand segment 179a can be defined by the second actuation strand 38b, and the second strand segment 179b can be defined by the first actuation strand 38a. In accordance with the illustrated embodiment, the first actuation strand 38a is woven at least into, for instance through, the second actuation strand 38b at the stitch lock 177 along a direction from the second anchor body 28b toward the first anchor body 28a. Alternatively, the second actuation strand 38b can be woven at least into, for instance through, the first actuation strand 38a at the stitch lock 177 along a direction from the first anchor body 28a toward the first anchor body 28b.

During operation, once the anchor bodies 28a and 28b have been inserted into the respective first and second target anatomical locations 24a and 24b and expanded from their respective first configurations to their respective second configurations, a tensile approximation force AF can be applied to the first ends of the first and second segment strands 38a and 38b, which biases the corresponding anchor bodies 28a and 28b, and the corresponding first and second target anatomical locations 24a and 24b, toward the stitch lock 177. Because the stitch lock 177 is disposed between the first and second anchor bodies 28a and 28b, the approximation force AF draws the anchor bodies 28a-b, and the corresponding target anatomical locations 24a and 24b, toward each other so as to approximate the gap 24c. Once first actuation strand 38a, which defines the second strand segment 179b in accordance with the illustrated embodiment, is placed in tension, for instance between the anchor body 28a and the brace structure 203, at a level that is substantially equal to the threshold level of tension, the first actuation strand 38a, which defines the first strand segment 179a in accordance with the illustrated embodiment, is prevented from translating through the second actuation strand 38b at the stitch lock 177 both in a first direction that would further draw the first anchor body 28a toward the second anchor body 28b, and in a second direction that would allow the first anchor body 28a to separate with respect to the second anchor body 28b. Thus, if it is further desired to draw the anchor bodies 28a-b toward each other, the tension relief instrument 199 (see FIG. 13C) can engage the second actuation strand 38b in the manner described above so as to reduce the tension in the first actuation strand at the stitch lock 177 to a level that is less than the threshold level, thereby allowing the first actuation strand 38a to translate through the second actuation strand 38b along the first direction as described above. The brace structure 203 can be disposed in a third anatomical location, or can be configured as a third anatomical location, or can be disposed at the target location 24.

It should be further appreciated that the first and second actuation strands 38a-b can define a second stitch lock that is spaced from the first stitch lock as desired. For instance, the first stand segment of the second stitch lock can be defined by the actuation strand that defines the second strand segment 179b of the first stitch lock 177, and the second strand segment of the second stitch lock can be defined by the actuation strand that defines the first strand segment 179a of the first stitch lock 177. Alternatively, the first stand segment of the second stitch lock can be defined by the actuation strand that defines the first strand segment 179a of the first stitch lock 177, and the second strand segment of the second stitch lock can be defined by the actuation strand that defines the second strand segment 179b of the first stitch lock 177.

While the stitch lock 177 has been illustrated above with respect to FIGS. 12A-C as being defined by first and second actuation strands 38a and 38b that are integral with the respective first and second anchor bodies 28a and 28b, it should be appreciated that the stitch lock 177 can alternatively be defined by first and second actuation strands 38a and 38b that are separate from each other, and also separate from, and connected to, the respective first and second anchor bodies 28 and 28b.

Figure 14A:
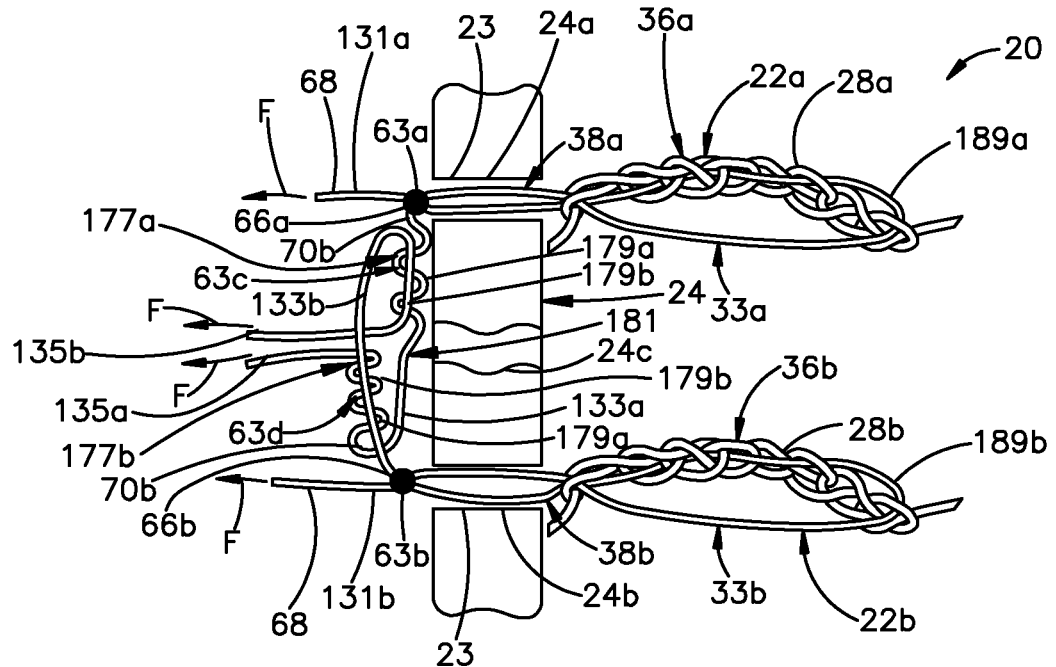
FIG. 14A is a side elevation view of an anchor assembly constructed in accordance with another embodiment, including first and second anchors shown in respective first configurations and implanted in an anatomical structure.
Figure 14B:
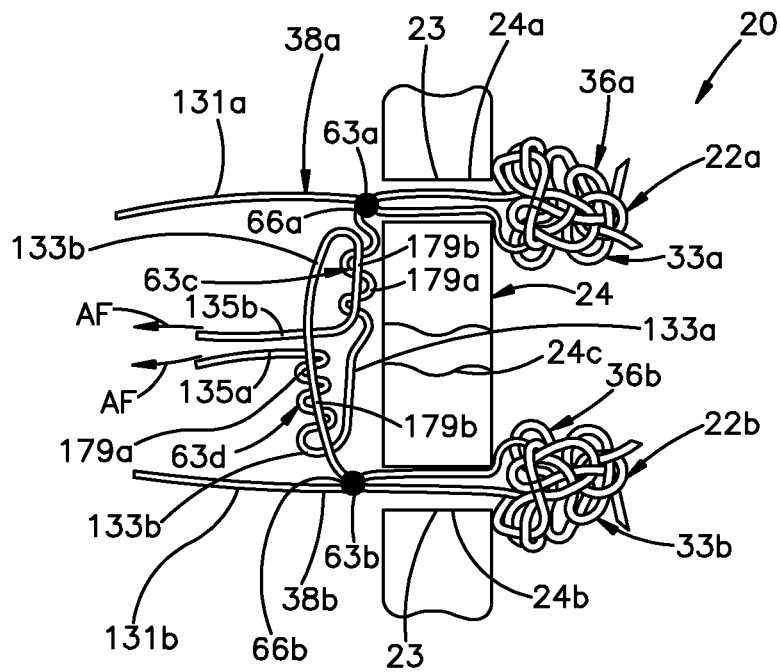
FIG. 14B is a side elevation view of the anchor assembly illustrated in FIG. 14A, showing the first and second anchors in respective expanded configurations.

For instance, referring now to FIGS. 14A-B, the anchor assembly 20 can include a first auxiliary strand 33a that defines the first actuation strand 38a, and a second auxiliary strand 33b that defines the second actuation strand 38b and is separate from the first auxiliary strand 33a. The first strand segment 177a can be defined by the second actuation strand 38b, and the second strand segment 177b can be defined by the first actuation strand 38a. Accordingly, the first and second attachment portions 133a and 133b can be separate from each other. The anchor assembly 20 can include at least one connector member, such as first and second connector members 63a-b that can attach the actuation portions 131a and 131b to the respective attachment portions 133a and 133b as described above. For instance, the first and second connector members 133a and 133b can be configured as knots 66 that define sliding members and locking members, for instance as described above with respect to FIGS. 2C and 2F. The anchor assembly 20 can further include at least one connector member, such as a pair of third and fourth connector members 63c-d, that are configured to attach the actuation strands 38a and 38b, such as the attachment portions 133a and 133b, and thus the first and second anchors 22a and 22b, to each other.

In accordance the illustrated embodiment, the third and fourth connector members 63c and 63d can be configured as respective first and second stitch locks 177a and 177b, defined by the first and second auxiliary strands 33a and 33b, that join the first structure 189a that is configured as the first anchor body 28a to the second structure 189b that is configured as the second anchor body 28b. For instance, the first attachment portion 133a extends from the first connector member 63a toward the second connector member 63b, and thus also extends toward the second attachment portion 133b. Likewise, the second attachment portion 133b extends from the second connector member 63b toward the first connector member 63a, and thus also extends toward the first attachment portion 133a.

In accordance with the illustrated embodiment, the first stitch lock 177a is defined by the first and second actuation strands 38a and 38b, such that the second actuation strand 38b, for instance at the second attachment portion 133b, defines the first strand segment 179a, and the first actuation strand 38a, for instance at the first attachment portion 133a, defines the second strand segment 179b. Thus, the second actuation portion 133b, is woven at least into, such as through, the first actuation strand 38a, and in particular the first attachment portion 133a, so as to define the first stitch lock 177a in the manner described above. The second attachment portion 133b can define the woven segments of the first stitch lock 177a. In accordance with the illustrated embodiment, the second attachment portion 133b is woven through the first attachment portion 133a along a direction from the second end of the first attachment portion 133a toward the first end of the first attachment portion 133a, and thus also along a direction from the first anchor body 28a toward the second anchor body 28b. It should be appreciated, however, that the second attachment portion 133b can be woven through the first attachment portion 133a along a direction from first end of the first attachment portion 133a toward the second end of the first attachment portion 133a, and thus also along a direction from the second anchor body 28b toward the first anchor body 28a. The second attachment portion 133b can exit the first attachment portion 133a so as to define a second terminal portion 135b.

In accordance with the illustrated embodiment, the second stitch lock 177b that defines the fourth connector member 63d is defined by the first and second actuation strands 38a and 38b, such that the first actuation strand 38a, for instance at the first attachment portion 133a, defines the first strand segment 179a, and the second actuation strand 38b, for instance at the second attachment portion 133b, defines the second strand segment. Thus, the first actuation strand 38a, for instance at the first attachment portion 133a, is woven at least into, such as through, the second actuation strand 38b, for instance at the second attachment portion 133b, so as to define the second stitch lock 177b. The first attachment portion 133a can define the woven segments of the second stitch lock 177b. In accordance with the illustrated embodiment, the first attachment portion 133a is woven through the second attachment portion 133b along a direction from the second end of the second attachment portion 133b toward the first end of the second attachment portion 133b, and thus also along a direction from the second anchor body 28b toward the first anchor body 28a. It should be appreciated, however, that the first attachment portion 133a can be woven through the second attachment portion 133b along a direction from the second end of the second attachment portion 133b toward the first end of the second attachment portion 133b, and thus also along a direction from the first anchor body 28a toward the second anchor body 28b. The first attachment portion 133a can exit the second attachment portion 133b so as to define a first terminal portion 135a.

In accordance with the illustrated embodiment, the first and second stitch locks 177a and 177b can define a loop 181 that defines an area. The loop 181 is closed by the first and second stitch locks 177a and 177b. When at least one or both of the first strand segments 179a are placed in tension and translated through the respective strand segments 179b, the loop 181 decreases in size, thereby decreasing the area until tension is induced in the second strand segments 179b at a level that is substantially equal to the threshold tension level that causes the respective stitch locks 177a-b to actuate to their respective locked configurations.

The first terminal portion 135a is spaced from the second terminal portion 135b. For instance, the second terminal portion 135b can be disposed closer to the first anchor body 28a than the first terminal portion 135a, and the first terminal portion 135a can be spaced closer to the second anchor body 28b than the second terminal portion 135b, though it should be appreciated that the first and second terminal portions 135a and 135b can be spaced in so as to define any suitable spatial relationship with respect to each other and the first and second anchor bodies 28a and 28b as desired. For instance, the anchor assembly 20 can further include any suitable connector member, such as a stitch lock 177, that attaches the first and second terminal portions 135a and 135b together.

During operation, the first and second knots 66a-b can be in respective unlocked configurations such that application of the actuation force F to each of the first and second actuation portions 131a-b causes the respective first and second anchor bodies 28a-b to actuate from the first configuration to the expanded configuration. Next, a tensile locking force can be applied to the first and second attachment portions 133a-b so as to lock the first and second knots 66a-b in the manner described herein.

Figure 14C:
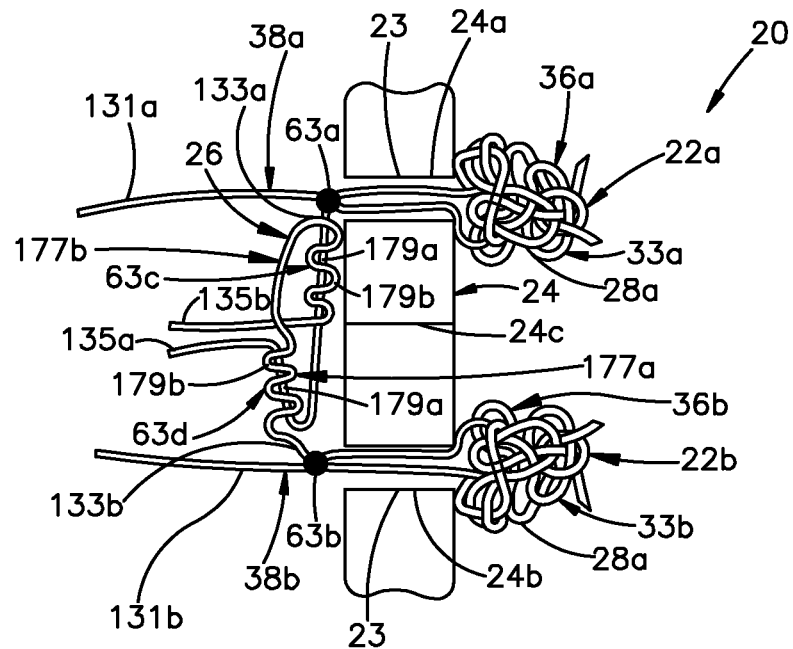
FIG. 14C is a side elevation view of the anchor assembly illustrated in FIG. 14B, showing the first and second anchors in an approximated configuration.
Figure 14D:
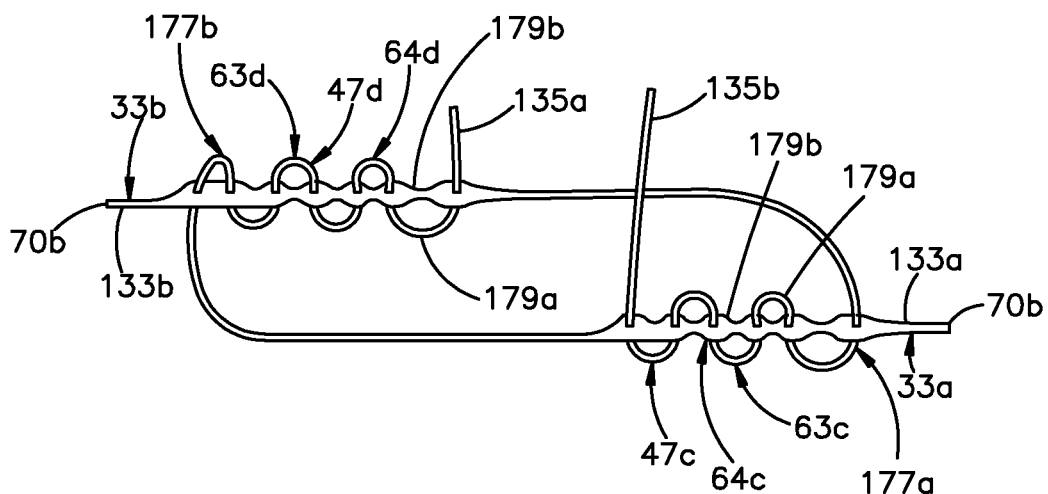
FIG. 14D is an enlarged portion of the anchor assembly illustrated in FIG. 14C.

In accordance with the illustrated embodiment, referring to FIGS. 14C-D, the approximation force AF is applied to the first and second terminal portions 135a-b of the first and second actuation strands 38a and 38b. When the approximation force AF is applied to the second terminal portion 135b, the second attachment portion 133b of the second actuation strand 38b translates through the first attachment portion 133a of the first actuation strand 38a at the at the first stitch lock, thereby decreasing the size of the loop 181. It should be appreciated that the first and second structures 189a and 189b are attached to the respective first and second strand segments 79a and 79b at the respective attachment locations of the second strand segments 79a and 79b at locations spaced from, and thus outside, the loop 181. Thus, the loop 181 can be disposed between the respective attachment locations and thus between the first and second structures 189a-b. When the approximation force AF is applied to the first terminal portion 135a, the first attachment portion 133a of the first actuation strand 38a through the second attachment portion 133b of the second actuation strand 38b at the second stitch lock 177b. The approximation force AF induces tension in the first and second actuation strands 38a and 38b so as to apply the locking force to the free portions 70b of the knots 66 of the respective first and second connector members 63a and 63b, thereby actuating the knots 66 to the locked configurations. Thus, the approximation force AF can define the locking force for the knots 66.

Furthermore, the tension induced in the first and second actuation strands 38a and 38b biases at least one or both of the first and second anchors 22a and 22b toward the other, thereby approximating the gap 24c. It should be appreciated that when the tension induced in the first actuation strand 38a, for instance at the first attachment portion 133a, is substantially equal to the threshold level of tension in response to application of the approximation force AF to the respective first terminal portion 135a, the first stitch lock 177a can actuate to the locked configuration, whereby the first attachment portion 133a applies a compressive force to the second attachment portion 133b. The compressive force prevents the second attachment portion 133b from further translating through the first attachment portion 133a at the first stitch lock 177a. Similarly, when the tension induced in the second actuation strand 38b, for instance at the second attachment portion 133b, is substantially equal to the threshold level of tension in response to application of the approximation force AF to the respective second terminal portion 135b, the second stitch lock 177b can actuate to the locked configuration, whereby the second attachment portion 133b applies a compressive force to the first attachment portion 133a. The compressive force prevents the first attachment portion 133a from further translating through the second attachment portion 133b at the second stitch lock 177b.

While each of the first and second connector members 63a and 63a is configured as a knot 66, whereby one of the first and second actuation strands 38a-b is tied to the other of the first and second actuation strands 38a-b, it should be appreciated that the first and second connector members 63a and 63b can be configured as stitch locks that are configured to attach the first and second actuation portions 131a-b to the respective first and second attachment portions 133a-b.

Figure 15A:
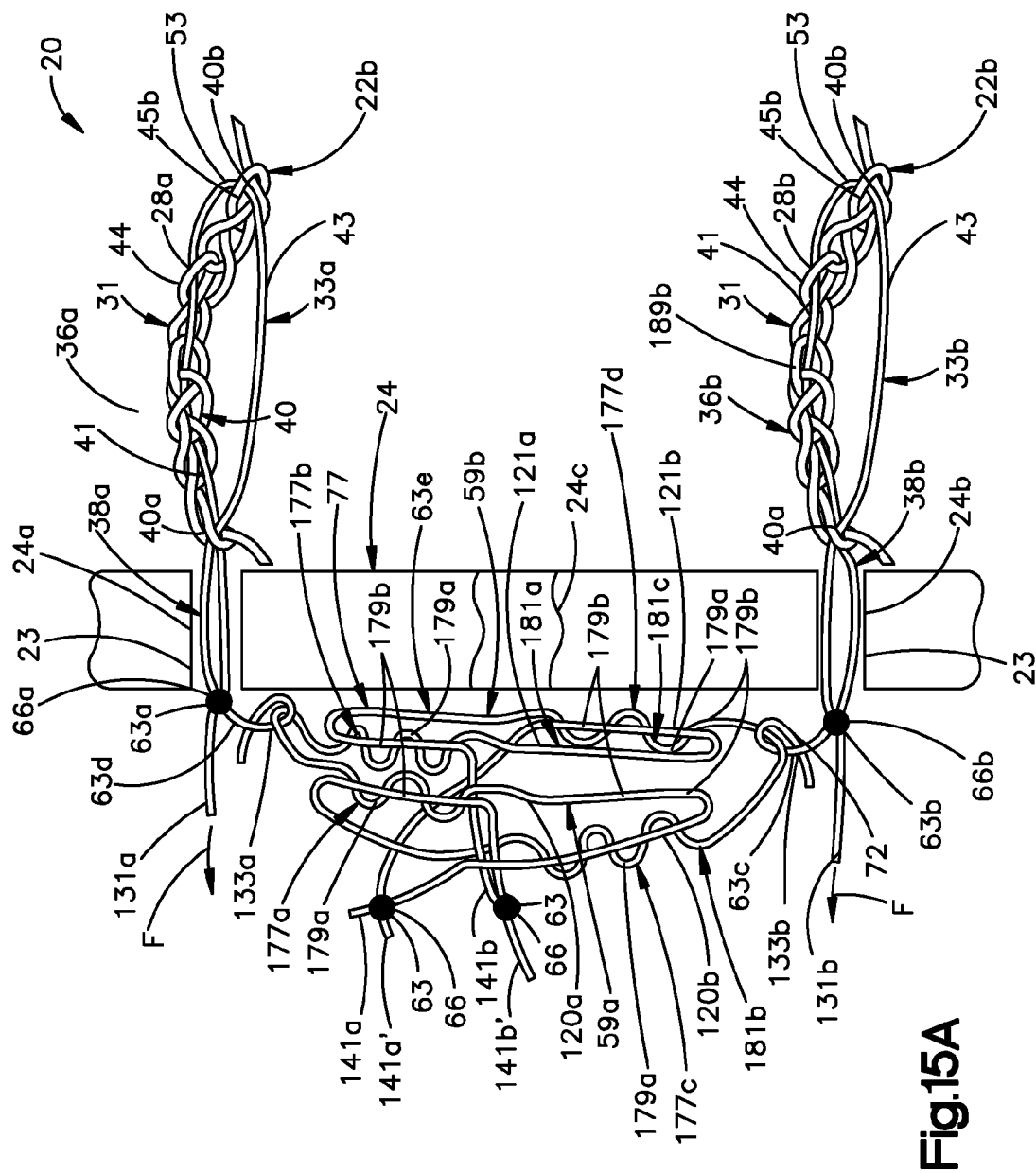
FIG. 15A is a side elevation view of an anchor assembly constructed in accordance with another embodiment, including first and second anchors shown in respective first configurations and implanted in an anatomical structure.
Figure 15B:
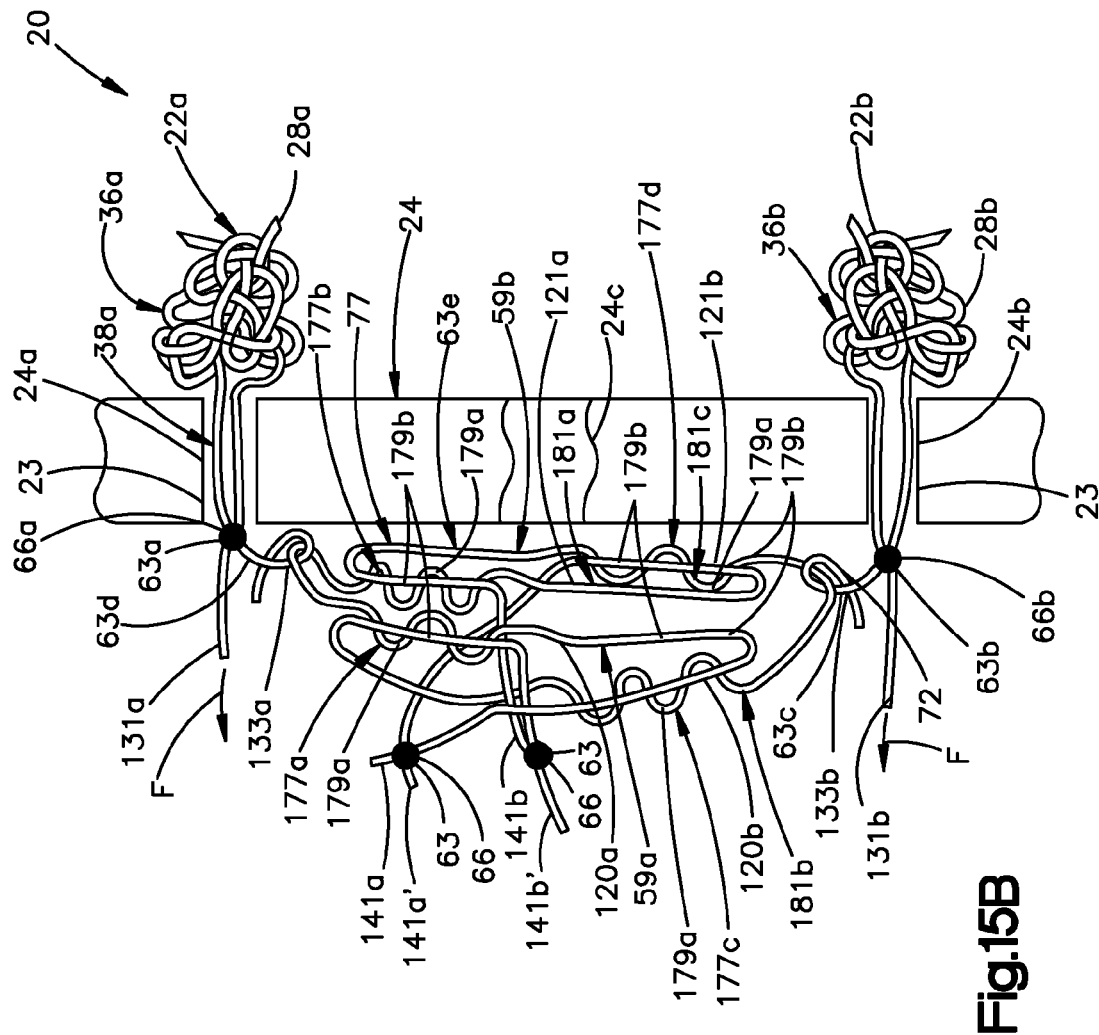
FIG. 15B is a side elevation view of the anchor assembly illustrated in FIG. 15A, showing the first and second anchors in respective expanded configurations.
Figure 15C:
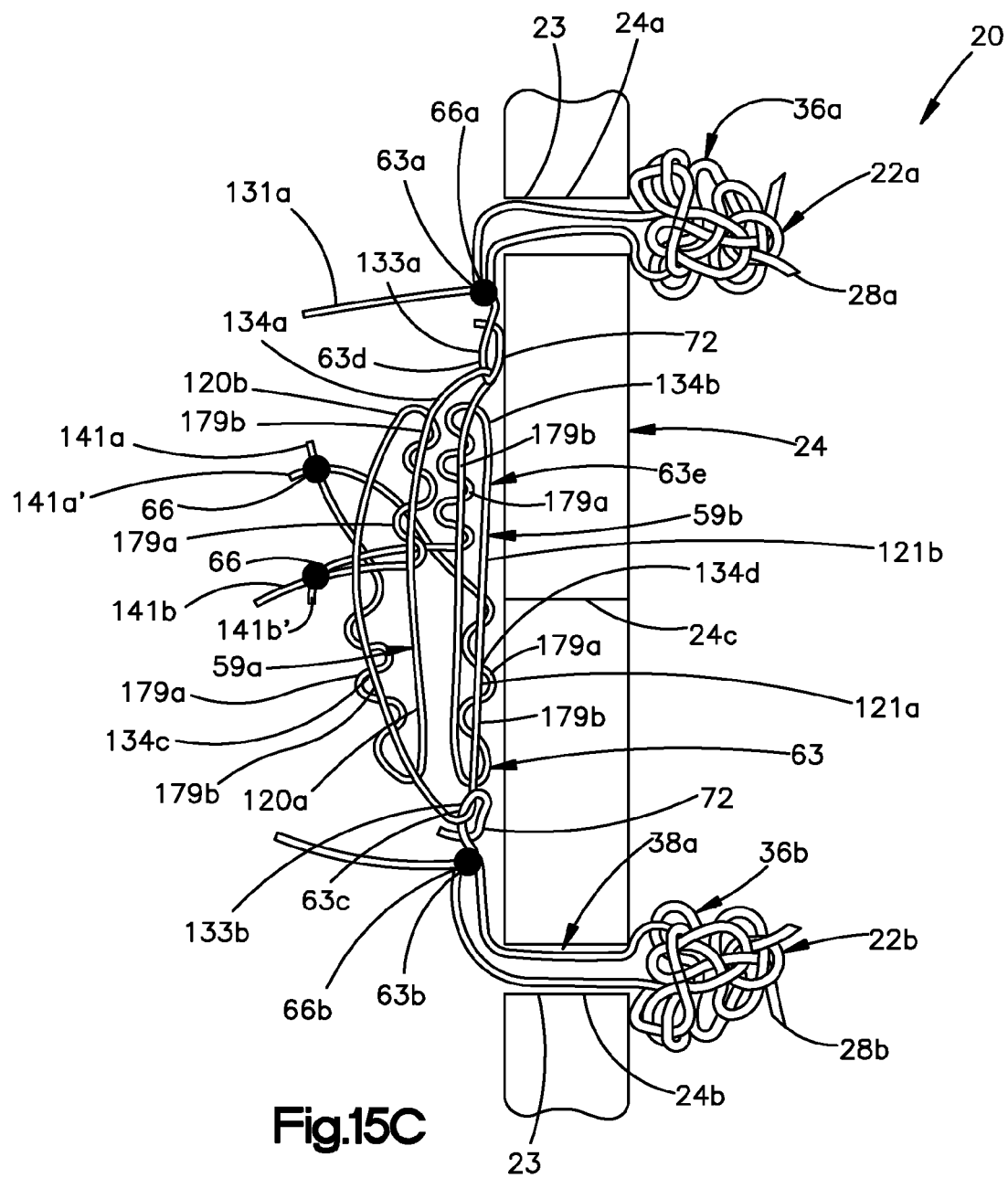
FIG. 15C is a side elevation view of the anchor assembly illustrated in FIG. 15B, showing the first and second anchors in an approximated configuration.

Referring now to FIGS. 15A-B, the anchor assembly 20 can include first and second connector members 63a and 63b configured as first and second knots 66a and 66b that attach the actuation portions 131a-b to the corresponding attachment portions 133a-b in the manner described above with respect to FIGS. 14A-D. Furthermore, as described above, the third and fourth connector members 63c-d can be defined by the second actuation strand 38b, and can be configured as an eyelet, for instance the eyelet 72 of the type described above with respect to FIG. 2H, though it should be appreciated that the eyelet can be alternatively constructed in accordance with any embodiment described herein or any suitable alternative embodiment In particular, the anchor assembly 20 can include at least one connector member that 66 is attached between the first and second actuation strands 38a and 38b. For instance, the at least one connector can be configured as a fifth connector member 63e can include at least one connector strand, such as a first connector strand 59a and a second connector strand 59b that are attached to each other and further attached between the first and second actuation strands 38a and 38b. Thus, it can be said that the anchor assembly 20 can include at least one connector strand 59 that is configured to be attached, directly or indirectly, to at least one of or both of the first and second actuation strands 38a and 38b, respectively. For instance, in accordance with the illustrated embodiment, the first connector strand 59a is directly attached to the first actuation strand 38a and the second connector strand 59b is directly attached to the second actuation strand 38b. In accordance with the illustrated embodiment, the first and second connector strands 59a-b are attached to the respective eyelets 72 of the first and second actuation strands 38a-b, which define sliding members 47 that allow the first and second actuation strands 59a-b to slide relative to the respective actuation strands 38a-b as described above. Thus, the first connector strand 59a is indirectly attached to the second actuation strand 38b via the second connector strand 59b, and the second connector strand 59b is indirectly attached to the second actuation strand 38b via the second connector strand 59b. While the connector members 63c and 63d are integral with the respective actuation strands, it should be appreciated that the connector members 63c and 63d can alternatively or additionally be integral with the respective connector strands 59a and 59b. It should be further appreciated that the anchor assembly 20 can include an auxiliary connector member 77 that is separate from and attached between the first connector strand 59a and the first actuation strand 38a, and an auxiliary connector member 77 that is separate from and attached between the second connector strand 59b and the second actuation strand 38b.

Thus, the anchor assembly 20 can include at least strand that is configured to attach, directly or indirectly, the first and second anchors 22a and 22b, including the respective first and anchor bodies 28a and 28b, including the respective first and second expandable portions 36a and 36b, to each other across the gap 24c. The at least one strand can be the actuation strand of at least one or both of the anchors 22a and 22b, or can be a strand that is separate from the actuation strands 38a and 38b. For instance, it should be appreciated in some embodiments that the actuation strands 38a and 38b can be removed after the anchor bodies 28a and 28b have actuated from their first configurations to their expanded configurations, and at least one connector member can be attached, directly or indirectly, to at least one or both of the first and second anchor bodies 28a and 28b so as to attach the anchor bodies 28a and 28b across the gap 24c.

In accordance with the illustrated embodiment, the anchor assembly 20 can include at least one such as a plurality of connector members 63 configured as a respective at least one stitch lock 177, such as a plurality of stitch locks 177 that can attach portions of the first and second connector strands 59a and 59b to each other. In accordance with the illustrated embodiment, the first connector strand 59a defines a first portion 120a and a second portion 121a, and the second connector strand 59b defines a first portion 120b and a second portion 121b. The at least one stitch lock 177 can attach at least one or both of the first and second portions 120a and 121a of the first connector strand 59a to at least one or both of the first and second portions 120b and 121b of the second connector strand 59b, thereby attaching the first and second actuation strands 38a and 38b together, indirectly via the connector strands 59a-b.

In accordance with the illustrated embodiment, the first connector strand 59a is folded through and thus extends through the eyelet 72 of the first actuation strand 38a so as to define the first and second portions 120a and 121a of the first connector strand 59a that are spaced from each other, such that the eyelet 72 of the first actuation strand 38a separates the first and second portions 120a and 121a. Likewise, the second connector strand 59b is folded through and thus extends through the eyelet 72 of the second actuation strand 38b so as to define the first and second portions 120b and 121b of the second connector strand 59b that are spaced from each other, such that the eyelet 72 of the second actuation strand 38b separates the first and second portions 120b and 121b. The first and second portions 120a and 121a of the first connector strand 59a extends toward the second anchor 22b, and the first and second portions 120b and 121b of the second actuation strand 38b extends toward the first anchor 22a. It should be appreciated that either or both of the connector strands 59a and 59b can be integral with the respective actuation strands 38a and 38b, and can extend through an eyelet of an anchor, such as the eyelet 90 or any alternatively constructed eyelet as described herein.

The first and second connector strands 59a-b can be attached to each other at one or more locations via any suitable connectors of the type described herein. For instance, the first connector strand 59b can be woven through another strand, such as the second connector strand 59b, so as to attach the first anchor 22a to the second anchor 22b. It should be appreciated that, for instance in embodiments wherein the second actuation strand 38b does not define an eyelet, the first connector strand 59a can be woven through the second actuation strand 38b so as to attach the first and second anchors 22a-b. In accordance with the illustrated embodiment, the first portion 120b of the second connector strand 59b can be woven or otherwise spliced through the first portion 120a of the first connector strand 59a at two different locations so as to define respective first and second stitch locks 177 a and 177b, and the first portion 120a of the first connector strand 59a can be woven or otherwise spliced through the first portion 120b of the second connector strand 59b at two different locations so as to define respective third and fourth stitch locks 177c and 177d. Thus, it should be appreciated that the anchor assembly 20 can include at least one such as a plurality of connector strands that can be attached to each other at one or more locations. For instance, each of the plurality of connector strands can be attached to each other at one or more stitch locks, such as splices 177a-d.

In accordance with the illustrated embodiment, the first stitch lock 177a can be defined by the first portion 120b of the second connector strand 59b and the first portion 120a of the first connector strand 59a. In particular, the first strand segment 179a can be defined by the first portion 120b of the second connector strand 59b, and the second strand segment 179b can be defined by the first portion 120a of the first connector strand 59a. Accordingly, the first portion 120b of the second connector strand 59b can be woven at least into, such as through, the first portion 120a of the first connector strand 59a as many times as desired along a direction, for instance away from the corresponding first anchor body 28a and toward the second anchor body 28b so as to define the first stitch lock 177a that attaches the first and second connector strands 59a-b, and thus also attaches the first and second anchors 22a-b. The first portion 120b of the second connector strand 59b can exit the first portion 120a of the first connector strand 59a so as to define a first terminal portion 141b of the second connector strand 59b.

The second stitch lock 177b can be defined by the second portion 121b of the second connector strand 59b and the second portion 121a of the first connector strand 59a. For instance, the first strand segment 179a of the second stitch lock 177b can be defined by the second portion 121b of the second connector strand 59b, and the second strand segment 179b of the second stitch lock 177b can be defined by the second portion 121a of the first connector strand 59a. Accordingly, the second portion 121b of the second connector strand 59b can be woven at least into, such as through, the second portion 121a of the first connector strand 59a as many times as desired along a direction, for instance away from the corresponding first anchor body 28a and toward the second anchor body 28b so as to define the second stitch lock 177b that attaches the first and second connector strands 59a-b, and thus also attaches the first and second anchors 22a-b. The second portion 121b of the second connector strand 59b can exit the second portion 121a of the first connector strand 59a so as to define a second terminal portion 141b' of the second connector strand 59b.

The first and second terminal portions 141b and 141b' can define free ends of the respective first strand segments 179a that are separate and spaced from each other, that is detached from each other, or can alternatively be attached to each other, either directly or indirectly via any suitable connector member 63 of the type described herein or any suitable alternatively constructed connector member 63. For instance, in accordance with the illustrated embodiment, the anchor assembly 20 can define a knot, such as the knot 66 of the type described above, that is defined by the first and second terminal portions 141b and 141b'. For instance, one of the terminal portions such as the first terminal portion 141b can define the post end 68 of the knot 66, and the other of the ends such as the second terminal portion 141b' can define the free end of the knot 66. Thus, when the knot 66 is in the unlocked configuration, the first terminal portion 141b is translatable with respect to the second terminal portion 141b' through the knot 66. The locking force can be applied to the free portion 70*b*, defined by the second terminal portion 141*b*', in the manner described herein so as to actuate the knot 66 to its locked configuration such that the first terminal portion 141*b* is translatably fixed with respect to the second terminal portion 141*b*' through the knot 66.

The third stitch lock 177*c* can be defined by the first portion 120*a* of the first connector strand 59*a* and the first portion 120*b* of the second connector strand 59*b*. For instance, the first strand segment 179*a* of the third stitch lock 177*c* can be defined by the first portion 120*a* of the first connector strand 59*a*, and the second strand segment 179*b* can be defined by the first portion 120*b* of the second connector strand 59*b*. Accordingly, the first portion 120*a* of the first connector strand 59*a* can be woven at least into, such as through, the first portion 120*b* of the second connector strand 59*b* as many times as desired along a direction, for instance away from the corresponding second anchor body 28*b* and toward the first anchor body 28*a* so as to define the third stitch lock 177*c* that attaches the first and second connector strands 59*a*-*b*, and thus also attaches the first and second anchors 22*a*-*b*. The first portion 120*a* of the first connector strand 59*a* can exit the first portion 120*b* of the second connector strand 59*b* so as to define a first terminal portion 141*a* of the first connector strand 59*a*.

The fourth stitch lock 177*d* can be defined by the second portion 121*a* of the first connector strand 59*a* and the second portion 121*b* of the second connector strand 59*b*. For instance, the first strand segment 179*a* of the fourth stitch lock 177*d* can be defined by the second portion 121*a* of the first connector strand 59*a*, and the second strand segment 179*b* of the fourth stitch lock 177*d* can be defined by the second portion 121*b* of the second connector strand 59*b*. Accordingly, the second portion 121*a* of the first connector strand 59*a* can be woven at least into, such as through, the second portion 121*b* of the second connector strand 59*b* as many times as desired along a direction, for instance away from the corresponding second anchor body 28*b* and toward the first anchor body 28*a* so as to define the fourth splice 134*d* that attaches the first and second connector strands 59*a*-*b*, and thus also attaches the first and second anchors 22*a*-*b*. The second portion 121*a* of the first connector strand 59*a* can exit the second portion 121*b* of the second connector strand 59*b* so as to define a second terminal portion 141*a*' of the first connector strand 59*a*.

In accordance with the illustrated embodiment, the first and second connector strands 59*a* and 59*b* define two pairs of stitch locks. The first pair includes stitch locks 177*a* and 177*c*, and the second pair includes stitch locks 177*b* and 177*d*. The first and second connector strands 59*a* and 59*b* define a first loop 181*a* between the first and second pairs of stitch locks, a second loop 181*b* disposed between the stitch locks 177*a* and 177*c* of the first pair of stitch locks, and a third loop disposed between the stitch locks 177*b* and 177*d* of the second pair of stitch locks. During operation, as the respective first strand segments 179*a* of the stitch locks 77*a*-*d* are translated through the respective second strand segments 179*b* away from the respective structures 189*a*-*b* (which define the first and second anchor bodies 28*a* and 28*b* in accordance with the illustrated embodiment), the first, second, and third loops 181*a*-*c* decrease in size, thereby causing the first and second connector strands 59*a* and 59*b* to apply a force to the respective structures 189*a* and 189*b* that biases the structures 189*a* and 189*b* toward each other.

The first and second terminal portions 141*a* and 141*a*' can define free ends of the respective first strand segments 179*a* that are spaced and separate from each other, that is detached from each other, or can alternatively be attached to each other, either directly or indirectly via any suitable connector member 63 of the type described herein or any suitable alternatively constructed connector member 63. For instance, in accordance with the illustrated embodiment, the anchor assembly 20 can define a knot, such as the knot 66 of the type described above, that is defined by the first and second terminal portions 141*a* and 141*a*'. For instance, one of the terminal portions such as the first terminal portion 141*a* can define the post end 68 of the knot 66, and the other of the ends such as the second terminal portion 141*a*' can define the free end 70 of the knot 66. Thus, when the knot 66 is in the unlocked configuration, the first terminal portion 141 *b* is translatable with respect to the second terminal portion 141*a*' through the knot 66. The locking force can be applied to the free portion 70*b*, defined by the second terminal portion 141*a*', in the manner described above so as to actuate the knot 66 to its locked configuration such that the first terminal portion 141*a* is translatably fixed with respect to the second terminal portion 141*a*' through the knot 66.

During operation, the first and second actuation strands 38*a* and 38*b* can each receive a respective actuation force F that causes the anchor bodies 28*a* and 28*b* to actuate from their respective first configurations to their respective expanded configurations when the knots 66*a* and 66*b* are in their respective unlocked configurations. The actuation force F can be applied directly to the first and second actuation strands 38*a* and 38*b* at the respective first and second actuation portions 131*a* and 131*b* as illustrated, or can be applied to the first and second actuation strand 38*a* and 38*b* at a location upstream of the respective first and second connector members 63*a* and 63*b*, respectively. The knots 66*a*-*b* can then be locked by applying a tensile locking force to the respective attachment portions 133*a*-*b* of the actuation strands 38. Alternatively, the tensile locking force can be applied by the approximation force AF, as will now be described.

For instance, once the anchor bodies 28*a* and 28*b* have actuated to their respective expanded configurations, each of the first and second terminal portions 141*a* and 141*b* of the first and second connector strands 59*a* and 59*b*, respectively, can each receive an approximation force AF that induces tension in the connector strands 59*a* and 59*b*, thereby applying the approximation force AF to the actuation strands 38*a* and 38*b* and biasing at least one or both of the anchors 22*a*-*b*, and thus the respective anchor bodies 28*a*-*b* toward the other to a biased position so as to approximate the gap 24*c*. It should be appreciated that the tension induced in the connector strands 59*a* and 59*b* further places the eyelet 72 in tension. Because the eyelet 72 is defined by the respective attachment portions 133*a*-*b*, the tension induced in the eyelet 72 creates a tensile force against the respective knots 66*a*-*b* that actuate the knots 66*a*-*b* to their locking configurations.

Furthermore, because the first and second connector strands 59*a*-*b* are placed under tension in response to application of the approximation forces AF, the first connector strand 59*a* can apply a compressive force to the second connector strand 59*b*, for instance at the first and second stitch locks 177*a*-*b*, so as to actuate the stitch locks 177*a*-*b* to their locked configurations. In particular, the first portion 120*a* of the first connector strand 59*a* can apply a compressive force to the first portion 120*b* of the second connector strand 59*b* at the first stitch lock 177*a*, and the second portion 121*a* of the first connector strand 59*a* can apply a compressive force to the second portion 121*b* of the second connector strand 59*b* at the second stitch lock 177*b*. The compressive forces applied by the first connector strand 59*a* to the second connector strand 59*b* can prevent translation of the second connector strand 59*b* with respect to the first connector strand 59*a* at the respective splices 134*a-b*.

Additionally, the second connector strand 59*b* can apply a compressive force to the first connector strand 59*a*, for instance at the third and fourth stitch locks 177*c-d*, thereby actuating the third and fourth stitch locks 177*c-d* to their respective locked configurations. In particular, the first portion 120*b* of the second connector strand 59*b* can apply a compressive force to the first portion 120*a* of the first connector strand 59*a* at the third stitch lock 177*c*, and the second portion 121*b* of the second connector strand 59*b* can apply a compressive force to the second portion 121*a* of the first connector strand 59*a* at the fourth stitch lock 177*a*, thereby actuating the fourth stitch lock 177*d* to its locked configuration. The compressive forces applied by the second connector strand 59*b* to the first connector strand 59*a* can reduce or prevent translation of the first connector strand 59*a* with respect to the second connector strand 59*b* at the respective splices 134*c-d*.

Once the gap 24*c* has been approximated, the knot 66 that attaches the respective first and second terminal portions 141*a* and 141*a*' of the first connector strand 59*a* can be actuated to its locked configuration, whereby the first and second portions 120*a* and 121*a* are prevented from translating relative to each other through the knot 66. Likewise, the knot 66 that attaches the respective first and second terminal portions 141*b* and 141*b*' of the second connector strand 59*b* can be actuated to its locked configuration, whereby the first and second portions 120*b* and 121*b* are prevented from translating relative to each other through the knot 66.

As described above, the anchor assembly 20 can include a connector member 63 that is attached between a first eyelet of the first anchor 22*a* and a second eyelet of the second anchor 22*b*. At least one or both of the first and second eyelets can be constructed in accordance with any suitable embodiment described herein or any suitable alternative embodiment. For instance, as illustrated in FIGS. 17A-18C, and 20A-B, at least one or both of the first and second eyelets can be configured as eyelets 90 as described above with reference to FIGS. 8A-11B.

As described with respect to FIGS. 12A-15C, the first and second strand segments 179*a* and 179*b* can be defined by two separate strands, which can be actuation strands 38*a* and 38*b* when the first and second structures 189*a* and 189*b* are configured as first and second anchor bodies 28*a* and 28*b*. The actuation strands 38*a* and 38*b* can be integral with the respective anchor bodies 28*a* and 28*b*, or can be separate from and attached to the respective anchor bodies 28*a* and 28*b*. Furthermore, the first and second strand segments 179*a* and 179*b* can be defined by connector strands that are attached to the respective first and second actuation strands 38*a* and 38*b* so as to attach the first and second actuation strands 38*a* and 38*b* to each other.

Alternatively, referring now to FIGS. 16A-E, at least one stitch lock 177 can be defined by the first and second strand segments 179*a* and 179*b* that, in turn, are defined by a common strand 175 that is looped around to define a loop 181, and woven to itself, such that the first and second strand segments 179*a* and 179*b* are integral with each other, and the loop 181 is closed by the stitch lock 177. In accordance with the illustrated embodiment, the first and second strand segments 179*a* and 179*b* can define at least one loop 181 disposed between the second end 187*a* of the first strand segment 179*a*, and the first end 185*b* of the second strand segment 179*b*. Either or both of the ends 187*a* and 185*b* of the first and second strand segments 179*a* and 179*b* can be attached to the first structure 189*a*. In accordance with one embodiment, the loop 181 is received by the first structure 189*a* such that first structure 189*a* is slidably attached to the loop 181 such that as the loop 181 decreases, the common strand 175 causes the structure 189 to be drawn toward the stitch lock 177, and thus toward the second end 187*b* of the second strand segment 179*b*, which can be attached to the second structure 189*b*. It should be further appreciated that as the loop 181 decreases in size, the second structure 189*b* can be drawn toward the first structure 189*a*. Thus, it can be said that decreasing the size of the loop 181 can draw at least one or both of the first and second structures 189*a* and 189*b* toward the other of the first and second structures 189*a* and 189*b*. As will be appreciated from the description below, the first and second strand segments 179*a* and 179*b* can define a second stitch lock so as to define a corresponding second loop 181. It should be appreciated that the first and second strand segments 179*a* and 179*b* can define as many stitch locks 177 as desired, so as to define any number of loops 181, as desired, that are slidably attached to as many respective structures 189 as desired.

As described above with respect to the stitch lock 177 defined by separate and thus non-integral first and second strand segments, the present inventors were surprised to discover that the stitch lock 177 is configured to iterate between an unlocked configuration and a locked configuration. When the stitch lock 177 is in the unlocked configuration, the first strand segment 179*a* is able to translate through the second strand segment 179*b* along a first direction toward the respective free end 185*a*, thereby decreasing the size of the loop 181 as illustrated in FIG. 16B, which shows the stitch lock 177 in the locked configuration. As the size of the loop 181 decreases, the first structure 189*a* is biased toward the second end 185*b* of the second strand segment 179*b*, which can be attached to a corresponding second structure 189*b*. When the stitch lock 177 is in the locked configuration, the stitch lock 177 prevents the first strand segment 179*a* from translating through the second strand segment 179*b* along a second direction opposite the first direction that would allow the size of the loop 181 to increase, even when the stitch lock 177 is constructed having a short length. Once the stitch lock 177 has been actuated from the unlocked configuration to a locked configuration, the stitch lock 177 prevents the first strand segment 179*a* from translating through the second strand segment 179*b* along both the first and second directions. For instance, the locked stitch lock 177 prevents the first strand segment 179*a* from translating through the second strand segment 179*b* whether a static tensile load is applied to the second end 187*a* of first strand segment 179*a*, or a cyclical load is applied to the second end 187*a* of the first strand segment 179*a* during normal anatomical function.

Referring again to FIG. 16A, and as described above with respect to separate first and second strand segments 179*a-b*, the stitch lock 177 that is defined by integral first and second strand segments 179*a-b* can be constructed as a woven construct whereby the first strand segment 179*a* defines a plurality of woven segments 193 that are woven at least into, for instance through, the second strand segment 179*b*. For instance, the first strand segment 179*a* can be woven at least into the second strand segment 179*b* along a direction from the first end 185*b* of the second strand segment 179*b* toward the second end 187*b* of the second strand segment 179*b* (e.g., toward the corresponding second structure 189*b*).

Thus, the first strand segment 179*a* can be woven at least into the second strand segment 179*b* along a direction away from the second end 187*b* of the second strand segment 179*b* (e.g., away from the second structure 189*b*). Alternatively, the first strand segment 179*a* can be woven at least into the second strand segment 179*b* along a direction from the first end 185*b* of the second strand segment 179*b* toward the second end 187*b* of the second strand segment 179*b* (e.g., toward the corresponding second structure 189*b*).

The first strand segment 179*a* defines a first woven segment 193*a* that extends at least into, for instance through, the second strand segment 179*b* along a first direction having a first directional component. For instance, the first woven segment 193*a* can extend into a first side 195*a* of the second strand segment 179*b* at an entry location 197*a* of the second strand segment 179*b*, and can further extend through the second strand segment 179*b* so as to exit from a second side 195*b* of the second strand segment 38 at an exit location 197*b* of the second strand segment 179*b*. The common strand 175 can have a body that defines the first and second strand segments 179*a-b* and the entry and exit locations 197*a* and 197*b* can be formed on the body. The first strand segment 179*a* can define a second woven segment 193*b* that extends at least into, for instance through, the second strand segment 179*b* at a location spaced from the first woven segment 193*a* along the second central axis 183*b* of the second strand segment 179*b*. The second woven segment 193*b* can extend at least into, for instance through, the second strand segment 179*b* along a second direction having a second directional component that is opposite the first directional component of the previous, or first, woven segment. Thus, the second direction can be opposite the first direction or otherwise angularly offset with respect to the first direction. For instance, in one embodiment, the second woven segment 193*b* can extend along the second direction into the second side 195*b* of the second strand segment 179*b* so as to define the corresponding entry location 197*a*, and can further extend through the second strand segment 179*b* so as to exit from the first side 195*a* of the second strand segment 179*b* at the corresponding exit location 197*b*. Alternatively, the exit location 197*b* of at least one or more of the woven segments 193 can be disposed on the same side as the corresponding entry location 197*a*. The entry location 197*a* of the second woven segment 193*b* can be spaced from the entry location 197*a* of the first woven segment 193*a* along the second central axis 183*b* of the second strand segment 179*b* in a direction from the second end 187*a* toward the first end 185*a* of the first strand segment 179*a*.

Thus, the first strand segment 179*a* defines a plurality of woven segments 193 that can each be defined by the first strand segment 179*a* at a location between adjacent entry locations 197*a*. The first strand segment 179*a* can define as many woven segments 193 as desired, such as greater than one. At least one up to all of the woven segments 193 extend through the second strand segment 179*b* along a respective direction that includes a directional component that is opposite the directional component of an adjacent one of the woven segments 193. It should be further appreciated that the woven segments 193 can cross the plane that includes the second central axis 183*b* of the second strand segment 179*b*, and can furthermore cross the second central axis 183*b* of the second strand segment 179*b*. The entry locations 197*a* of at least one up to all of the woven segments 193 can be spaced from the entry locations 197*a* of adjacent ones of the woven segments 193 along a direction substantially parallel to the second central axis 183*b* of the second strand segment 179*b*.

Furthermore, the exit location 197*b* at least one up to all of the woven segments 193 can be spaced from the corresponding entry location 197*a* along the second central axis 183*b* of the second strand segment 179*b* as desired. Alternatively or additionally, the exit location 197*b* of at least one up to all of the woven segments 193 can be aligned with the corresponding entry location 197*a* with respect to the central axis 183*b* of the second strand segment 179*b*. Thus, it should be appreciated that the first central axis 183*a* of the first strand segment 179*a* can define any angle as desired with respect to the second central axis 183*b* of the second strand segment 179*b* as desired at the exit location 197*b*, between and including approximately 0 degrees and approximately 180 degrees, including approximately 90 degrees. For instance, the first central axis 183*a* of the first strand segment 179*a* can define an angle of approximately zero degrees (or approximately 180 degrees) with respect to the second central axis 183*b* of the second strand segment 179*b* when the first strand segment 179*a* extends substantially along the second central axis 183*b* as the first strand segment 179*a* is disposed in the second strand segment 179*b*. The first strand segment 179*a* can exit the second strand segment 179*b* at the same side of the second strand segment 179*b* in which it entered, or in an opposite side of the second strand segment 179*b* in which it entered.

It should be further appreciated that the angle defined at the entry location 197*a* of a given woven segment 193 can be the same angle or a different angle that is defined at the corresponding exit location 197*b*. Thus, the woven segments 193 can be symmetrically arranged along the length of the second strand segment 179*b*, or can be asymmetrically arranged along the length of the second strand segment 179*b*. In accordance with one embodiment, the first and second sides 195*a-b*, and thus the entry location 197*a* and the exit location 197*b* of a given woven segment 193, can be disposed on opposite sides of a plane that includes the second central axis 183*b* of the second strand segment 179*b*. Adjacent woven segments 193 can extend through the second strand segment 179*b* at locations spaced from each other at any distance as desired along the second central axis 183*b* of the second strand segment 179*b*, for instance between and including approximately 0 mm and approximately 3 mm.

During operation, when the second strand segment 179*b* is in tension at a first level of tension at the stitch lock 177 that is less than a threshold level of tension (which includes a circumstance where the second strand segment is not in any tension, such that the first level of tension is zero), the stitch lock 177 is in an unlocked configuration, such that woven segments 193 of the first strand segment 179*a* can travel through the second strand segment 179*b*, for instance along a first direction from the second end 187*a* to the first end 185*a* when a tensile force is applied to the first end 185*a* of the first strand segment, such that the first end 185*a* translates away from the stitch lock 177 and the size of the loop 181 decreases. Thus, it should be appreciated that the stitch lock 177 defines a sliding member that permits the first strand segment 179*a* to translate through the second strand segment 179*b* when the stitch lock 177 is in the unlocked configuration.

A tensile force can be applied to the first ends 185*a* the first strand segment 179*a*, for instance when it is desired to apply a corresponding force to at least one or both of the first and second structures 189*a-b* that draws the at least one or both of the first and second structures 189*a-b* toward the other of the first and second structures. As the tension in the second strand segment 179*b* increases at the stitch lock 177, the second strand segment 179b applies a compressive force to at least one up to all of the woven segments 193 of the first strand segment 179a in the manner described above with respect to FIG. 13B.

Referring again to FIG. 16B, as the size of the loop 181 decreases, the length of the second strand segment 179b between the first and second structures 189a and 189b also decreases, thereby increasing the tension of the second strand segment 179b. Once the tension of the second strand segment 179b at the stitch lock 177 increases from the first level of tension to a second level of tension that is substantially equal to the threshold level of tension, the stitch lock 177 transitions to the locked configuration, such that the compressive force CF of the second strand segment 179b about the first strand segment 179a provides a locking force that produces a frictional engagement between the first and second strand segments 179a-b that prevents the woven segments 193 of the first strand segment 179a from translating through the second strand segment 179b at the stitch lock 177, both along the first direction, and along the second direction from the first end 185a toward the second end 187a, such that the first end 185a is prevented from translating toward the stitch lock 177. It should thus be appreciated that the stitch lock 177 can define a locking member that prevents the first strand segment 179a from translating through the second strand segment 179b when the stitch lock is in the locked configuration. In accordance with the illustrated embodiment, as the stitch lock 177 actuates to the locked configuration, the stitch lock 177 inverts, whereby the second actuation strand 179b straightens and the first actuation strand 179a becomes kinked about the second actuation strand 179b.

Referring now to FIG. 16C, the stitch lock assembly 191 can further include a tension relief instrument 199. For instance, if it is desired to further translate the first strand segment 179a through the second strand segment 179b along the second direction after the stitch lock 177 has been locked, the tension relief instrument 199 can apply an inwardly directed force to the second strand segment 179b at one end of the stitch lock 177 as descried above with reference to FIG. 13D, so as to compress the second strand segment 179b at the stitch lock 177, thereby reducing the tension of the second strand segment 179b at the stitch lock 177. The tension of the second strand segment 179b at the stitch lock 177 can be reduced to a level less than the threshold tension level, such that a tensile force applied to the first end 185a of the first strand causes the loop 181 to further decrease in size. For instance, the tension relief instrument 199 can include a handle 199a and an engagement member 199b that extends from the handle 199a. The engagement member 199b is configured to releasably abut the second strand segment 179b at a location adjacent the stitch lock 177. The handle 199a can be actuated so as to cause the engagement member 199b to compress the second strand segment 179b at the stitch lock 177, which allows the woven segments 193 of the first strand segment 179a to travel through the second strand segment 179b. Once the first strand segment 179a has translated a desired distance, the tension relief instrument 199 can be disengaged from the second strand segment 179b. If the tension in the second strand segment 179b is greater than the threshold level once the tension relief instrument has been disengaged from the second strand segment 179b, the compressive force applied by the second strand segment 179b against the first strand segment 179a prevents the woven segments 193 of the first strand segment 179a from translating through the second strand segment 179b at the stitch lock 177 as described above.

Referring now to FIG. 16D, the common strand 175 can define a pair of loops 181a and 181b joined by a bridge segment that is disposed between the loops 181a and 181b. Each of the loops 181a and 181b can be attached to corresponding first and second structures 189a and 189b in the manner described above, such that the first and second loops 181a and 181b are closed by the respective first and second stitch locks 177a and 177b. For instance, at least one or both of the loops 181a and 181b are slidably attached to the corresponding first and second structures. For instance, the common strand 175 can include a pair of opposed ends 175a and 175b, and a middle portion 175c that defines the bridge segment. Each of the opposed ends 175a and 175b can be looped so as to define the respective loops 181a and 181b, and woven through itself so as to define first and second stitch locks 177a and 177b of the type described above with respect to FIGS. 16A-C. The stitch lock 177 illustrated in FIG. 16D is shown in a tensioned configuration, whereby the second strand segment 179b extends substantially straight, and the first strand segment 179a is curved about the second strand segment 179b.

The first strand segments 179a of the stitch locks 177a and 177b can be defined by the respective ends 175a and 175b of the common strand 175, and the second strand segments 179b of the stitch locks 177a and 177b is defined by the middle portion 175c of the common strand 175. The first and second loops 181a and 181b can be disposed between the respective stitch locks 177a and 177b and pairs of the second end 187a and first end 185b of the first and second strand segments 179a and 179b, respectively, that define the respective stitch locks 177a and 177b. At least one or both of the first strand segments 179a can be woven at least into, such as through, the respective second strand segments 179b along a direction from the corresponding loops 181a and 181b toward the middle portion 175c that defines the bridge segment. Alternatively, at least one or both of the first strand segments 179a can be woven at least into, such as through, the respective second strand segments 179b along a direction from the bridge segment toward the corresponding loops 181a and 181b.

During operation, each of the first or free ends 185a of the first strand segment 179a can be placed under tension, which causes the first strand segment 179a to slide relative to the second strand segment 179b when the tension level of the second strand segment 179b is less than the threshold tension level, thereby decreasing the size of the first and second loops 181a and 181b. As the loops 181a and 181b decrease in size, the first and second structures 189a and 189b are drawn toward their respective stitch locks 177a and 177b, and thus are drawn towarwd each other. It should be further appreciated that as the loops 181a and 181b decrease in size, the tension of the second strand segment 179b can increase to the threshold level, thereby locking the respective stitch locks 177a and 177b. In this regard, it should be appreciated that the bridge strand, defined by the middle portion 175c, can be configured as a brace structure 203, such that the tension level of the second strand segment 179b is defined between the respective first and second structures and the brace structure 203. Thus, the brace structure can be a separate structure that is attached to the second strand segment 179b as described above with respect to FIGS. 13A-D, can be defined by one of the structures 189a and 189b (such as the second structure 189b) as illustrated in FIGS. 16A-C, or can be integral with the second strand segment 179b as illustrated in FIGS. 16D-A tension relief instrument, for instance of the type illustrated in FIG. 16C, can be applied to one or both of the stitch locks 177a and 177b so as to decrease the tension of the second strand segment 179b at the respective stitch lock, thereby allowing a tensile force applied to the respective first end 185a to further decrease the size of the respective loop.

Figure 16E:
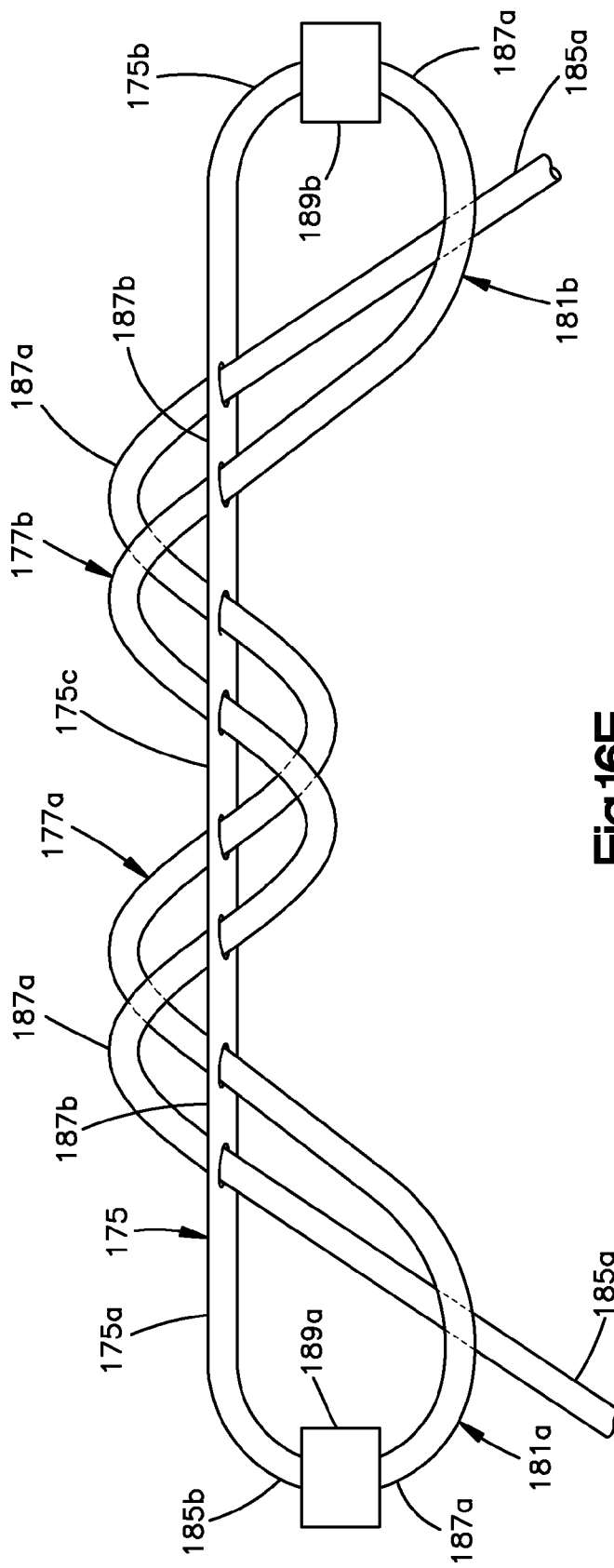
FIG. 16A is a side elevation view of a stitch lock assembly including a stitch lock constructed in accordance with an alternative embodiment, wherein the stitch lock includes first and second strand segments that are integral with each other so as to define a loop.
FIG. 16B is a side elevation view of the stitch lock assembly illustrated in FIG. 16A, shown under tension and inverted.
FIG. 16C is a side elevation view of the stitch lock assembly illustrated in FIG. 16B, including a tension relief instrument.
FIG. 16D is a side elevation view of the stitch lock assembly as illustrated in FIG. 16A, wherein the first and second strand segments define a pair of stitch locks that define a respective pair of loops joined by a bridge strand segment.
FIG. 16 E is a side elevation view of the stitch lock assembly similar to the stitch lock assembly illustrated in FIG. 16D, but showing the first and second stitch locks overlapping each other.

While the first and second stitch locks 177a and 177b can be spaced apart from each other, for instance separated by the bridge defined by the middle portion 175c as illustrated in FIG. 16D, it should be appreciated that the first and second stitch locks 177a and 177b can be constructed as described above with respect to FIG. 16D but can at least partially overlap each other, for instance along the middle portion 175c as illustrated in FIG. 16E. Accordingly, an applied tensile force to the first free ends 185a of the first strand segments 179a of each stitch lock 177a and 177b decreases the size of the respective loop 181a and 181b until the tension of the respective second strand segment 179b reaches the threshold tension level, which actuates the stitch locks 177a and 177b to the locked configuration.

Figure 17A:
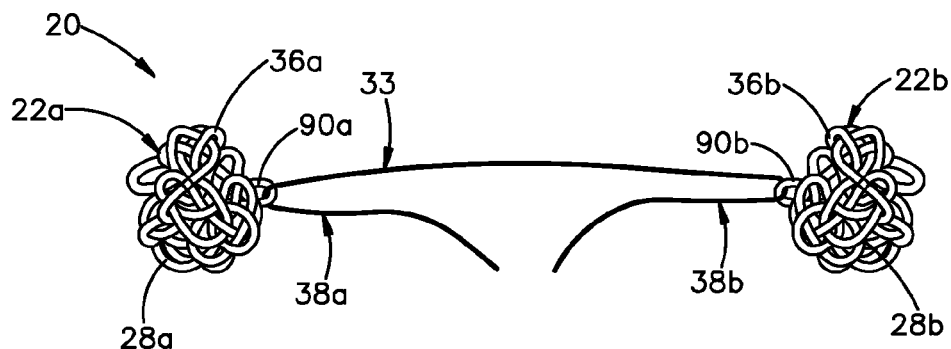
FIG. 17A is a side elevation view of an anchor assembly constructed in accordance with another alternative embodiment, including first and second anchors shown in respective first configurations.
Figure 17B:
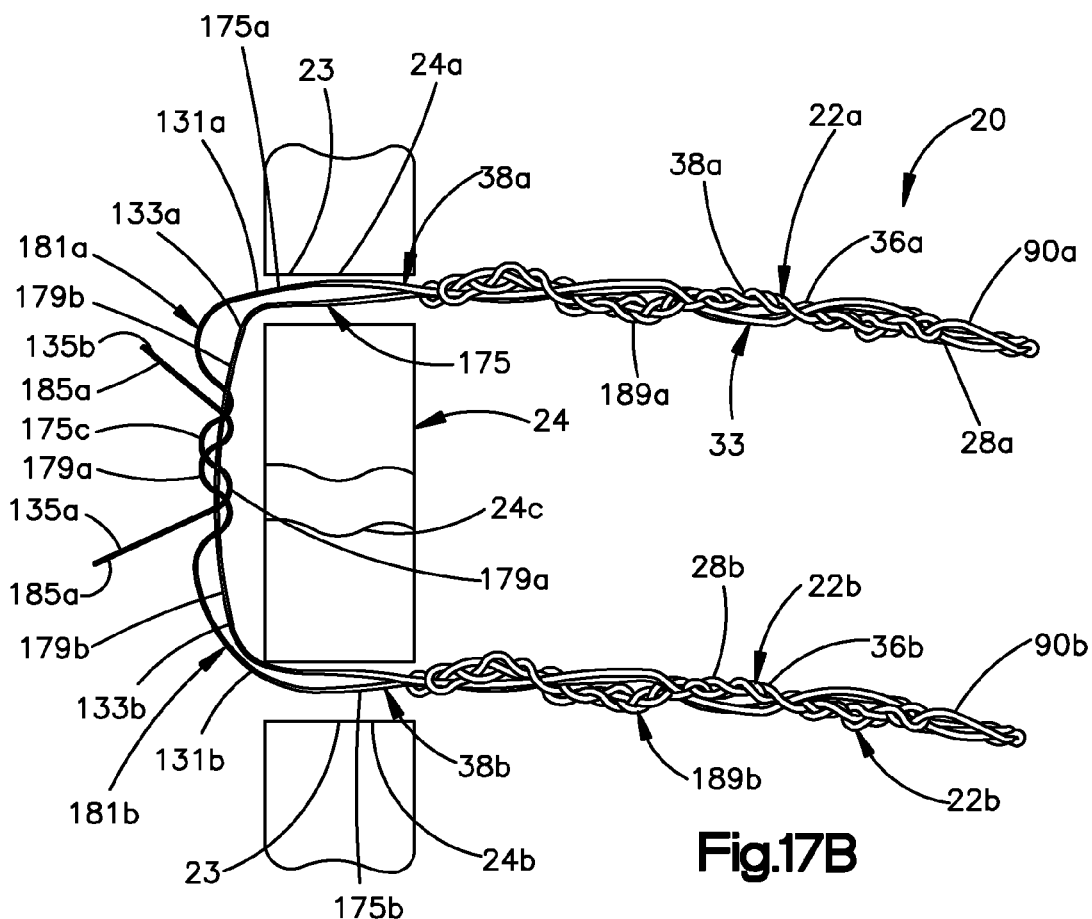
FIG. 17B is a side elevation view of an anchor assembly illustrated in FIG. 17A, shown implanted in a target anatomical structure.
Figure 17C:
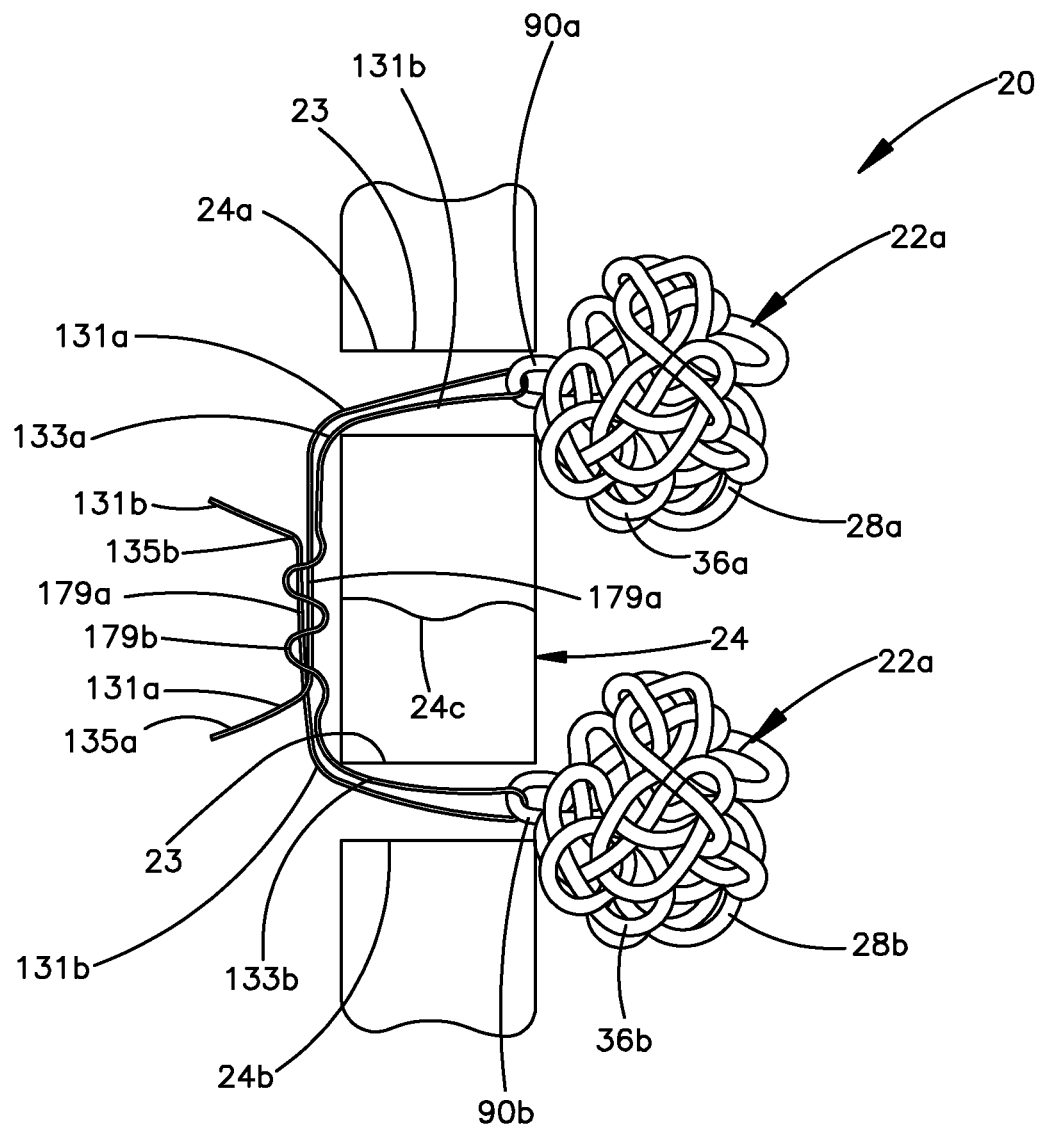
FIG. 17C is a side elevation view of the anchor assembly illustrated in FIG. 17B, showing the first and second anchors in respective expanded configurations.

Referring to FIGS. 17A-C, and as described above with respect to FIGS. 8A-C, the auxiliary strand 33 can extend through the eyelet 90 and can be woven through the anchor body 28 so as to define a path for the eyelet 90 through the anchor body 28 when the anchor body 28 is actuated from the first configuration to the expanded configuration. Furthermore, the auxiliary strand 33 can be configured as a deployment strand that facilitates attachment of the anchor 22 to another anchor, or can alternatively or additionally be configured as an actuation strand that receives the actuation force causing the anchor to be actuated from the first configuration to the expanded configuration once implanted in the anatomical structure 24.

In accordance with the illustrated embodiment, the anchor assembly 20 can include a first and second anchor 22a and 22b each including respective eyelets 90a and 90b that are actuated to their expanded configuration as described above with respect to FIGS. 8A-C. Next, the auxiliary strand 33 of one of the anchors 22a-b can be removed from the respective eyelet 90a-b, and the auxiliary strand 33 of the other of the anchors 22a-b can be fed through the eyelet 90a-b of the anchor 22a-b from which the auxiliary strand was removed. Thus, the auxiliary strand 33 of one of the anchors can define the first actuation strand 38a and the second actuation strand 38b. Alternatively, the auxiliary strands 90a-b of both off the anchors 22a and 22b can be removed from the respective eyelets 90a-b, and a new auxiliary strand 33 can be fed through both eyelets 90a and 90b so as to attach the first anchors 22a and 22b to each other. Thus, FIG. 17A illustrates an auxiliary strand 33 that is separate from both anchor bodies 28a and 28b and extends through the respective eyelets 90a and 90b so as to define respective actuation strands 38a and 38b that are integral with each other.

As illustrated in FIG. 17C, the anchor bodies 28a and 28b can be urged along the respective actuation strands 38a and 38b from their respective expanded configurations to their respective first configurations. Accordingly, the actuation strands 38a and 38b extend through the same respective openings of the anchor bodies 28a and 28b as described above with respect to the auxiliary strand 33 as illustrated in FIGS. 8A-C. Thus, the actuation strands 38a and 38b define a first and second actuation portions 131a-b, respectively, and first and second attachment portions 133a-b. The first and second actuation portions 131a-b are configured to receive respective actuation forces F that actuate the anchor bodies 28a-b to their expanded configurations in the manner described above, and the first and second actuation portions 131a-b are configured to attach to each other. For instance, the first and second actuation portions 131a-b can be integral with each other, or can be attached via any suitable connector member of the type described herein.

With continuing reference to FIGS. 17A-C, the anchor assembly can include a connector member 63 that can be configured to attach to the first and second actuation portions 131a and 131b, thereby attaching the first and second actuation strands 38a and 38b to each other, and also attaching the anchors 22a and 22b to each other. The attachment portions 133a-b of the auxiliary strand 33 can be attached, for instance integrally in accordance with the illustrated embodiment, across the gap 24c.

As described above, the connector member 63 that can define at least one of a sliding member 47 and a locking member 64 that attaches the first and second actuation strands 38a and 38b together. For instance, the connector member 63 can be configured as a pair of stitch locks 177a and 177b that is defined by the auxiliary strand 33, such that the auxiliary strand 33 defines the common strand 75, the first and second actuation strands 38a-b, for instance at the respective first and second actuation portions 131a and 131b, define the respective first strand segments 79a, and the first and second actuation strands 38a-b, for instance at the respective first and second attachment portions 133a and 133b, define the respective second strand 79b. The stitch locks 177a and 177b can overlap as described above with respect to FIG. 16E, or can be spaced apart as described above with respect to FIG. 16D. The common strand 75 can define a first loop 181a which can include the first actuation portion 131a and the first attachment portion 133a, and a second loop 181b which can include the second actuation portion 131b and the second attachment portion 133b. The loops 181a-b can be attached, for instance, slidably attached, to first and second structures 189a and 189b, which can be configured as the first and second anchor bodies 28a and 28b, respectively. The first and second actuation portions 131a-b can define corresponding terminal portions 135a-b that define free ends 185a of the respective first strand segments 179a.

During operation, a tensile approximation force AF can be applied to the terminal portions 135a and 135b of the respective actuation portions 131a-b, so as to decrease the size of the respective loops 181a-b. The loops 181a-b are slidably attached to a pair of structures 181a and 181b that are configured as the first and second anchor bodies 28a and 28b. For instance, the loop 181 is received by the respective eyelets 90a-b. The loops 181a-b decrease in size in response to the applied approximation force AF. As the loops 181a-b decrease in size, the loops 181a-b draw the attached first and second anchor bodies 28a and 28b toward each other in the manner described above.

As the first and second anchor bodies 28a and 28b move toward each other so as to approximate the gap 24c, tension increases in the first and second attachment portions 133a-b, which can define the second strand segments 179b of the first and second stitch locks 177a-b. As the tension in the second attachment portions 133a-b increase at the corresponding stitch locks 177a-b, the second attachment portions 133a-b apply a compressive forces to at least one up to all of the woven segments defined by the respective first and second actuation portions 131a in the manner described above. Once the tension in the attachment portions 133a-b reaches the second level that is substantially equal to the threshold level of tension, the stitch locks 177a-b actuate to the locked configuration, whereby compressive forces applied by the second attachment portions 133a-b to the respective actuation portions 131a-b prevents the actuation portions 131a-b from translating relative to the respective attachment portions 133a-b, and thus fixes the size of the corresponding loops 181a-b. Accordingly, the stitch locks 177a-b prevent the size, which can be an area, of the loops 181a-b from both increasing and decreasing.

A tension relief tool, such as the type of tension relief tool 199 illustrated in FIG. 16C can compress one or both of the first and second attachment portions 133a-b at the respective stitch locks 177a-b in the manner described above so as to decrease the tension in the attachment portions 133a-b to a level below the threshold level of tension at the stitch lock 177, which thereby allows the respective actuation portions 131a-b to slide through the corresponding attachment portion 133a-b to further decrease the size of the respective loops 181a-b and draw the first and second anchor bodies 22a and 228b further toward each other. The tension relief tools can be removed from the attachment portions 133a-b to again prevent the size of the loops 181a-b from both decreasing and increasing.

Figure 18A:
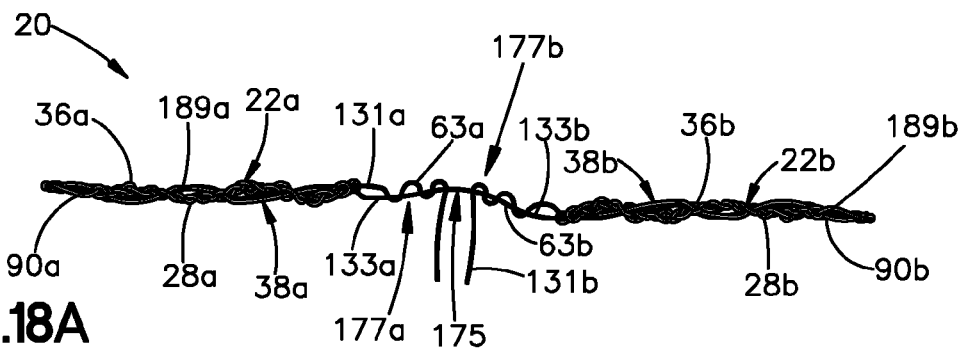
FIG. 18A is a side elevation view of an anchor assembly constructed in accordance with another embodiment, showing the first and second anchors in respective first configurations.
Figure 18B:
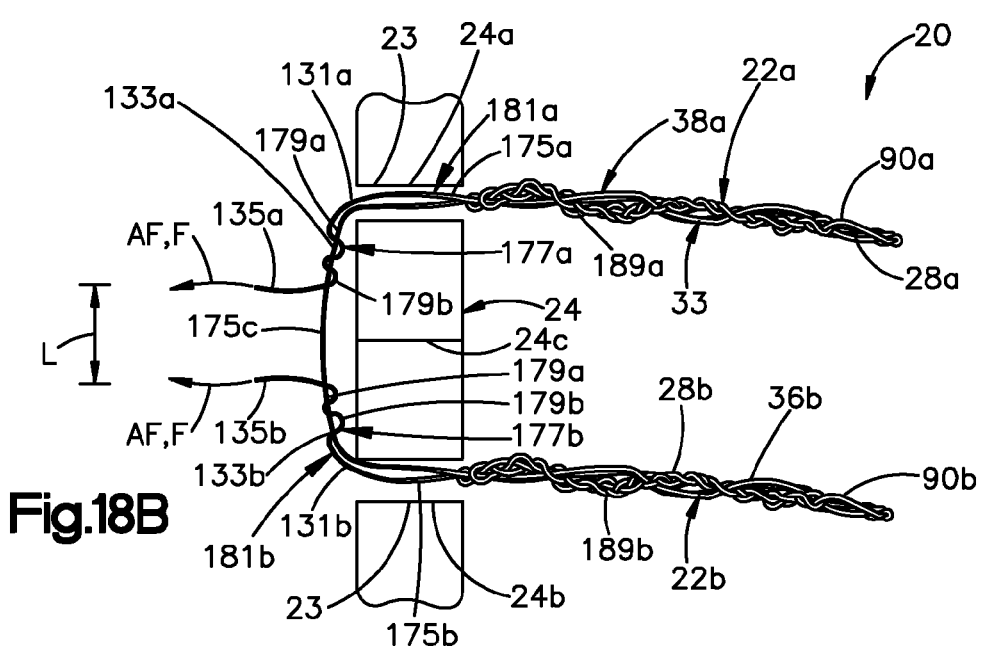
FIG. 18B is a side elevation view of an anchor assembly illustrated in FIG. 18A, shown implanted in a target anatomical structure.
Figure 18C:
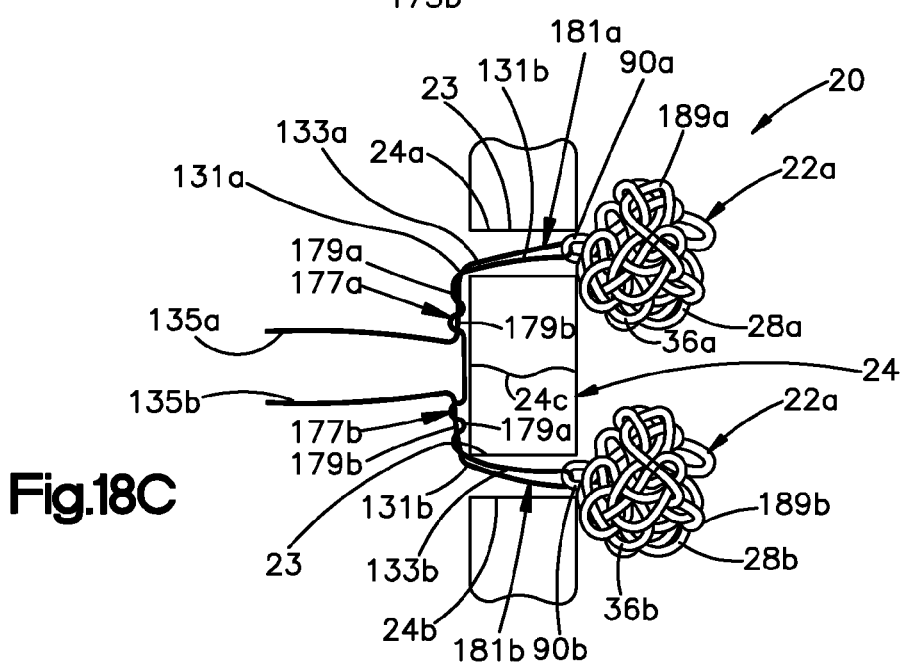
FIG. 18C is a side elevation view of the anchor assembly illustrated in FIG. 18B, showing the first and second anchors in respective expanded configurations.

Referring now to FIGS. 18A-C, the anchor assembly 20 as described above with reference to FIGS. 17A-C can include a plurality of connector members 63 configured as first and second stitch locks 177a and 177b that are spaced apart from each other and configured to attach the actuation strands 38a and 38b to each other. In accordance with the illustrated embodiment, the common strand 75 defines the first and second actuation strands 38a and 38b, which are thus integral with each other. The common strand is defined by the auxiliary strand 33, such that the respective attachment portions 133a and 133b of the first and second actuation strands 38a and 38b are integral with each other. Thus, in accordance with the illustrated embodiment, the first and second actuation strands 38a and 38b are integral with each other. In accordance with the illustrated embodiment, the anchor assembly 20 can include first and second stitch locks 177a and 177b that are configured to attach the actuation portions 131a and 131b to other locations of the common strand 75, and thus to each other. For instance, the first stitch lock 177a can attach the first actuation portion 131a of the first actuation strand 38a to the first attachment portion 133a of the first actuation strand 38a. Similarly, the second stitch lock 177b can attach the second actuation portion 131b of the second actuation strand 38b to the second attachment portion 133b of the second actuation strand 38b.

In accordance with the illustrated embodiment, the first actuation portion 131a of the first actuation strand 38a defines the first strand segment 179a of the first stitch lock 177a, and the first attachment portion 133a of the first actuation strand 38a defines the second strand segment 179b of the first stitch lock 177a. It should be appreciated that the first stitch lock and the first end 175a of the common strand 175 defines a first loop 181a that is slidably attached to the eyelet 90a of the first anchor body 28a, which defines the first structure 189a. In accordance with the illustrated embodiment, the second actuation portion 131b of the second actuation strand 38b defines the first strand segment 179a of the second stitch lock 177b, and the second attachment portion 133b of the second actuation strand 38b defines the second strand segment 179b of the second stitch lock 177b. It should be appreciated that the second stitch lock 177b and the second end 175b of the common strand 175 defines a second loop 181b that is slidably attached to the eyelet 90b of the second anchor body 28b, which defines the second structure 189b. The middle portion 175c of the common strand 175, which can be defined by the first and second attachment portions 133a and 133b, can be connected between the first and second loops 181a and 181b. In accordance with an alternative embodiment at least one of the second attachment portions 133a and 133b of the respective stitch locks 177a and 177b can define the first strand segment, and the corresponding actuation portions 131a and 131b can define the second strand segment.

During operation, a tensile actuation force F can be applied to the first and second actuation strands 38a and 38b, for instance at the respective terminal portions 135a and 135b, or at the attachment portions 133a and 133b. The actuation force F causes the anchor bodies 28a and 28b to expand from the first configuration to the expanded configuration in the manner described above. Next, an approximation force AF can be applied to the first and second actuation strands 38a and 38b, for instance at the respective terminal portions 135a and 135b that define the respective first and second ends 175 and 175b of the common strand 175.

A tensile approximation force AF can be applied to at least one or both of the terminal portions 135a and 135b of the respective actuation portions 131a-b, which define the respective first ends of the first and second strand segments, so as to decrease the size of the respective first and second loops 181a-b. Each of the loops 181a and 181b is slidably attached to the corresponding anchor bodies 28a and 28b. For instance the loops 181a and 181b are received by the respective eyelets 90a-b. The loops 181a-b decrease in size in response to the applied approximation force AF. As the loops 181a-b decrease in size, the loops 181a-b draw the each of the corresponding first and second anchor bodies 28a and 28b toward the other of the first and second anchor bodies 28a and 28b.

As the first and second anchor bodies 28a and 28b move toward each other so as to approximate the gap 24c, tension increases in the second strand segments 179b at the first and second stitch locks 177a-b. As the tension in the second strand segments 179b increases at the stitch locks 177a-b, the second strand segments 179b apply compressive forces against at least one up to all of the woven segments defined by the first and second actuation portions 131a-b in the manner described above. Once the tension in the first and second attachment portions 133a-b reaches the second level that is substantially equal to the threshold level of tension, the stitch lock actuates to the locked configuration, whereby compressive forces applied by the first and second attachment portions 133a-b to the corresponding first actuation portion 131a-b prevents the first and second actuation portions 131a-b from translating relative to the respective first and second attachment portions 133b, and thus fixes the size of the corresponding loops 1811-b. Accordingly, the stitch locks 177a-b prevent the corresponding size, which can be an area, of the loops 181a-b from both increasing and decreasing.

The tension relief tool 199 illustrated in FIG. 16D can compress either or both of the first and second attachment portions 133a-b in the manner described above so as to decrease the tension level to a level below the threshold level of tension at the stitch lock 177, which thereby allows the corresponding first and second actuation portions 131a to slide through the first and second attachment portions 133a-b to further decrease the size of the corresponding loops 181a-b and draw the first and second anchor bodies 22a and 228b further toward each other.

Figure 19A:
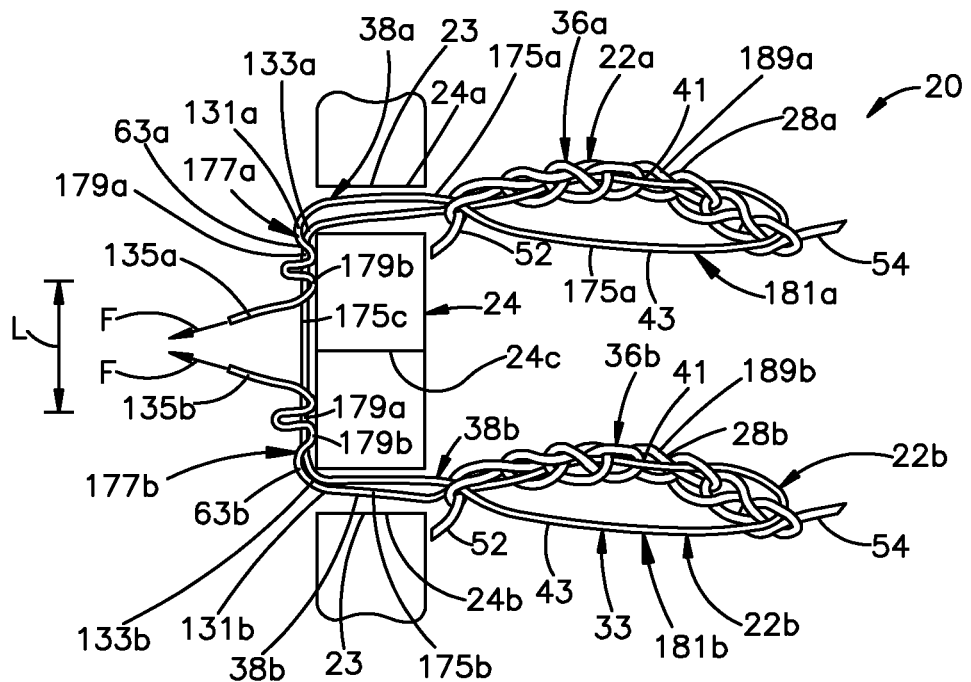
FIG. 19A is a side elevation view of an anchor assembly constructed in accordance with another embodiment, including first and second anchors shown in respective first configurations and implanted in an anatomical structure.
Figure 19B:
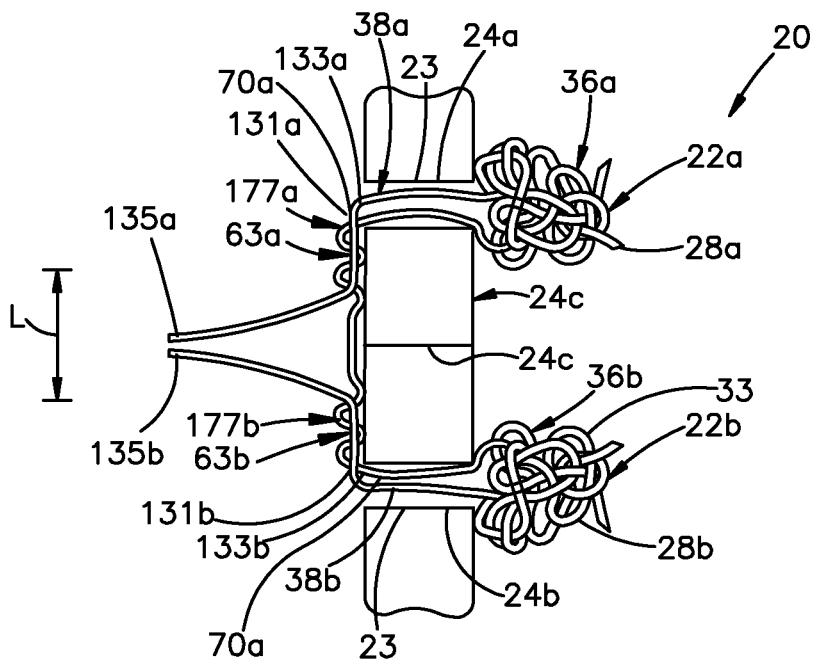
FIG. 19B is a side elevation view of the anchor assembly illustrated in FIG. 19A, showing the first and second anchors in respective expanded configurations.

Referring now to FIGS. 19A-B, the anchor assembly 20 as described above with respect to FIGS. 1A-B can include a pair of anchors 22a and 22b that include anchor bodies 28a and 28b and respective actuation strands 38a and 38b. The first and second actuation strands 38a and 38b can be defined by a common strand 175 such that the first and second actuation strands 38a and 38b can be integral with each other. The common strand 175, and thus the first and second actuation strands 38a and 38b can define an auxiliary strand 33 that is woven through the corresponding anchor bodies 28a and 28b in the manner described above. In accordance with the illustrated embodiment, the actuation strands 38a and 38b are defined by the auxiliary strand 33, such that the respective attachment portions 133a and 133b are integral with each other.

The first and second stitch locks 177a and 177b are configured to attach the actuation portions 131a and 131b to other locations of the common strand, for instance at the respective first and second attachment portions. In accordance with the illustrated embodiment, the first actuation portion 131a of the first actuation strand 38a defines the first strand segment 179a of the first stitch lock 177a, and the first attachment portion 133a of the first actuation strand 38a defines the second strand segment 179b of the first stitch lock 177a. It should be appreciated that the first stitch lock 177a and the first end 175a of the common strand 175 defines a first loop 181a that is slidably attached to the first anchor body 28a, which defines the first structure 189a. For instance, the first end 175a of the common strand 175 can be woven through the first anchor body 28a.

In accordance with the illustrated embodiment, the second actuation portion 131b of the second actuation strand 38b defines the first strand segment 179a of the second stitch lock 177b, and the second attachment portion 133b of the second actuation strand 38b defines the second strand segment 179b of the second stitch lock 177b. It should be appreciated that the second stitch lock 177b and the second end 175b of the common strand 175 defines a second loop 181b that is slidably attached to the second anchor body 28b, which defines the second structure 189b. For instance, the second end 175b of the common strand 175 can be woven through the second anchor body 28b. The middle portion 175c of the common strand 175, which can be defined by the first and second attachment portions 133a and 133b, can be connected between the first and second loops 181a and 181b. In accordance with an alternative embodiment at least one of the second attachment portions 133a and 133b of the respective stitch locks 177a and 177b can define the first strand segment, and the corresponding actuation portions 131a and 131b can define the second strand segment.

During operation, a tensile actuation force F can be applied to the first and second actuation strands 38a and 38b, for instance at the respective terminal portions 135a and 135b, or at the attachment portions 133a and 133b. The actuation force F causes the anchor bodies 28a and 28b to expand from the first configuration to the expanded configuration in the manner described above. Next, an approximation force AF can be applied to the first and second actuation strands 38a and 38b, for instance at the respective terminal portions 135a and 135b, of the first and second actuation portions 131a-b, that define the respective first and second ends 175 and 175b of the common strand 175.

The tensile approximation force AF can be applied to at least one or both of the terminal portions 135a and 135b of the respective actuation portions 131a-b, which define the respective first ends of the first and second strand segments, so as to decrease the size of the respective first and second loops 181a-b. Each of the loops 181a and 181b is slidably attached to the corresponding anchor bodies 28a and 28b. For instance the loops 181a and 181b are received by the respective eyelets 90a-b. The loops 181a-b decrease in size in response to the applied approximation force AF. As the loops 181a-b decrease in size, the loops 181a-b draw the each of the corresponding first and second anchor bodies 28a and 28b toward the other of the first and second anchor bodies 28a and 28b.

As the first and second anchor bodies 28a and 28b move toward each other so as to approximate the gap 24c, tension increases in the second strand segments 179b at the first and second stitch locks 177a-b. As the tension in the second strand segments 179b increases at the stitch locks 177a-b, the second strand segments 179b apply compressive forces against at least one up to all of the woven segments defined by the first and second actuation portions 131a-b in the manner described above. Once the tension in the first and second attachment portions 133a-b reaches the second level that is substantially equal to the threshold level of tension, the stitch lock actuates to the locked configuration, whereby compressive forces applied by the first and second attachment portions 133a-b to the corresponding first actuation portion 131a-b prevents the first and second actuation portions 131a-b from translating relative to the respective first and second attachment portions 133b, and thus fixes the size of the corresponding loops 1811-b. Accordingly, the stitch locks 177a-b prevent the corresponding size, which can be an area, of the loops 181a-b from both increasing and decreasing.

The tension relief tool 199 illustrated in FIG. 16D can compress either or both of the first and second attachment portions 133a-b in the manner described above so as to decrease the tension level to a level below the threshold level of tension at the stitch lock 177, which thereby allows the corresponding first and second actuation portions 131a to slide through the first and second attachment portions 133a-b to further decrease the size of the corresponding loops 181a-b and draw the first and second anchor bodies 22a and 228b further toward each other.

Figure 20A:
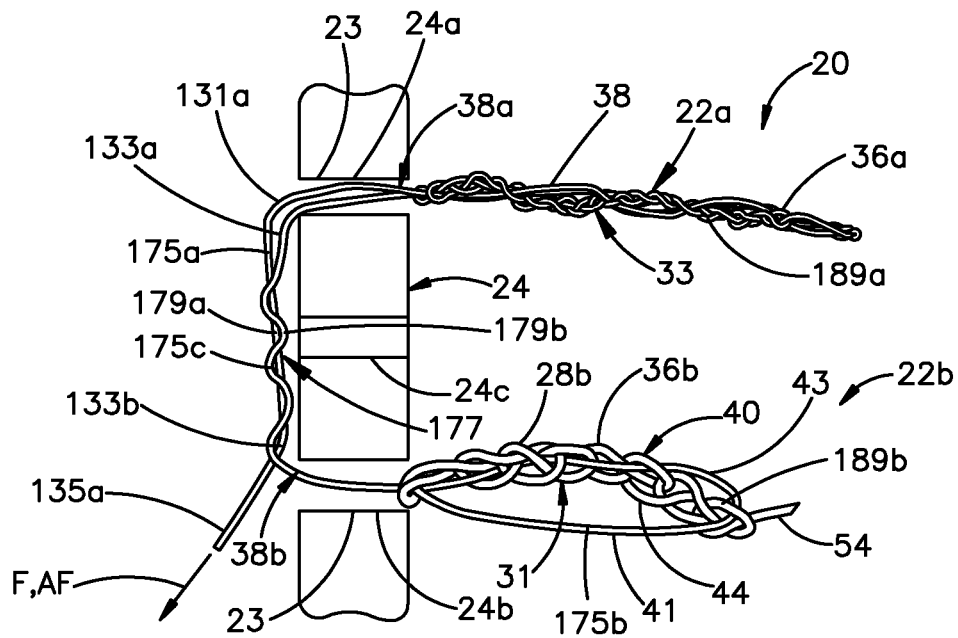
FIG. 20A is a side elevation view of an anchor assembly constructed in accordance with another embodiment, including first and second anchors shown implanted in a target anatomical structure, and showing the first and second anchors in respective first configurations.
Figure 20B:
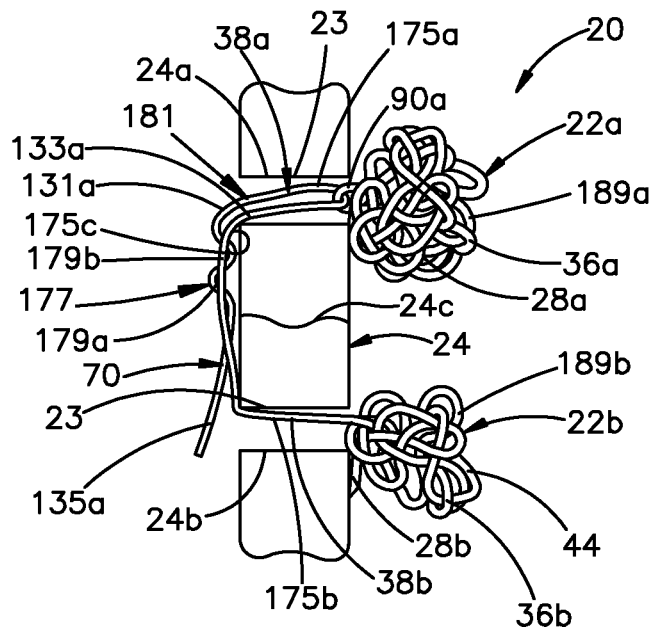
FIG. 20B is a side elevation view of the anchor assembly illustrated in FIG. 20A, showing the first and second anchors in respective expanded configurations.

Referring now to FIGS. 20A-B, the anchor assembly 20 can include a first anchor 22a including the respective eyelet 90a as described above with reference to FIGS. 17A-C, and the second anchor 22b can include the respective anchor body 28b having an integral actuation strand 28b as described above with respect to FIGS. 12A-C. Thus, as described above, one of the actuation strands 38a and 38b can be integral with the respective anchor body 28a and 28b, and the other of the actuation strands 38b and 38b can be separate from and woven through the respective anchor body 28a and 28b so as to attach the actuation strand to the anchor body. In accordance with the illustrated embodiment, the integral actuation strand 38b of the second anchor 22b defines the auxiliary actuation strand 38a of the first anchor 22a. Thus, as described above with respect to FIGS. 6A-B, the first portion 41 of the second anchor body 22b can define both the respective actuation portion 131b and the attachment portion 133b. Furthermore, the first and second actuation strands 38a and 38b are defined by a common strand 175, such that the first and second actuation strands 38a and 38b are integral with each other as described above. Alternatively, the first and second actuation strands 38a and 38b can be separate from each other and attached to each other, for instance, via the stitch lock 177 as described herein.

In accordance with the illustrated embodiment, the attachment portion 133b of the second actuation strand 38b can be integral with the attachment portion 133a of the first actuation strand 38a. The first actuation strand 38a can be woven through the anchor body in the manner described above with respect to FIGS. 8A-C, such that the first actuation strand 38a can define a path that the eyelet 90a can travel as the anchor body 28a is actuated from the first configuration to the expanded configuration. Furthermore, the first or actuation portion 131a and the second or attachment portion 133a extend out from the first anchor body 28a and are spaced from each other in the manner described above. In accordance with the illustrated embodiment, the first actuation strand 38a defines the first strand segment 179a of the stitch lock 177, and the second actuation strands 38b defines the second strand segment 179b of the stitch lock 177. Thus, the first actuation strand 38a is woven at least into, for instance through, the second actuation strand 38b so as to define the stitch lock 177.

In accordance with the illustrated embodiment, the first end 175a of the common strand 175 is attached to the eyelet 90a of the anchor body 28a, and woven through the middle portion 175c so as to define the first stitch lock 177. Thus, the first end 175a of the common strand, which includes the first actuation strand 38a, defines a loop 181 that is slidably attached to the first anchor body 28a, which defines the first structure 189a. The second end 175b of the common strand 175, which includes the second actuation strand 38b is attached to the second anchor body 28b. For instance, in accordance with the illustrated embodiment, the second actuation strand 38b, and thus the second end 175b of the common strand 175, is integral with the second anchor body 28b.

During operation, the first actuation strand 38a, and in particular the terminal portion 135a of the actuation portion 131a of the first actuation strand 38a can receive the tensile actuation force F that causes the first anchor body 28a to actuate from its respective first configuration to the expanded configurations, and also induces tension in the first and second actuation strands 38a-b. The tension induced in the second actuation strand 38b by the first actuation strand 38a applies an actuation force F to the second actuation strand 38b, thereby causing the respective second anchor body 28b to actuate from the first configuration to the expanded configuration.

Next, the first terminal portion 135a can receive an approximation force AF that induces tension in the first and second actuation strands 38a that biases at least one or both of the anchor bodies 28a and 28b toward the other of the anchor bodies 28a and 28b to a biased position so as to approximate the gap 24c. For instance, the tension in the first actuation strand 38a causes the loop 181 to decrease in size which biases the first anchor body 28a toward the second anchor body. Tension in the second actuation strand 38b biases the second anchor body 28b toward the first anchor body 28a. The approximation force AF can be a continuation of the actuation force F if, for instance, the actuation force F is applied to the terminal portions 135a. It should be appreciated that once both the first and second actuation strands 38a and 38b are placed under tension, the second actuation strand 38b applies a compressive force to the first actuation strand 38a at the splice 134 that is sufficient to prevent the first actuation strand 38a from backing out of the second splice 134b along a direction toward the first anchor body 28a.

As the first and second anchor bodies 28a and 28b move toward each other s as to approximate the gap 24c, tension increases in the second actuation strand 38b. As the tension in the second actuation strand 38b increases at the stitch lock 177, the second actuation strand 38b applies compressive forces against at least one up to all of the woven segments defined by the first actuation strand 38a in the manner described above. Once the tension in the second actuation strand 38 reaches the second level that is substantially equal to the threshold level of tension at the stitch lock 177, the stitch lock 177 actuates from the unlocked configuration to the locked configuration, whereby the compressive forces applied by the second actuation strand to the first actuation strand prevents the first actuation strand 38a from translating through the second actuation strand 38b. The tension relief tool 199 can decrease the tension in the second strand 38b in the manner described above if it is desired to further bias the first and second anchor bodies 28a and 28b toward each other.

Figure 21A:
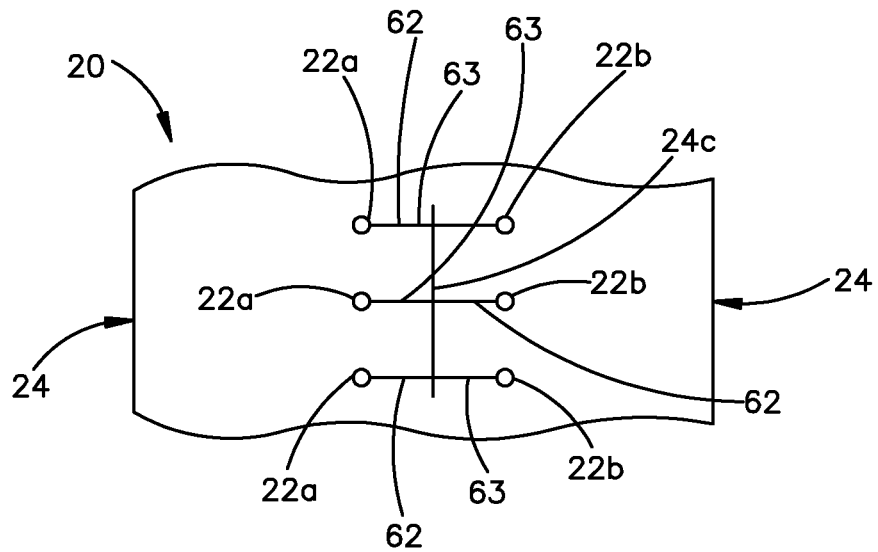
FIG. 21A is a schematic top plan view of an anchor assembly constructed in accordance with an alternative embodiment, including multiple pairs of anchors attached to each other across an anatomical defect.
Figure 21B:
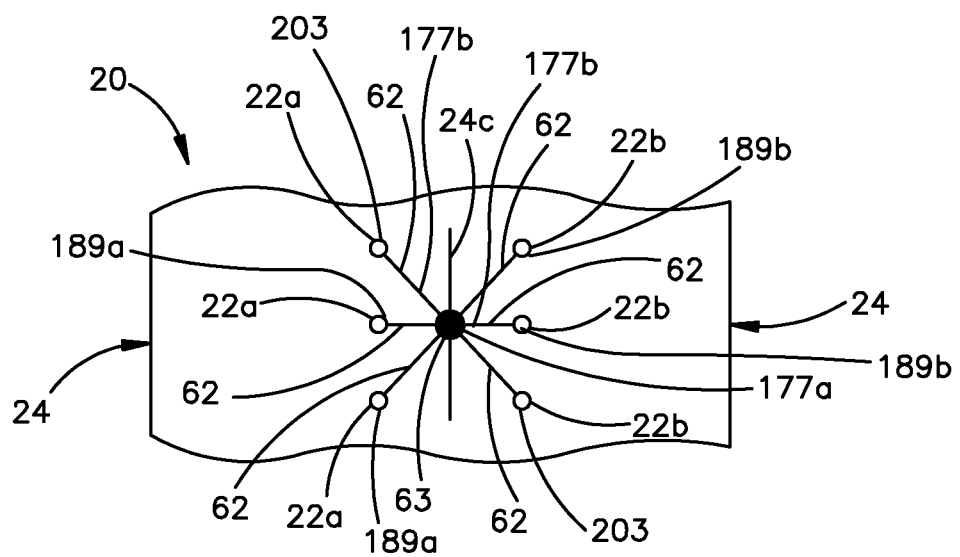
FIG. 21B is a schematic top plan view of an anchor assembly constructed in accordance with an alternative embodiment, including a plurality of anchors attached to each other across an anatomical defect at a common hub.

While the anchor assembly 20 has been described above in accordance with embodiments that illustrated a pair of anchors 22a and 22b attached across a defect, it should be appreciated that the anchor assembly 20 can include as many anchors as desired, that can be attached to each other in any manner and arrangement as desired. for instance, referring to FIG. 21A, the anchor assembly 20 can include multiple pairs of first and second anchors 22 and 22b attached on opposed sides of a gap 24c, which can be the same anatomical defect or different anatomical defects. The first and second anchors 22a and 22b of each pair of anchors can be attached in accordance with any of the embodiments described herein or any suitable alternative embodiment. Alternatively, referring to FIG. 21B, a plurality of pairs of first and second anchors 22a and 22b can be implanted in the target anatomical structure 24 across a gap 24c, and the anchor assembly 20 can include a connector member 63 configured to attach each of the anchors 22 and 22b to each other at a common hub 240. The connector member 63 can be configured as any suitable connector member as desired that can, for instance, attach at least one up to all of attachment portions of the anchors 22a and 22b and connector strands of the anchors 22a and 22b. For instance the connector members 63 can be configured as stitch locks 177a-b of the type described above that join first and second structures 189a-b to a brace structure 203. The first and second structures 189a-b and the brace structure 203 can be configured as anchor bodies of anchors 22 implanted at respective target anatomical locations as described above, or any alternatively constructed anchor body attached to an anatomical structure as desired, or alternatively still any anatomical structure as desired.

In accordance with certain aspects of the present disclosure, a method can be provided for biasing first and second structures to each other. The method can include the steps of 1) weaving a first segment of a strand of suture at least into a second segment of a strand of suture a portion so as to define at least four woven segments of the first segment that are woven at least into the second segment, each of the woven segments defined at least by an entry location whereby the first segment enters the second segment, 2) attaching the first strand to a first structure; 3) attaching the second strand to a second structure, 4) translating the first strand through the second strand so as to bias at least one of the first and second structures toward the other of the first and second structures until a tension in the second strand reaches a level that is substantially equal to a threshold tension level, and 5) applying a compressive force from the second segment to the first segment so as to prevent the first segment from translating through the second segment once the tension in the second strand has reached the level that is substantially equal to the threshold tension level.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein, unless otherwise indicated. Accordingly, those skilled in the art will realize that the invention is intended to encompass all modifications and alternative arrangements included within the spirit and scope of the invention, for instance as set forth by the appended claims.

We claim:

1. A stitch lock assembly, comprising:
a common strand of suture having a body including a first segment and a second segment of the common strand, the common strand being elongate along a central axis so as to define a length, the second segment including a first side and a second side that are on opposite sides of the central axis, the first segment woven through the second segment along a portion of the length of the second segment so as to define a stitch lock having at least two woven segments of the first segment that are woven through the second segment, each of the at least two woven segments defined at least by a respective entry location where the first segment enters one of the first and second sides of the second segment, and a respective exit location where the first segment exits from the other of the first and second sides of the second segment, wherein the respective entry and exit locations are formed on the body, and the common strand at the first segment passes through the body between the respective entry and exit locations at the second segment so as to define each of the at least two woven segments,
wherein 1) the at least two woven segments are configured to translate through the second segment when the second segment is in tension at a first level of tension that is less than a threshold level of tension, and 2) the second segment applies a compressive force to the first segment when the second segment is in tension at a second level of tension that is at least substantially equal to the threshold level of tension so as to prevent the at least two woven segments of the first segment from translating through the second segment; and
wherein the common strand is configured to attach to first and second anchors, such that as the at least two woven segments translate through the second segment, the common strand 1) applies a respective actuation force to each of the first and second anchors so as to cause the first and second anchors to expand, and 2) biases the first and second anchors toward each other.

2. The stitch lock assembly as recited in claim 1, wherein the first segment is elongate along a first portion of the central axis, the second segment is elongate along a second portion of the central axis, and the first portion of the central axis defines an angle with respect to the second portion of the central axis at least at one of the entry locations, the angle between and including approximately 0 degrees and approximately 180 degrees.

3. The stitch lock assembly as recited in claim 1, wherein adjacent ones of the at least two woven segments extend through the second segment at locations spaced apart a distance including approximately 0 mm and approximately 3 mm.

4. The stitch lock assembly as recited in claim 2, wherein the first segment is elongate along the first portion of the central axis, the second segment is elongate along the second portion of the central axis, and each of the first and second segments defines a respective first end and a respective second end spaced from each other along the respective first and second portions of the central axis, such that the woven segments are disposed between the first and second ends of the first segment, and the woven segments are disposed between the first and second ends of the second segment.

5. The stitch lock assembly as recited in claim 4, wherein, when the second segment is in tension at the first level of tension, the first segment is translatable through the second segment so as to bias the first and second anchors toward each other.

6. The stitch lock assembly as recited in claim 1, wherein the first and second anchors are expandable anchors, wherein the first anchor includes a first anchor body and a first actuation member that is configured to receive the respective actuation force that causes the first anchor body to expand.

7. The stitch lock assembly as recited in claim 6, wherein the first actuation member is integral with the first anchor body and defines one of the first and second segments.

8. The stitch lock assembly as recited in claim 6, wherein the first actuation member is separate from the first anchor body and defines one of the first and second segments.

9. The stitch lock assembly as recited in claim 6, wherein the second anchor includes a second anchor body and a second actuation member configured to receive the respective actuation force that causes the second anchor body to expand.

10. The stitch lock assembly as recited in claim 9, wherein the respective first and second anchor bodies include respective first and second eyelets, and the respective first and second actuation members are inserted through the respective first and second eyelets.

11. The stitch lock assembly as recited in claim 10, wherein the first actuation member defines the first and second segments.

12. The stitch lock assembly as recited in claim 10, wherein the stitch lock is a first stitch lock, the stitch lock assembly further comprising a second stitch lock that includes a respective first segment and a respective second segment, wherein the respective first segment is woven at least into the respective second segment, the first segment of the second stitch lock is defined by the second actuation member, and the second segment of the second stitch lock is defined by the second actuation member.

13. The stitch lock assembly as recited in claim 12, further comprising a loop that is disposed between the first and second stitch locks, wherein the loop is configured to decrease in size as the first segment of at least one of the first and second stitch locks is translated through the associated second segment.

14. The stitch lock assembly as recited in claim 12, wherein the first and second segments of at least one of the first and second stitch locks are separate from and attached to the first and second actuation members.

15. The stitch lock assembly as recited in claim 12, wherein the first and second stitch locks define a first pair of stitch locks, the stitch lock assembly further comprising a second pair of the first and second stitch locks.

16. The stitch lock assembly as recited in claim 15, comprising a first loop disposed between the first and second pairs of stitch locks, a second loop disposed between the first and second stitch locks of the first pair of stitch locks, and a third loop disposed between the first and second stitch locks of the second pair of stitch locks.

17. The stitch lock assembly as recited in claim 15, wherein the first, second, and third loops are configured to decrease in size when the first segments of each of the stitch locks of the first and second pairs of stitch locks are translated through the associated second segment.

18. The stitch lock assembly as recited in claim 10, wherein one of the first and second anchors includes an eyelet, and the first and second segments are attached to the eyelet.

19. The stitch lock assembly as recited in claim 1, wherein the common strand defines a loop that is closed by the stitch lock, and the loop is configured to decrease in size as the at least two woven segments translate through the second segment.

20. The stitch lock assembly as recited in claim 19, wherein the loop is slidably attached to the first and second anchors.

21. The stitch lock assembly as recited in claim 19, wherein, as the loop decreases in size, the first anchor is biased toward the second anchor.

22. The stitch lock assembly as recited in claim 19, wherein the stitch lock is a first stitch lock, the stitch lock assembly further comprising a second stitch lock that includes a respective first segment and a respective second segment, wherein the respective first segment is woven at least into the respective second segment.

23. The stitch lock assembly as recited in claim 22, wherein the loop is a first loop, the common strand defines a second loop that is closed by the second stitch lock, and the second loop is configured to decrease in size as the first segment of the second stitch lock translates through the second segment of the second stitch lock.

24. The stitch lock assembly as recited in claim 23, wherein the common strand comprises a first end that defines the first loop, a second end that defines the second loop, and a bridge segment that is connected between the first and second loops.

25. The stitch lock assembly as recited in claim 23, wherein each of the first and second loops is attached to the corresponding first and second anchors, and the first and second anchors are biased toward each other as the first and second loops decrease in size.

26. The stitch lock assembly as recited in claim 1, further comprising a tension relief instrument configured to compress the second segment so as to reduce the tension in the second segment to a level less than the threshold tension level.

27. The stitch lock assembly of claim 1, wherein the stitch lock is configured to transition between a) an unlocked configuration when the second segment is at the first level of tension, whereby the second segment is folded between adjacent ones of the at least two woven segments, and b) a locked configuration when the second segment is in tension at the second level of tension, whereby the second segment substantially straightens and the first segment is folded and is prevented from translating through the second segment.

28. A method for biasing first and second anchors attached to a common strand of suture toward each other, the method comprising the steps of:
    weaving a first segment of a body of the common strand of suture through a first side of a second segment of the body of the common strand and out of a second side of the second segment that is opposite the first side with respect to a central axis of the second segment, such that the first segment defines at least two woven segments of the first segment that are woven through the second segment, each of the at least two woven segments defined at least by a respective entry location where the first segment enters one of the first and second sides of the second segment, and a respective exit location where the first segment exits the other of the first and second sides of the second segment, wherein the respective entry and exit locations are formed on the body, and the common strand at the first segment passes through the body between the respective entry and exit locations at the second segment so as to define each of the at least two woven segments;
    translating the first segment through the second segment so as to 1) impart respective actuation forces to the first and second anchors in a manner causing the first and second anchors to expand, and 2) bias at least one of the first and second anchors toward the other of the first and second anchors until a tension in the second segment reaches a level that is substantially equal to a threshold tension level; and
    in response to the translating step, causing the second segment to apply a compressive force to the first segment so as to prevent the first segment from translating through the second segment once the tension in the second segment has reached the level that is substantially equal to the threshold tension level.

29. The method of claim 28, wherein the at least two woven segments of the first segment of the body of the common strand of suture woven through the second segment of the body of the common strand of suture define a stitch lock, wherein during the translating step the stitch lock transitions from an unlocked configuration where the second segment is folded between adjacent ones of the at least two woven segments, the method further comprising the step of:
    after the translating step, further tensioning the second segment to a second level of tension greater than the threshold tension level, such that the second segment substantially straightens and the first segment becomes folded and is prevented from translating through the second segment.

30. The method of claim 29, wherein the common strand defines a loop that is closed by the stitch lock, and the translating step comprises decreasing a size of the loop as the at least two woven segments translate through the second segment so that at least one of the first and second anchors is biased toward the other of the at least one of the first and second anchors.

31. The method of claim 30, wherein the stitch lock is a first stitch lock, and the loop is a first loop, wherein the weaving step includes weaving a respective first segment through a portion of a respective second segment to define a second stitch lock, wherein the second stich lock closes a second loop that is defined by the common strand,
    wherein the translating step further comprises decreasing a size of the second loop as the respective first segment translates through the respective second segment of the second stitch lock.

32. The method of claim 28, wherein prior to the translating step, tensioning the second segment at a first level of tension that is less than the threshold tension level, such that the first segment is translatable through the second segment.

33. The method of claim 28, wherein the first and second anchors include respective first and second anchor bodies that are expandable, and respective first and second actuation members, wherein the method comprises the step of:
    applying the respective actuation forces to the first and second actuation members so as to cause the first and second anchor bodies to expand.

* * * * *